United States Patent
Wills et al.

(10) Patent No.: US 11,077,233 B2
(45) Date of Patent: Aug. 3, 2021

(54) PHARMACEUTICAL AND OTHER PACKAGING WITH LOW OXYGEN TRANSMISSION RATE

(71) Applicant: SIO2 MEDICAL PRODUCTS, INC., Auburn, AL (US)

(72) Inventors: Matthew Wills, Opelika, AL (US); Ahmad Taha, Auburn, AL (US); Christopher Weikart, Auburn, AL (US)

(73) Assignee: SiO2 Medical Products, Inc., Auburn, AL (US)

(*) Notice: Subject to any disclaimer, the term of this patent is extended or adjusted under 35 U.S.C. 154(b) by 321 days.

(21) Appl. No.: 15/753,524

(22) PCT Filed: Aug. 18, 2016

(86) PCT No.: PCT/US2016/047622
§ 371 (c)(1),
(2) Date: Feb. 19, 2018

(87) PCT Pub. No.: WO2017/031354
PCT Pub. Date: Feb. 23, 2017

(65) Prior Publication Data
US 2019/0015561 A1  Jan. 17, 2019

Related U.S. Application Data

(60) Provisional application No. 62/206,637, filed on Aug. 18, 2015.

(51) Int. Cl.
*A61L 29/08* (2006.01)
*C23C 16/40* (2006.01)
(Continued)

(52) U.S. Cl.
CPC .............. *A61L 29/085* (2013.01); *A61L 27/34* (2013.01); *A61L 31/06* (2013.01); *C08L 83/04* (2013.01);
(Continued)

(58) Field of Classification Search
None
See application file for complete search history.

(56) References Cited

U.S. PATENT DOCUMENTS

| 3,274,267 A | 9/1966 | Chow |
| 3,297,465 A | 1/1967 | Connell |

(Continued)

FOREIGN PATENT DOCUMENTS

| AT | 414209 B | 10/2006 |
| AT | 504533 A1 | 6/2008 |

(Continued)

OTHER PUBLICATIONS

US 5,645,643 A, 07/1997, Thomas (withdrawn)
(Continued)

*Primary Examiner* — Matthew D Krcha
(74) *Attorney, Agent, or Firm* — G. Edward Cartier; SiO2 Medical Products, Inc.

(57) ABSTRACT

Processing an evacuated blood sample collection tube or other vessel by plasma enhanced chemical vapor deposition to apply a tie coating or layer (289), a barrier coating or layer (288), and optionally one or more additional coatings or layers. The tie coating or layer of SiOxCy is applied under partial vacuum and, while maintaining the partial vacuum unbroken in the lumen, the barrier coating or layer is applied. Then optionally, while maintaining the partial vacuum unbroken in the lumen, a pH protective coating or layer of SiOxCy can be applied. As a result of this processing, a coated vessel is produced having a lower gas perme- (Continued)

ation rate constant into the lumen than a corresponding vessel made by the same process except breaking the partial vacuum in the lumen between applying the tie coating or layer and applying the barrier coating or layer. Retention features are also described for keeping the vessels stoppered during exposure to reduced ambient pressure.

13 Claims, 5 Drawing Sheets

(51) Int. Cl.
    *C23C 16/515*     (2006.01)
    *A61L 31/06*     (2006.01)
    *C23C 16/30*     (2006.01)
    *C23C 16/04*     (2006.01)
    *A61L 27/34*     (2006.01)
    *C08L 83/04*     (2006.01)

(52) U.S. Cl.
    CPC ............ *C23C 16/045* (2013.01); *C23C 16/30* (2013.01); *C23C 16/401* (2013.01); *C23C 16/515* (2013.01)

(56) References Cited

U.S. PATENT DOCUMENTS

| | | |
|---|---|---|
| 3,355,947 A | 12/1967 | Karlby |
| 3,442,686 A | 5/1969 | Jones |
| 3,448,614 A | 6/1969 | Muger |
| 3,590,634 A | 7/1971 | Pasternak |
| 3,838,598 A | 10/1974 | Tomkins |
| 3,957,653 A | 5/1976 | Blecher |
| 4,111,326 A | 9/1978 | Percarpio |
| 4,134,832 A | 1/1979 | Heimreid |
| 4,136,794 A | 1/1979 | Percapio |
| 4,162,528 A | 7/1979 | Maldonado |
| 4,168,330 A | 9/1979 | Kaganowicz |
| 4,186,840 A | 2/1980 | Percarpio |
| 4,187,952 A | 2/1980 | Percarpio |
| 4,226,333 A | 10/1980 | Percarpio |
| 4,289,726 A | 9/1981 | Potoczky |
| 4,290,534 A | 9/1981 | Percarpio |
| 4,293,078 A | 10/1981 | Percarpio |
| 4,338,764 A | 7/1982 | Percarpio |
| 4,391,128 A | 7/1983 | McWorter |
| 4,392,218 A | 7/1983 | Plunkett, Jr. |
| 4,422,896 A | 12/1983 | Class |
| 4,452,679 A | 6/1984 | Dunn |
| 4,478,873 A | 10/1984 | Masso |
| 4,481,229 A | 11/1984 | Suzuki |
| 4,483,737 A | 11/1984 | Mantei |
| 4,484,479 A | 11/1984 | Eckhardt |
| 4,486,378 A | 12/1984 | Hirata |
| 4,522,510 A | 6/1985 | Rosencwaig |
| 4,524,089 A | 6/1985 | Hague |
| 4,524,616 A | 6/1985 | Drexel |
| 4,552,791 A | 11/1985 | Hahn |
| 4,576,204 A | 3/1986 | Smallborn |
| 4,609,428 A | 9/1986 | Fujimura |
| 4,610,770 A | 9/1986 | Saito |
| 4,648,107 A | 3/1987 | Latter |
| 4,648,281 A | 3/1987 | Morita |
| 4,652,429 A | 3/1987 | Konrad |
| 4,664,279 A | 5/1987 | Obrist |
| 4,667,620 A | 5/1987 | White |
| 4,668,365 A | 5/1987 | Foster |
| 4,683,838 A | 8/1987 | Kimura |
| 4,697,717 A | 10/1987 | Grippi |
| 4,703,187 A | 10/1987 | Hofling |
| 4,716,491 A | 12/1987 | Ohno |
| 4,721,553 A | 1/1988 | Saito |
| 4,725,481 A | 2/1988 | Ostapchenko |
| 4,741,446 A | 5/1988 | Miller |
| 4,756,964 A | 7/1988 | Kincaid |
| 4,767,414 A | 8/1988 | Williams |
| 4,778,721 A | 10/1988 | Sliemers |
| 4,799,246 A | 1/1989 | Fischer |
| 4,808,453 A | 2/1989 | Romberg |
| 4,809,876 A | 3/1989 | Tomaswick |
| 4,824,444 A | 4/1989 | Nomura |
| 4,841,776 A | 6/1989 | Kawachi |
| 4,842,704 A | 6/1989 | Collins |
| 4,844,986 A | 7/1989 | Karakelle |
| 4,846,101 A | 7/1989 | Montgomery |
| 4,853,102 A | 8/1989 | Tateishi |
| 4,869,203 A | 9/1989 | Pinkhasov |
| 4,872,758 A | 10/1989 | Miyazaki |
| 4,874,497 A | 10/1989 | Matsuoka |
| 4,880,675 A | 11/1989 | Mehta |
| 4,883,686 A | 11/1989 | Doehler |
| 4,886,086 A | 12/1989 | Etchells |
| 4,894,256 A | 1/1990 | Gartner |
| 4,894,510 A | 1/1990 | Nakanishi |
| 4,897,285 A | 1/1990 | Wilhelm |
| 4,926,791 A | 5/1990 | Hirose |
| 4,948,628 A | 8/1990 | Montgomery |
| 4,973,504 A | 11/1990 | Romberg |
| 4,991,104 A | 2/1991 | Miller |
| 4,999,014 A | 3/1991 | Gold |
| 5,000,994 A | 3/1991 | Romberg |
| 5,016,564 A | 5/1991 | Nakamura |
| 5,021,114 A | 6/1991 | Saito |
| 5,028,566 A | 7/1991 | Lagendijk |
| 5,030,475 A | 7/1991 | Ackermann |
| 5,032,202 A | 7/1991 | Tsai |
| 5,039,548 A | 8/1991 | Hirose |
| 5,041,303 A | 8/1991 | Wertheimer |
| 5,042,951 A | 8/1991 | Gold |
| 5,044,199 A | 9/1991 | Drexel |
| 5,064,083 A | 11/1991 | Alexander |
| 5,067,491 A | 11/1991 | Taylor |
| 5,079,481 A | 1/1992 | Moslehi |
| 5,082,542 A | 1/1992 | Moslehi |
| 5,084,356 A | 1/1992 | Deak |
| 5,085,904 A | 2/1992 | Deak |
| 5,099,881 A | 3/1992 | Nakajima |
| 5,113,790 A | 5/1992 | Geisler |
| 5,120,966 A | 6/1992 | Kondo |
| 5,131,752 A | 7/1992 | Yu |
| 5,144,196 A | 9/1992 | Gegenwart |
| 5,147,678 A | 9/1992 | Foerch |
| 5,154,943 A | 10/1992 | Etzkorn |
| 5,189,446 A | 2/1993 | Barnes |
| 5,192,849 A | 3/1993 | Moslehi |
| 5,198,725 A | 3/1993 | Chen |
| 5,203,959 A | 4/1993 | Hirose |
| 5,204,141 A | 4/1993 | Roberts |
| 5,209,882 A | 5/1993 | Hattori |
| 5,216,329 A | 6/1993 | Pelleteir |
| 5,224,441 A | 7/1993 | Felts |
| 5,225,024 A | 7/1993 | Hanley |
| 5,232,111 A | 8/1993 | Burns |
| 5,252,178 A | 10/1993 | Moslehi |
| 5,260,095 A | 11/1993 | Affinito |
| 5,266,398 A | 11/1993 | Hioki |
| 5,271,274 A | 12/1993 | Khuri-Yakub |
| 5,272,417 A | 12/1993 | Ohmi |
| 5,272,735 A | 12/1993 | Bryan |
| 5,275,299 A | 1/1994 | Konrad |
| 5,286,297 A | 2/1994 | Moslehi |
| 5,292,370 A | 3/1994 | Tsai |
| 5,294,011 A | 3/1994 | Konrad |
| 5,294,464 A | 3/1994 | Geisler |
| 5,297,561 A * | 3/1994 | Hulon ................ A61B 5/15003 215/355 |
| 5,298,587 A | 3/1994 | Hu |
| 5,300,901 A | 4/1994 | Krummel |
| 5,302,266 A | 4/1994 | Grabarz |
| 5,308,649 A | 5/1994 | Babacz |
| 5,314,561 A | 5/1994 | Komiya |
| 5,320,875 A | 6/1994 | Hu |
| 5,321,634 A | 6/1994 | Obata |

(56) References Cited

U.S. PATENT DOCUMENTS

| | | |
|---|---|---|
| 5,330,578 A | 7/1994 | Sakama |
| 5,333,049 A | 7/1994 | Ledger |
| 5,338,579 A | 8/1994 | Ogawa et al. |
| 5,346,579 A | 9/1994 | Cook |
| 5,354,286 A | 10/1994 | Mesa |
| 5,356,029 A | 10/1994 | Hogan |
| 5,361,921 A | 11/1994 | Burns |
| 5,364,665 A | 11/1994 | Felts |
| 5,364,666 A | 11/1994 | Williams |
| 5,372,851 A | 12/1994 | Ogawa et al. |
| 5,374,314 A | 12/1994 | Babacz |
| 5,378,510 A | 1/1995 | Thomas |
| 5,381,228 A | 1/1995 | Brace |
| 5,395,644 A | 3/1995 | Affinito |
| 5,396,080 A | 3/1995 | Hannotiau |
| 5,397,956 A | 3/1995 | Araki |
| 5,409,782 A | 4/1995 | Murayama |
| 5,413,813 A | 5/1995 | Cruse |
| 5,423,915 A | 6/1995 | Murata |
| 5,429,070 A | 7/1995 | Campbell |
| 5,433,786 A | 7/1995 | Hu |
| 5,434,008 A | 7/1995 | Felts |
| 5,439,736 A | 8/1995 | Nomura |
| 5,440,446 A | 8/1995 | Shaw |
| 5,443,645 A | 8/1995 | Otoshi |
| 5,444,207 A | 8/1995 | Sekine |
| 5,449,432 A | 9/1995 | Hanawa |
| 5,452,082 A | 9/1995 | Sanger |
| 5,468,520 A | 11/1995 | Williams |
| 5,470,388 A | 11/1995 | Goedicke |
| 5,472,660 A | 12/1995 | Fortin |
| 5,485,091 A | 1/1996 | Verkuil |
| 5,486,701 A | 1/1996 | Norton |
| 5,494,170 A | 2/1996 | Burns |
| 5,494,712 A | 2/1996 | Hu |
| 5,495,958 A | 3/1996 | Konrad |
| 5,508,075 A | 4/1996 | Roulin |
| 5,510,155 A | 4/1996 | Williams |
| 5,513,515 A | 5/1996 | Mayer |
| 5,514,276 A | 5/1996 | Babock |
| 5,521,351 A | 5/1996 | Mahoney |
| 5,522,518 A | 6/1996 | Konrad |
| 5,531,060 A | 7/1996 | Fayet |
| 5,531,683 A | 7/1996 | Kriesel |
| 5,536,253 A | 7/1996 | Haber |
| 5,543,919 A | 8/1996 | Mumola |
| 5,545,375 A | 8/1996 | Tropsha |
| 5,547,508 A | 8/1996 | Affinito |
| 5,547,723 A | 8/1996 | Williams |
| 5,554,223 A | 9/1996 | Imahashi |
| 5,555,471 A | 9/1996 | Xu |
| 5,565,248 A | 10/1996 | Piester |
| 5,569,810 A | 10/1996 | Tsuji |
| 5,571,366 A | 11/1996 | Ishii |
| 5,578,103 A | 11/1996 | Araujo |
| 5,591,898 A | 1/1997 | Mayer |
| 5,593,550 A | 1/1997 | Stewart |
| 5,597,456 A | 1/1997 | Maruyama |
| 5,616,369 A | 4/1997 | Williams |
| 5,620,523 A | 4/1997 | Maeda |
| 5,632,396 A | 5/1997 | Burns |
| 5,633,711 A | 5/1997 | Nelson |
| 5,643,638 A | 7/1997 | Otto |
| 5,652,030 A | 7/1997 | Delperier |
| 5,654,054 A | 8/1997 | Tropsha |
| 5,656,141 A | 8/1997 | Betz |
| 5,658,438 A | 8/1997 | Givens |
| 5,665,280 A | 9/1997 | Tropsha |
| 5,667,840 A | 9/1997 | Tingey |
| 5,674,321 A | 10/1997 | Pu |
| 5,677,010 A | 10/1997 | Esser |
| 5,679,412 A | 10/1997 | Kuehnle |
| 5,679,413 A | 10/1997 | Petrmichl |
| 5,683,771 A | 11/1997 | Tropsha |
| 5,686,157 A | 11/1997 | Harvey |
| 5,690,745 A | 11/1997 | Grunwald |
| 5,691,007 A | 11/1997 | Montgomery |
| 5,693,196 A | 12/1997 | Stewart |
| 5,699,923 A | 12/1997 | Burns |
| 5,702,770 A | 12/1997 | Martin |
| 5,704,983 A | 1/1998 | Thomas et al. |
| 5,716,683 A | 2/1998 | Harvey |
| 5,718,967 A | 2/1998 | Hu |
| 5,725,909 A | 3/1998 | Shaw |
| 5,733,405 A | 3/1998 | Taki |
| 5,736,207 A | 4/1998 | Walther |
| 5,737,179 A | 4/1998 | Shaw |
| 5,738,233 A | 4/1998 | Burns |
| 5,738,920 A | 4/1998 | Knors |
| 5,744,360 A | 4/1998 | Hu |
| 5,750,892 A | 5/1998 | Huang |
| 5,763,033 A | 6/1998 | Tropsha |
| 5,766,362 A | 6/1998 | Montgomery |
| 5,769,273 A | 6/1998 | Sasaki |
| 5,779,074 A | 7/1998 | Burns |
| 5,779,716 A | 7/1998 | Cano |
| 5,779,802 A | 7/1998 | Borghs |
| 5,779,849 A | 7/1998 | Blalock |
| 5,788,670 A | 8/1998 | Reinhard |
| 5,792,940 A | 8/1998 | Ghandhi |
| 5,798,027 A | 8/1998 | Lefebvre |
| 5,800,880 A | 9/1998 | Laurent |
| 5,807,343 A | 9/1998 | Tucker |
| 5,807,605 A | 9/1998 | Tingey |
| 5,812,261 A | 9/1998 | Nelson |
| 5,814,257 A | 9/1998 | Kawata |
| 5,814,738 A | 9/1998 | Pinkerton |
| 5,820,603 A | 10/1998 | Tucker |
| 5,823,373 A | 10/1998 | Sudo |
| 5,824,198 A | 10/1998 | Williams |
| 5,824,607 A | 10/1998 | Trow |
| 5,833,752 A | 11/1998 | Martin |
| 5,837,888 A | 11/1998 | Mayer |
| 5,837,903 A | 11/1998 | Weingand |
| 5,840,167 A | 11/1998 | Kim |
| 5,849,368 A | 12/1998 | Hostettler |
| 5,853,833 A | 12/1998 | Sudo |
| 5,855,686 A | 1/1999 | Rust |
| 5,861,546 A | 1/1999 | Sagi |
| 5,871,700 A | 2/1999 | Konrad |
| 5,877,895 A | 3/1999 | Shaw |
| 5,880,034 A | 3/1999 | Keller |
| 5,888,414 A | 3/1999 | Collins |
| 5,888,591 A | 3/1999 | Gleason |
| 5,897,508 A | 4/1999 | Konrad |
| 5,900,284 A | 5/1999 | Hu |
| 5,900,285 A | 5/1999 | Walther |
| 5,902,461 A | 5/1999 | Xu |
| 5,904,952 A | 5/1999 | Lopata |
| 5,913,140 A | 6/1999 | Roche |
| 5,914,189 A | 6/1999 | Hasz |
| 5,919,328 A | 7/1999 | Tropsha |
| 5,919,420 A | 7/1999 | Niermann |
| 5,935,391 A | 8/1999 | Nakahigashi |
| 5,945,187 A | 8/1999 | Buch-Rasmussen |
| 5,951,527 A | 9/1999 | Sudo |
| 5,952,069 A | 9/1999 | Tropsha |
| 5,955,161 A | 9/1999 | Tropsha |
| 5,961,911 A | 10/1999 | Hwang |
| 5,968,620 A | 10/1999 | Harvey |
| 5,972,297 A | 10/1999 | Niermann |
| 5,972,436 A | 10/1999 | Walther |
| 5,985,103 A | 11/1999 | Givens |
| 6,001,429 A | 12/1999 | Martin |
| 6,009,743 A | 1/2000 | Mayer |
| 6,013,337 A | 1/2000 | Knors |
| 6,017,317 A | 1/2000 | Newby |
| 6,018,987 A | 2/2000 | Mayer |
| 6,020,196 A | 2/2000 | Hu |
| 6,027,619 A | 2/2000 | Cathey |
| 6,032,813 A | 3/2000 | Niermann |
| 6,035,717 A | 3/2000 | Carodiskey |
| 6,050,400 A | 4/2000 | Taskis |
| 6,051,151 A | 4/2000 | Keller |

(56) References Cited

U.S. PATENT DOCUMENTS

| | | | |
|---|---|---|---|
| 6,054,016 | A | 4/2000 | Tuda |
| 6,054,188 | A | 4/2000 | Tropsha |
| 6,068,884 | A | 5/2000 | Rose |
| 6,077,403 | A | 6/2000 | Kobayashi |
| 6,081,330 | A | 6/2000 | Nelson |
| 6,082,295 | A | 7/2000 | Lee |
| 6,083,313 | A | 7/2000 | Venkatraman et al. |
| 6,085,927 | A | 7/2000 | Kusz |
| 6,090,081 | A | 7/2000 | Sudo |
| 6,106,678 | A | 8/2000 | Shufflebotham |
| 6,110,395 | A | 8/2000 | Gibson, Jr. |
| 6,110,544 | A | 8/2000 | Yang |
| 6,112,695 | A | 9/2000 | Felts |
| 6,116,081 | A | 9/2000 | Ghandhi |
| 6,117,243 | A | 9/2000 | Walther |
| 6,118,844 | A | 9/2000 | Fischer |
| 6,124,212 | A | 9/2000 | Fan |
| 6,125,687 | A | 10/2000 | McClelland |
| 6,126,640 | A | 10/2000 | Tucker |
| 6,136,275 | A | 10/2000 | Niermann |
| 6,139,802 | A | 10/2000 | Niermann |
| 6,143,140 | A | 11/2000 | Wang |
| 6,149,982 | A | 11/2000 | Plester |
| 6,153,269 | A | 11/2000 | Gleason |
| 6,156,152 | A | 12/2000 | Ogino |
| 6,156,399 | A | 12/2000 | Spallek |
| 6,156,435 | A | 12/2000 | Gleason |
| 6,160,350 | A | 12/2000 | Sakemi |
| 6,161,712 | A | 12/2000 | Savitz |
| 6,163,006 | A | 12/2000 | Doughty |
| 6,165,138 | A | 12/2000 | Miller |
| 6,165,542 | A | 12/2000 | Jaworowski |
| 6,165,566 | A | 12/2000 | Tropsha |
| 6,171,670 | B1 | 1/2001 | Sudo |
| 6,175,612 | B1 | 1/2001 | Sato |
| 6,177,142 | B1 | 1/2001 | Felts |
| 6,180,185 | B1 | 1/2001 | Felts |
| 6,180,191 | B1 | 1/2001 | Felts |
| 6,188,079 | B1 | 2/2001 | Juvinall |
| 6,189,484 | B1 | 2/2001 | Yin |
| 6,190,992 | B1 | 2/2001 | Sandhu |
| 6,193,853 | B1 | 2/2001 | Yumshtyk |
| 6,196,155 | B1 | 3/2001 | Setoyama |
| 6,197,166 | B1 | 3/2001 | Moslehi |
| 6,200,658 | B1 | 3/2001 | Walther |
| 6,200,675 | B1 | 3/2001 | Neerinck |
| 6,204,922 | B1 | 3/2001 | Chalmers |
| 6,210,791 | B1 | 4/2001 | Skoog |
| 6,213,985 | B1 | 4/2001 | Niedospial |
| 6,214,422 | B1 | 4/2001 | Yializis |
| 6,217,716 | B1 | 4/2001 | Fai Lai |
| 6,223,683 | B1 | 5/2001 | Plester |
| 6,236,459 | B1 | 5/2001 | Negahdaripour |
| 6,245,190 | B1 | 6/2001 | Masuda |
| 6,248,219 | B1 | 6/2001 | Wellerdieck |
| 6,248,397 | B1 | 6/2001 | Ye |
| 6,251,792 | B1 | 6/2001 | Collins |
| 6,254,983 | B1 | 7/2001 | Namiki |
| 6,261,643 | B1 | 7/2001 | Hasz |
| 6,263,249 | B1 | 7/2001 | Stewart |
| 6,271,047 | B1 | 8/2001 | Ushio |
| 6,276,296 | B1 | 8/2001 | Plester |
| 6,277,331 | B1 | 8/2001 | Konrad |
| 6,279,505 | B1 | 8/2001 | Plester |
| 6,284,986 | B1 | 9/2001 | Dietze |
| 6,306,132 | B1 | 10/2001 | Moorman |
| 6,308,556 | B1 | 10/2001 | Sagi |
| 6,322,661 | B1 | 11/2001 | Bailey, III |
| 6,331,174 | B1 | 12/2001 | Reinhard et al. |
| 6,346,596 | B1 | 2/2002 | Mallen |
| 6,348,967 | B1 | 2/2002 | Nelson |
| 6,350,415 | B1 | 2/2002 | Niermann |
| 6,351,075 | B1 | 2/2002 | Barankova |
| 6,352,629 | B1 | 3/2002 | Wang |
| 6,354,452 | B1 | 3/2002 | DeSalvo |
| 6,355,033 | B1 | 3/2002 | Moorman |
| 6,365,013 | B1 | 4/2002 | Beele |
| 6,375,022 | B1 | 4/2002 | Zurcher |
| 6,376,028 | B1 | 4/2002 | Laurent |
| 6,379,757 | B1 | 4/2002 | Iacovangelo |
| 6,382,441 | B1 | 5/2002 | Carano |
| 6,394,979 | B1 | 5/2002 | Sharp |
| 6,396,024 | B1 | 5/2002 | Doughty |
| 6,399,944 | B1 | 6/2002 | Vasilyev |
| 6,402,885 | B2 | 6/2002 | Loewenhardt |
| 6,410,926 | B1 | 6/2002 | Munro |
| 6,413,645 | B1 | 7/2002 | Graff |
| 6,432,494 | B1 | 8/2002 | Yang |
| 6,432,510 | B1 | 8/2002 | Kim |
| 6,470,650 | B1 | 10/2002 | Lohwasser |
| 6,471,822 | B1 | 10/2002 | Yin |
| 6,475,622 | B2 | 11/2002 | Namiki |
| 6,482,509 | B2 | 11/2002 | Buch-Rasmussen et al. |
| 6,486,081 | B1 | 11/2002 | Ishikawa |
| 6,500,500 | B1 | 12/2002 | Okamura |
| 6,503,579 | B1 | 1/2003 | Murakami |
| 6,518,195 | B1 | 2/2003 | Collins |
| 6,524,448 | B2 | 2/2003 | Brinkmann |
| 6,539,890 | B1 | 4/2003 | Felts |
| 6,544,610 | B1 | 4/2003 | Minami |
| 6,551,267 | B1 | 4/2003 | Cohen |
| 6,558,679 | B2 | 5/2003 | Flament-Garcia et al. |
| 6,562,189 | B1 | 5/2003 | Quiles |
| 6,565,791 | B1 | 5/2003 | Laurent |
| 6,582,426 | B2 | 6/2003 | Moorman |
| 6,582,823 | B1 | 6/2003 | Sakhrani et al. |
| 6,584,828 | B2 | 7/2003 | Sagi |
| 6,595,961 | B2 | 7/2003 | Hetzler |
| 6,597,193 | B2 | 7/2003 | Lagowski |
| 6,599,569 | B1 | 7/2003 | Humele |
| 6,599,594 | B1 | 7/2003 | Walther |
| 6,602,206 | B1 | 8/2003 | Niermann |
| 6,616,632 | B2 | 9/2003 | Sharp |
| 6,620,139 | B1 | 9/2003 | Plicchi |
| 6,620,334 | B2 | 9/2003 | Kanno |
| 6,623,861 | B2 | 9/2003 | Martin |
| 6,638,403 | B1 | 10/2003 | Inaba |
| 6,638,876 | B2 | 10/2003 | Levy |
| 6,645,354 | B1 | 11/2003 | Gorokhovsky |
| 6,651,835 | B2 | 11/2003 | Iskra |
| 6,652,520 | B2 | 11/2003 | Moorman |
| 6,656,540 | B2 | 12/2003 | Sakamoto |
| 6,658,919 | B2 | 12/2003 | Chatard |
| 6,662,957 | B2 | 12/2003 | Zurcher |
| 6,663,601 | B2 | 12/2003 | Hetzler |
| 6,670,200 | B2 | 12/2003 | Ushio |
| 6,673,199 | B1 | 1/2004 | Yamartino |
| 6,680,091 | B2 | 1/2004 | Buch-Rasmussen et al. |
| 6,680,621 | B2 | 1/2004 | Savtchouk |
| 6,683,308 | B2 | 1/2004 | Itagaki |
| 6,684,683 | B2 | 2/2004 | Potyrailo |
| 6,702,898 | B2 | 3/2004 | Hosoi |
| 6,706,412 | B2 | 3/2004 | Yializis |
| 6,746,430 | B2 | 6/2004 | Lubrecht |
| 6,749,078 | B2 | 6/2004 | Iskra |
| 6,752,899 | B1 | 6/2004 | Singh |
| 6,753,972 | B1 | 6/2004 | Hirose |
| 6,757,056 | B1 | 6/2004 | Meeks |
| 6,764,714 | B2 | 7/2004 | Wei |
| 6,765,466 | B2 | 7/2004 | Miyata |
| 6,766,682 | B2 | 7/2004 | Engle |
| 6,774,018 | B2 | 8/2004 | Mikhael |
| 6,796,780 | B1 | 9/2004 | Chatard |
| 6,800,852 | B2 | 10/2004 | Larson |
| 6,808,753 | B2 | 10/2004 | Rule |
| 6,810,106 | B2 | 10/2004 | Sato |
| 6,815,014 | B2 | 11/2004 | Gabelnick |
| 6,818,310 | B2 | 11/2004 | Namiki |
| 6,827,972 | B2 | 12/2004 | Darras |
| 6,837,954 | B2 | 1/2005 | Carano |
| 6,844,075 | B1 | 1/2005 | Saak |
| 6,853,141 | B2 | 2/2005 | Hoffman |
| 6,858,259 | B2 | 2/2005 | Affinito |
| 6,863,731 | B2 | 3/2005 | Elsayed-Ali |

(56) References Cited

U.S. PATENT DOCUMENTS

| | | |
|---|---|---|
| 6,864,773 B2 | 3/2005 | Perrin |
| 6,866,656 B2 | 3/2005 | Tingey |
| 6,872,428 B2 | 3/2005 | Yang |
| 6,876,154 B2 | 4/2005 | Appleyard |
| 6,885,727 B2 | 4/2005 | Tamura |
| 6,887,578 B2 | 5/2005 | Gleason |
| 6,891,158 B2 | 5/2005 | Larson |
| 6,892,567 B1 | 5/2005 | Morrow |
| 6,899,054 B1 | 5/2005 | Bardos |
| 6,905,769 B2 | 6/2005 | Komada |
| 6,910,597 B2 | 6/2005 | Iskra |
| 6,911,779 B2 | 6/2005 | Madocks |
| 6,919,107 B2 | 7/2005 | Schwarzenbach |
| 6,919,114 B1 | 7/2005 | Darras |
| 6,933,460 B2 | 8/2005 | Vanden Brande |
| 6,946,164 B2 | 9/2005 | Huang |
| 6,952,949 B2 | 10/2005 | Moore |
| 6,960,393 B2 | 11/2005 | Yializis |
| 6,962,671 B2 | 11/2005 | Martin |
| 6,965,221 B2 | 11/2005 | Lipcsei |
| 6,981,403 B2 | 1/2006 | Ascheman |
| 6,989,675 B2 | 1/2006 | Kesil |
| 6,995,377 B2 | 2/2006 | Darr |
| 7,029,755 B2 | 4/2006 | Terry |
| 7,029,803 B2 | 4/2006 | Becker |
| 7,039,158 B1 | 5/2006 | Janik |
| 7,052,736 B2 | 5/2006 | Wei |
| 7,052,920 B2 | 5/2006 | Ushio |
| 7,059,268 B2 | 6/2006 | Russell |
| 7,067,034 B2 | 6/2006 | Bailey, III |
| 7,074,501 B2 | 7/2006 | Czeremuszkin |
| 7,098,453 B2 | 8/2006 | Ando |
| 7,109,070 B2 | 9/2006 | Behle |
| 7,112,352 B2 | 9/2006 | Schaepkens |
| 7,112,541 B2 | 9/2006 | Xia |
| 7,115,310 B2 | 10/2006 | Jacoud |
| 7,118,538 B2 | 10/2006 | Konrad |
| 7,119,908 B2 | 10/2006 | Nomoto |
| 7,121,135 B2 | 10/2006 | Moore |
| 7,130,373 B2 | 10/2006 | Omote |
| 7,150,299 B2 | 12/2006 | Hertzler |
| 7,160,292 B2 | 1/2007 | Moorman |
| 7,180,849 B2 | 2/2007 | Hirokane |
| 7,183,197 B2 | 2/2007 | Won |
| 7,188,734 B2 | 3/2007 | Konrad |
| 7,189,218 B2 | 3/2007 | Lichtenberg |
| 7,189,290 B2 | 3/2007 | Hama |
| 7,193,724 B2 | 3/2007 | Isei |
| 7,198,685 B2 | 4/2007 | Hetzler |
| 7,206,074 B2 | 4/2007 | Fujimoto |
| 7,244,381 B2 | 7/2007 | Chatard |
| 7,253,892 B2 | 8/2007 | Semersky |
| 7,286,242 B2 | 10/2007 | Kim |
| 7,288,293 B2 | 10/2007 | Koulik |
| 7,297,216 B2 | 11/2007 | Hetzler |
| 7,297,640 B2 | 11/2007 | Xie |
| 7,300,684 B2 | 11/2007 | Boardman |
| 7,303,789 B2 | 12/2007 | Saito |
| 7,303,790 B2 | 12/2007 | Delaunay |
| 7,306,852 B2 | 12/2007 | Komada |
| 7,332,227 B2 | 2/2008 | Hardman |
| 7,338,576 B2 | 3/2008 | Ono |
| 7,339,682 B2 | 3/2008 | Aiyer |
| 7,344,766 B1 | 3/2008 | Sorensen |
| 7,348,055 B2 | 3/2008 | Chappa |
| 7,348,192 B2 | 3/2008 | Mikami |
| 7,362,425 B2 | 4/2008 | Meeks |
| 7,381,469 B2 | 6/2008 | Moelle |
| 7,390,573 B2 | 6/2008 | Korevaar |
| 7,399,500 B2 | 7/2008 | Bicker |
| 7,404,278 B2 | 7/2008 | Wittland |
| 7,405,008 B2 | 7/2008 | Domine |
| 7,409,313 B2 | 8/2008 | Ringermacher |
| 7,411,685 B2 | 8/2008 | Takashima |
| RE40,531 E | 10/2008 | Graff |
| 7,431,989 B2 | 10/2008 | Sakhrani |
| 7,438,783 B2 | 10/2008 | Miyata |
| 7,444,955 B2 | 11/2008 | Boardman |
| 7,455,892 B2 | 11/2008 | Goodwin |
| 7,480,363 B2 | 1/2009 | Lasiuk |
| 7,488,683 B2 | 2/2009 | Kobayashi |
| 7,494,941 B2 | 2/2009 | Kasahara |
| 7,507,378 B2 | 3/2009 | Reichenbach |
| 7,513,953 B1 | 4/2009 | Felts |
| 7,520,965 B2 | 4/2009 | Wei |
| 7,521,022 B2 | 4/2009 | Konrad |
| 7,534,615 B2 | 5/2009 | Havens |
| 7,534,733 B2 | 5/2009 | Bookbinder |
| RE40,787 E | 6/2009 | Martin |
| 7,541,069 B2 | 6/2009 | Tudhope |
| 7,552,620 B2 | 6/2009 | DeRoos |
| 7,553,529 B2 | 6/2009 | Sakhrani |
| 7,555,934 B2 | 7/2009 | DeRoos |
| 7,569,035 B1 | 8/2009 | Wilmot |
| 7,571,122 B2 | 8/2009 | Howes |
| 7,579,056 B2 | 8/2009 | Brown |
| 7,586,824 B2 | 8/2009 | Hirokane |
| 7,582,868 B2 | 9/2009 | Jiang |
| 7,595,097 B2 | 9/2009 | Iacovangelo |
| 7,608,151 B2 | 10/2009 | Tudhope |
| 7,609,605 B2 | 10/2009 | Hirokane |
| 7,618,686 B2 | 11/2009 | Colpo |
| 7,624,622 B1 | 12/2009 | Mayer |
| 7,625,494 B2 | 12/2009 | Honda |
| 7,641,636 B2 | 1/2010 | Moesli |
| 7,645,696 B1 | 1/2010 | Dulkin |
| 7,648,481 B2 | 1/2010 | Geiger |
| 7,682,816 B2 | 3/2010 | Kim |
| 7,694,403 B2 | 4/2010 | Moulton |
| 7,699,933 B2 | 4/2010 | Lizenberg |
| 7,704,683 B2 | 4/2010 | Wittenberg |
| 7,713,638 B2 | 5/2010 | Moelle |
| 7,736,689 B2 | 6/2010 | Chappa |
| 7,740,610 B2 | 6/2010 | Moh |
| 7,744,567 B2 | 6/2010 | Glowacki |
| 7,744,790 B2 | 6/2010 | Behle |
| 7,745,228 B2 | 6/2010 | Schwind |
| 7,745,547 B1 | 6/2010 | Auerbach |
| 7,749,914 B2 | 7/2010 | Honda |
| 7,754,302 B2 | 7/2010 | Yamaski |
| 7,766,882 B2 | 8/2010 | Sudo |
| 7,780,866 B2 | 8/2010 | Miller |
| 7,785,862 B2 | 8/2010 | Kim |
| 7,790,475 B2 | 9/2010 | Galbraith |
| 7,798,993 B2 | 9/2010 | Lim |
| 7,803,305 B2 | 9/2010 | Ahem |
| 7,807,242 B2 | 10/2010 | Sorensen |
| 7,815,922 B2 | 10/2010 | Chaney |
| 7,846,293 B2 | 12/2010 | Iwasaki |
| 7,854,889 B2 | 12/2010 | Perot |
| 7,867,366 B1 | 1/2011 | McFarland |
| 7,901,783 B2 | 3/2011 | Rose |
| 7,905,866 B2 | 3/2011 | Haider |
| 7,922,880 B1 | 4/2011 | Pradhan |
| 7,922,958 B2 | 4/2011 | D'Arrigo |
| 7,931,955 B2 | 4/2011 | Behle |
| 7,932,678 B2 | 4/2011 | Madocks |
| 7,934,613 B2 | 5/2011 | Sudo |
| 7,943,205 B2 | 5/2011 | Schaepkens |
| 7,947,337 B2 | 5/2011 | Kuepper |
| 7,955,986 B2 | 6/2011 | Hoffman |
| 7,960,043 B2 | 6/2011 | Harris |
| 7,964,438 B2 | 6/2011 | Roca I Cabarrocas |
| 7,967,945 B2 | 6/2011 | Glukhoy |
| 7,975,646 B2 | 7/2011 | Rius |
| 7,985,188 B2 | 7/2011 | Felts |
| 8,025,915 B2 | 9/2011 | Haines |
| 3,039,524 A1 | 10/2011 | Chappa |
| 8,038,858 B1 | 10/2011 | Bures |
| 8,056,719 B2 | 11/2011 | Porret |
| 8,062,266 B2 | 11/2011 | McKinnon |
| 8,066,854 B2 | 11/2011 | Storey |
| 8,070,917 B2 | 12/2011 | Tsukamoto |
| 8,075,995 B2 | 12/2011 | Zhao |

(56) References Cited

U.S. PATENT DOCUMENTS

| | | |
|---|---|---|
| 8,092,605 B2 | 1/2012 | Shannon |
| 8,101,246 B2 | 1/2012 | Fayet |
| 8,197,452 B2 | 6/2012 | Harding |
| 8,277,025 B2 | 7/2012 | Lewis |
| 8,258,486 B2 | 9/2012 | Avnery |
| 8,268,410 B2 | 9/2012 | Moelle |
| 8,273,222 B2 | 9/2012 | Wei |
| 8,313,455 B2 | 11/2012 | DiGregorio |
| 8,323,166 B2 | 12/2012 | Haines |
| 8,389,958 B2 | 3/2013 | Vo-Dinh |
| 8,397,667 B2 | 3/2013 | Behle |
| 8,409,441 B2 | 4/2013 | Wilt |
| 8,418,650 B2 | 4/2013 | Goto |
| 8,435,605 B2 | 5/2013 | Aitken et al. |
| 8,475,886 B2 | 7/2013 | Chen et al. |
| 8,512,796 B2 | 8/2013 | Felts |
| 8,524,331 B2 | 9/2013 | Honda |
| 8,592,015 B2 | 11/2013 | Bicker |
| 8,603,638 B2 | 12/2013 | Liu |
| 8,618,509 B2 | 12/2013 | Vo-Dinh |
| 8,623,324 B2 | 1/2014 | Diwu |
| 8,633,034 B2 | 1/2014 | Trotter |
| 8,747,962 B2 | 6/2014 | Bicker |
| 8,802,603 B2 | 8/2014 | D'Souza |
| 8,816,022 B2 | 8/2014 | Zhao |
| 9,068,565 B2 | 6/2015 | Alarcon |
| 2001/0000279 A1 | 4/2001 | Daniels |
| 2001/0021356 A1 | 9/2001 | Konrad |
| 2001/0038894 A1 | 11/2001 | Komada |
| 2001/0042510 A1 | 11/2001 | Plester |
| 2001/0043997 A1 | 11/2001 | Uddin |
| 2002/0006487 A1 | 1/2002 | O'Connor |
| 2002/0007796 A1 | 1/2002 | Gorokhovsky |
| 2002/0070647 A1 | 6/2002 | Ginovker |
| 2002/0117114 A1 | 8/2002 | Ikenaga |
| 2002/0125900 A1 | 9/2002 | Savtchouk |
| 2002/0130100 A1 | 9/2002 | Smith |
| 2002/0130674 A1 | 9/2002 | Logowski |
| 2002/0141477 A1 | 10/2002 | Akahori |
| 2002/0153103 A1 | 10/2002 | Madocks |
| 2002/0155218 A1 | 10/2002 | Meyer |
| 2002/0170495 A1 | 11/2002 | Nakamura |
| 2002/0176947 A1 | 11/2002 | Darras |
| 2002/0182101 A1 | 12/2002 | Koulik |
| 2002/0185226 A1 | 12/2002 | Lea |
| 2002/0190207 A1 | 12/2002 | Levy |
| 2003/0010454 A1 | 1/2003 | Bailey, III |
| 2003/0013818 A1 | 1/2003 | Hakuta |
| 2003/0029837 A1 | 2/2003 | Trow |
| 2003/0031806 A1 | 2/2003 | Jinks |
| 2003/0046982 A1 | 3/2003 | Chartard |
| 2003/0058413 A1 | 3/2003 | Bamhurst |
| 2003/0102087 A1 | 6/2003 | Ito |
| 2003/0119193 A1 | 6/2003 | Hess |
| 2003/0148028 A1 | 8/2003 | Kimura et al. |
| 2003/0159654 A1 | 8/2003 | Arnold |
| 2003/0215652 A1 | 11/2003 | O'Connor |
| 2003/0219547 A1 | 11/2003 | Arnold |
| 2003/0232150 A1 | 12/2003 | Arnold |
| 2004/0024371 A1 | 2/2004 | Plicchi |
| 2004/0039401 A1 | 2/2004 | Chow |
| 2004/0040372 A1 | 3/2004 | Plester |
| 2004/0045811 A1 | 3/2004 | Wang |
| 2004/0050744 A1 | 3/2004 | Hama |
| 2004/0055538 A1 | 3/2004 | Gorokhovsky |
| 2004/0071960 A1 | 4/2004 | Weber |
| 2004/0082917 A1 | 4/2004 | Etzler |
| 2004/0084151 A1 | 5/2004 | Kim |
| 2004/0125913 A1 | 7/2004 | Larson |
| 2004/0135081 A1 | 7/2004 | Larson |
| 2004/0149225 A1 | 8/2004 | Weikart |
| 2004/0175961 A1 | 9/2004 | Olsen |
| 2004/0177676 A1 | 9/2004 | Moore |
| 2004/0195960 A1 | 10/2004 | Czeremuszkin |
| 2004/0206309 A1 | 10/2004 | Bera |
| 2004/0217046 A1* | 11/2004 | Konrad .............. G01N 33/491 210/321.6 |
| 2004/0217081 A1 | 11/2004 | Konrad |
| 2004/0247948 A1 | 12/2004 | Behle |
| 2004/0267194 A1 | 12/2004 | Sano |
| 2005/0000962 A1 | 1/2005 | Crawford |
| 2005/0010175 A1 | 1/2005 | Beedon |
| 2005/0019503 A1 | 1/2005 | Komada |
| 2005/0037165 A1 | 2/2005 | Ahem |
| 2005/0039854 A1 | 2/2005 | Matsuyama |
| 2005/0045472 A1 | 3/2005 | Nagata |
| 2005/0057754 A1 | 3/2005 | Smith |
| 2005/0073323 A1 | 4/2005 | Kohno |
| 2005/0075611 A1 | 4/2005 | Heltzer |
| 2005/0075612 A1 | 4/2005 | Lee |
| 2005/0161149 A1 | 7/2005 | Yokota |
| 2005/0169803 A1 | 8/2005 | Betz |
| 2005/0190450 A1 | 9/2005 | Becker |
| 2005/0196629 A1 | 9/2005 | Bariatinsky |
| 2005/0199571 A1 | 9/2005 | Geisler |
| 2005/0206907 A1 | 9/2005 | Fujimoto |
| 2005/0211383 A1 | 9/2005 | Miyata |
| 2005/0223988 A1 | 10/2005 | Behle |
| 2005/0227002 A1 | 10/2005 | Lizenberg |
| 2005/0227022 A1 | 10/2005 | Domine |
| 2005/0229850 A1 | 10/2005 | Behle |
| 2005/0233077 A1 | 10/2005 | Lizenberg |
| 2005/0233091 A1 | 10/2005 | Kumar |
| 2005/0236346 A1 | 10/2005 | Whitney |
| 2005/0260504 A1 | 11/2005 | Becker |
| 2005/0284550 A1 | 12/2005 | Bicker |
| 2006/0005608 A1 | 1/2006 | Kutzhoffer |
| 2006/0013997 A1 | 1/2006 | Kuepper |
| 2006/0014309 A1 | 1/2006 | Sachdev |
| 2006/0024849 A1 | 2/2006 | Zhu |
| 2006/0042755 A1 | 3/2006 | Holmberg |
| 2006/0046006 A1 | 3/2006 | Bastion |
| 2006/0051252 A1 | 3/2006 | Yuan |
| 2006/0051520 A1 | 3/2006 | Behle |
| 2006/0076231 A1 | 4/2006 | Wei |
| 2006/0086320 A1 | 4/2006 | Lizenberg |
| 2006/0099340 A1 | 5/2006 | Behle |
| 2006/0121222 A1 | 6/2006 | Audrich |
| 2006/0121613 A1 | 6/2006 | Havens |
| 2006/0121623 A1 | 6/2006 | He |
| 2006/0127699 A1 | 6/2006 | Moelle |
| 2006/0135945 A1 | 6/2006 | Bankiewicz |
| 2006/0138326 A1 | 6/2006 | Jiang |
| 2006/0150909 A1 | 7/2006 | Behle |
| 2006/0169026 A1 | 8/2006 | Kage |
| 2006/0178627 A1 | 8/2006 | Geiger |
| 2006/0183345 A1 | 8/2006 | Nguyen |
| 2006/0192973 A1 | 8/2006 | Aiyer |
| 2006/0196419 A1 | 9/2006 | Tudhope |
| 2006/0198903 A1 | 9/2006 | Storey |
| 2006/0198965 A1 | 9/2006 | Tudhope |
| 2006/0200078 A1 | 9/2006 | Konrad |
| 2006/0200084 A1 | 9/2006 | Ito |
| 2006/0210425 A1 | 9/2006 | Mirkarimi |
| 2006/0228497 A1 | 10/2006 | Kumar |
| 2006/0260360 A1 | 11/2006 | Dick |
| 2007/0003441 A1 | 1/2007 | Wohleb |
| 2007/0009673 A1 | 1/2007 | Fukazawa et al. |
| 2007/0017870 A1 | 1/2007 | Belov |
| 2007/0048456 A1 | 3/2007 | Keshner |
| 2007/0049048 A1 | 3/2007 | Rauf |
| 2007/0051629 A1 | 3/2007 | Donlik |
| 2007/0065680 A1 | 3/2007 | Schultheis |
| 2007/0076833 A1 | 4/2007 | Becker |
| 2007/0102344 A1 | 5/2007 | Konrad |
| 2007/0123920 A1 | 5/2007 | Inokuti |
| 2007/0148326 A1 | 6/2007 | Hastings |
| 2007/0166187 A1 | 7/2007 | Song |
| 2007/0184657 A1 | 8/2007 | Iijima |
| 2007/0187229 A1 | 8/2007 | Aksenov |
| 2007/0187280 A1 | 8/2007 | Haines |
| 2007/0205096 A1 | 9/2007 | Nagashima |
| 2007/0215009 A1 | 9/2007 | Shimazu |
| 2007/0215046 A1 | 9/2007 | Lupke |

(56) References Cited

U.S. PATENT DOCUMENTS

| | | |
|---|---|---|
| 2007/0218265 A1 | 9/2007 | Harris |
| 2007/0224236 A1 | 9/2007 | Boden |
| 2007/0229844 A1 | 10/2007 | Holz |
| 2007/0231655 A1 | 10/2007 | Ha |
| 2007/0232066 A1 | 10/2007 | Bicker |
| 2007/0235890 A1 | 10/2007 | Lewis |
| 2007/0243618 A1 | 10/2007 | Hatchett |
| 2007/0251458 A1 | 11/2007 | Mund |
| 2007/0258894 A1 | 11/2007 | Melker et al. |
| 2007/0259184 A1 | 11/2007 | Martin |
| 2007/0281108 A1 | 12/2007 | Weikart |
| 2007/0281117 A1 | 12/2007 | Kaplan |
| 2007/0287950 A1 | 12/2007 | Kjeken |
| 2007/0287954 A1 | 12/2007 | Zhao |
| 2007/0298189 A1 | 12/2007 | Straemke |
| 2008/0011232 A1 | 1/2008 | Ruis |
| 2008/0017113 A1 | 1/2008 | Goto |
| 2008/0023414 A1 | 1/2008 | Konrad |
| 2008/0027400 A1 | 1/2008 | Harding |
| 2008/0045880 A1 | 2/2008 | Kjeken |
| 2008/0050567 A1 | 2/2008 | Kawashima |
| 2008/0050932 A1 | 2/2008 | Lakshmanan |
| 2008/0053373 A1 | 3/2008 | Mund |
| 2008/0069970 A1 | 3/2008 | Wu |
| 2008/0071228 A1 | 3/2008 | Wu |
| 2008/0081184 A1 | 4/2008 | Kubo |
| 2008/0090039 A1 | 4/2008 | Klein |
| 2008/0093245 A1 | 4/2008 | Periasamy |
| 2008/0102206 A1 | 5/2008 | Wagner |
| 2008/0109017 A1 | 5/2008 | Herweck |
| 2008/0110852 A1 | 5/2008 | Kuroda |
| 2008/0113109 A1 | 5/2008 | Moelle |
| 2008/0118734 A1 | 5/2008 | Goodwin |
| 2008/0131628 A1 | 6/2008 | Abensour |
| 2008/0131638 A1 | 6/2008 | Hutton |
| 2008/0139003 A1 | 6/2008 | Pirzada |
| 2008/0144185 A1 | 6/2008 | Wang et al. |
| 2008/0145271 A1 | 6/2008 | Kidambi |
| 2008/0187681 A1 | 8/2008 | Hofrichter |
| 2008/0202414 A1 | 8/2008 | Yan |
| 2008/0206477 A1 | 8/2008 | Leontaris |
| 2008/0210550 A1 | 9/2008 | Walther |
| 2008/0220164 A1 | 9/2008 | Bauch |
| 2008/0223815 A1 | 9/2008 | Konrad |
| 2008/0233355 A1 | 9/2008 | Henze |
| 2008/0260966 A1 | 10/2008 | Hanawa |
| 2008/0277332 A1 | 11/2008 | Liu |
| 2008/0289957 A1 | 11/2008 | Takigawa |
| 2008/0292806 A1 | 11/2008 | Wei |
| 2008/0295772 A1 | 12/2008 | Park |
| 2008/0303131 A1 | 12/2008 | McElrea |
| 2008/0312607 A1 | 12/2008 | Delmotte |
| 2008/0314318 A1 | 12/2008 | Han |
| 2009/0004091 A1 | 1/2009 | Kang |
| 2009/0004363 A1 | 1/2009 | Keshner |
| 2009/0017217 A1 | 1/2009 | Hass |
| 2009/0022981 A1 | 1/2009 | Yoshida |
| 2009/0029402 A1 | 1/2009 | Papkovsky |
| 2009/0031953 A1 | 2/2009 | Ingle |
| 2009/0032393 A1 | 2/2009 | Madocks |
| 2009/0039240 A1 | 2/2009 | Van Nijnatten |
| 2009/0053491 A1 | 2/2009 | Laboda |
| 2009/0061237 A1 | 3/2009 | Gates |
| 2009/0065485 A1 | 3/2009 | O'Neill |
| 2009/0069790 A1 | 3/2009 | Yokley |
| 2009/0081797 A1 | 3/2009 | Fadeev |
| 2009/0099512 A1 | 4/2009 | Digregorio |
| 2009/0104392 A1 | 4/2009 | Takada |
| 2009/0117268 A1 | 5/2009 | Lewis |
| 2009/0117389 A1 | 5/2009 | Amberg-Schwab |
| 2009/0122832 A1 | 5/2009 | Feist |
| 2009/0134884 A1 | 5/2009 | Bosselmann |
| 2009/0137966 A1 | 5/2009 | Rueckert |
| 2009/0142227 A1 | 6/2009 | Fuchs |
| 2009/0142514 A1 | 6/2009 | O'Neill |
| 2009/0147719 A1 | 6/2009 | Rak |
| 2009/0149816 A1 | 6/2009 | Hetzler |
| 2009/0155490 A1 | 6/2009 | Bicker |
| 2009/0162571 A1 | 6/2009 | Haines |
| 2009/0166312 A1 | 7/2009 | Giraud |
| 2009/0176031 A1 | 7/2009 | Armellin |
| 2009/0214801 A1 | 8/2009 | Higashi |
| 2009/0220948 A1 | 9/2009 | Oviso et al. |
| 2009/0263668 A1 | 10/2009 | David |
| 2009/0274851 A1 | 11/2009 | Goudar |
| 2009/0280268 A1 | 11/2009 | Glukhoy |
| 2009/0297730 A1 | 12/2009 | Glukhoy |
| 2009/0306595 A1 | 12/2009 | Shih |
| 2009/0326517 A1 | 12/2009 | Bork |
| 2010/0021998 A1 | 1/2010 | Sanyal |
| 2010/0028238 A1 | 2/2010 | Maschwitz |
| 2010/0034985 A1 | 2/2010 | Krueger |
| 2010/0075077 A1 | 3/2010 | Bicker et al. |
| 2010/0086808 A1 | 4/2010 | Nagata |
| 2010/0089097 A1 | 4/2010 | Brack |
| 2010/0104770 A1 | 4/2010 | Goudar |
| 2010/0105208 A1 | 4/2010 | Winniczek |
| 2010/0132762 A1 | 6/2010 | Graham, Jr. |
| 2010/0145284 A1 | 6/2010 | Togashi |
| 2010/0149540 A1 | 6/2010 | Boukherroub |
| 2010/0174239 A1 | 7/2010 | Yodfat |
| 2010/0174245 A1 | 7/2010 | Halverson |
| 2010/0178490 A1 | 7/2010 | Cerny |
| 2010/0186740 A1 | 7/2010 | Lewis |
| 2010/0190036 A1 | 7/2010 | Komvopoulos |
| 2010/0193461 A1 | 8/2010 | Boutroy |
| 2010/0195471 A1 | 8/2010 | Hirokane |
| 2010/0204648 A1 | 8/2010 | Stout |
| 2010/0230281 A1 | 9/2010 | Park |
| 2010/0231194 A1 | 9/2010 | Bauch |
| 2010/0237545 A1 | 9/2010 | Haury |
| 2010/0273261 A1 | 10/2010 | Chen |
| 2010/0275847 A1 | 11/2010 | Yamasaki |
| 2010/0279397 A1 | 11/2010 | Crawford |
| 2010/0298738 A1* | 11/2010 | Felts .............. C23C 16/54 600/576 |
| 2010/0298779 A1 | 11/2010 | Hetzler |
| 2011/0037159 A1 | 2/2011 | McElrea |
| 2011/0046570 A1 | 2/2011 | Stout |
| 2011/0056912 A1 | 3/2011 | Magsuyama |
| 2011/0065798 A1 | 3/2011 | Hoang |
| 2011/0079582 A1 | 4/2011 | Yonesu |
| 2011/0093056 A1 | 4/2011 | Kaplan |
| 2011/0111132 A1 | 5/2011 | Wei |
| 2011/0117202 A1 | 5/2011 | Bourke, Jr. |
| 2011/0117288 A1 | 5/2011 | Honda |
| 2011/0137263 A1 | 6/2011 | Ashmead |
| 2011/0152820 A1 | 6/2011 | Chattaraj |
| 2011/0159101 A1 | 6/2011 | Kurdyumov et al. |
| 2011/0160662 A1 | 6/2011 | Stout |
| 2011/0160663 A1 | 6/2011 | Stout |
| 2011/0174220 A1 | 7/2011 | Laure |
| 2011/0186537 A1 | 8/2011 | Rodriguez San Juan et al. |
| 2011/0220490 A1 | 9/2011 | Wei |
| 2011/0253674 A1 | 10/2011 | Chung |
| 2011/0313363 A1 | 12/2011 | D'Souza et al. |
| 2011/0319758 A1 | 12/2011 | Wang |
| 2011/0319813 A1 | 12/2011 | Kamen |
| 2012/0003497 A1 | 1/2012 | Handy |
| 2012/0004339 A1 | 1/2012 | Chappa |
| 2012/0021136 A1 | 1/2012 | Dzengeleski |
| 2012/0031070 A1 | 2/2012 | Slough |
| 2012/0035543 A1 | 2/2012 | Kamen |
| 2012/0052123 A9 | 3/2012 | Kurdyumov et al. |
| 2012/0053530 A1 | 3/2012 | Zhao |
| 2012/0058351 A1 | 3/2012 | Zhao |
| 2012/0065612 A1 | 3/2012 | Stout |
| 2012/0097527 A1 | 4/2012 | Kodaira |
| 2012/0097870 A1 | 4/2012 | Leray |
| 2012/0108058 A1 | 5/2012 | Ha |
| 2012/0123345 A1 | 5/2012 | Felts |
| 2012/0141913 A1 | 6/2012 | Lee |
| 2012/0143148 A1 | 6/2012 | Zhao |
| 2012/0149871 A1 | 6/2012 | Saxena |

(56) References Cited

U.S. PATENT DOCUMENTS

| | | |
|---|---|---|
| 2012/0171386 A1 | 7/2012 | Bicker |
| 2012/0175384 A1 | 7/2012 | Greter |
| 2012/0183954 A1 | 7/2012 | Diwu |
| 2012/0205374 A1 | 8/2012 | Klumpen |
| 2012/0231182 A1 | 9/2012 | Stevens |
| 2012/0234720 A1 | 9/2012 | Digregorio |
| 2012/0252709 A1 | 10/2012 | Felts |
| 2013/0041241 A1 | 2/2013 | Felts |
| 2013/0046375 A1 | 2/2013 | Chen |
| 2013/0057677 A1 | 3/2013 | Weil |
| 2013/0072025 A1 | 3/2013 | Singh |
| 2013/0081953 A1 | 4/2013 | Bruna et al. |
| 2013/0190695 A1 | 7/2013 | Wu |
| 2013/0209704 A1 | 8/2013 | Krueger |
| 2013/0264303 A1 | 10/2013 | Andersen |
| 2013/0296235 A1 | 11/2013 | Alarcon |
| 2014/0010969 A1 | 1/2014 | Bicker |
| 2014/0052076 A1 | 2/2014 | Zhao |
| 2014/0054803 A1 | 2/2014 | Chen |
| 2014/0099455 A1 | 4/2014 | Stanley |
| 2014/0110297 A1 | 4/2014 | Trotter |
| 2014/0147654 A1 | 5/2014 | Walther |
| 2014/0151320 A1 | 6/2014 | Chang |
| 2014/0151370 A1 | 6/2014 | Chang |
| 2014/0187666 A1 | 7/2014 | Aizenberg |
| 2014/0190846 A1 | 7/2014 | Belt |
| 2014/0221934 A1 | 8/2014 | Janvier |
| 2014/0251856 A1 | 9/2014 | Larsson |
| 2014/0251859 A1 | 9/2014 | Weikart et al. |
| 2014/0305830 A1 | 10/2014 | Bicker |
| 2015/0165125 A1 | 6/2015 | Foucher |
| 2015/0224263 A1 | 8/2015 | Dugand |
| 2016/0186009 A1 | 6/2016 | Goto |

FOREIGN PATENT DOCUMENTS

| | | |
|---|---|---|
| AU | 2002354470 B2 | 5/2007 |
| CA | 2085805 | 12/1992 |
| CA | 2277679 A1 | 7/1997 |
| CA | 2355681 | 7/2000 |
| CA | 2571380 A1 | 7/2006 |
| CA | 2718253 | 9/2009 |
| CA | 2268719 C | 8/2010 |
| CA | 2879732 A1 | 1/2014 |
| CN | 1245439 A | 2/2000 |
| CN | 2546041 Y | 4/2003 |
| CN | 1436104 A | 8/2003 |
| CN | 1639775 A | 7/2005 |
| CN | 1711310 A | 12/2005 |
| CN | 2766863 Y | 3/2006 |
| CN | 1898172 A | 1/2007 |
| CN | 101035630 A | 9/2007 |
| CN | 201002786 Y | 1/2008 |
| CN | 101147813 A | 3/2008 |
| CN | 201056331 Y | 5/2008 |
| CN | 102027159 A | 4/2011 |
| CN | 102036814 A | 4/2011 |
| CN | 102414343 A | 4/2012 |
| CN | 102581274 A | 7/2012 |
| CN | 102917805 A | 2/2013 |
| DE | 1147836 | 4/1969 |
| DE | 1147838 | 4/1969 |
| DE | 3632748 A1 | 4/1988 |
| DE | 3908418 A1 | 9/1990 |
| DE | 4214401 C1 | 3/1993 |
| DE | 4204082 A1 | 8/1993 |
| DE | 4316349 A1 | 11/1994 |
| DE | 4438359 | 5/1996 |
| DE | 19707645 A1 | 8/1998 |
| DE | 19830794 A1 | 1/2000 |
| DE | 19912737 A1 | 6/2000 |
| DE | 10010831 A1 | 9/2001 |
| DE | 10154404 C1 | 6/2003 |
| DE | 10201110 A1 | 10/2003 |
| DE | 10242698 | 3/2004 |
| DE | 10246181 A1 | 4/2004 |
| DE | 10353540 A1 | 5/2004 |
| DE | 102004017236 A1 | 10/2005 |
| DE | 102006061585 A1 | 2/2008 |
| DE | 102008023027 A1 | 11/2009 |
| EP | 0121340 A2 | 10/1984 |
| EP | 0221005 A2 | 5/1987 |
| EP | 0275965 A2 | 7/1988 |
| EP | 0284867 A2 | 10/1988 |
| EP | 0306307 | 3/1989 |
| EP | 0329041 A2 | 8/1989 |
| EP | 0343017 A2 | 11/1989 |
| EP | 0396919 A2 | 11/1990 |
| EP | 0482613 A1 | 10/1991 |
| EP | 0484746 A2 | 10/1991 |
| EP | 0495447 A1 | 7/1992 |
| EP | 0520519 A1 | 12/1992 |
| EP | 0535810 A1 | 4/1993 |
| EP | 0375778 B1 | 9/1993 |
| EP | 0571116 A1 | 11/1993 |
| EP | 0580094 A1 | 1/1994 |
| EP | 0603717 A2 | 6/1994 |
| EP | 0619178 | 10/1994 |
| EP | 0645470 A1 | 3/1995 |
| EP | 0697378 A2 | 2/1996 |
| EP | 0709485 B1 | 5/1996 |
| EP | 0719877 A1 | 7/1996 |
| EP | 0728676 A1 | 8/1996 |
| EP | 0787824 A2 | 8/1997 |
| EP | 0787828 A2 | 8/1997 |
| EP | 0814114 A1 | 12/1997 |
| EP | 0251812 A2 | 1/1998 |
| EP | 0833366 A2 | 4/1998 |
| EP | 0879611 A2 | 11/1998 |
| EP | 0940183 A2 | 9/1999 |
| EP | 0962229 A2 | 12/1999 |
| EP | 0992610 A2 | 4/2000 |
| EP | 1119034 A1 | 7/2001 |
| EP | 0954272 B1 | 3/2002 |
| EP | 1245694 A1 | 10/2002 |
| EP | 1388594 B1 | 1/2003 |
| EP | 1317937 A1 | 6/2003 |
| EP | 1365043 A1 | 11/2003 |
| EP | 1367145 | 12/2003 |
| EP | 1388593 A1 | 2/2004 |
| EP | 1439241 A2 | 7/2004 |
| EP | 1447459 A2 | 8/2004 |
| EP | 1990639 A1 | 2/2005 |
| EP | 1510595 A1 | 3/2005 |
| EP | 1522403 A2 | 4/2005 |
| EP | 1901067 A2 | 8/2005 |
| EP | 1507894 | 12/2005 |
| EP | 1507723 | 3/2006 |
| EP | 1653192 A1 | 5/2006 |
| EP | 1810758 A1 | 7/2007 |
| EP | 1356260 B1 | 12/2007 |
| EP | 1870117 A2 | 12/2007 |
| EP | 1881088 A1 | 1/2008 |
| EP | 1507887 | 7/2008 |
| EP | 1415018 | 10/2008 |
| EP | 1756565 A4 | 7/2009 |
| EP | 2199264 A1 | 11/2009 |
| EP | 1388594 B1 | 1/2010 |
| EP | 2178109 A1 | 4/2010 |
| EP | 1507895 | 7/2010 |
| EP | 2218465 A1 | 8/2010 |
| EP | 2243751 A1 | 10/2010 |
| EP | 2251671 | 11/2010 |
| EP | 2261185 | 12/2010 |
| EP | 2369038 A2 | 9/2011 |
| EP | 1960279 B1 | 10/2011 |
| EP | 2444771 A2 | 4/2012 |
| EP | 2602354 A1 | 6/2013 |
| EP | 2639330 A1 | 9/2013 |
| FR | 891892 A | 11/1942 |
| GB | 752822 | 7/1956 |
| GB | 1363762 | 8/1974 |
| GB | 1513426 A | 6/1978 |
| GB | 1566251 | 4/1980 |

(56) References Cited

FOREIGN PATENT DOCUMENTS

| | | |
|---|---|---|
| GB | 2210826 A | 6/1989 |
| GB | 2231197 A | 11/1990 |
| GB | 2246794 A | 2/1992 |
| GB | 2246795 A | 2/1992 |
| GB | 2387964 A | 10/2003 |
| JP | 56027330 A | 3/1981 |
| JP | 58154602 A | 9/1983 |
| JP | 59087307 A | 5/1984 |
| JP | 59154029 | 9/1984 |
| JP | S61183462 A | 8/1986 |
| JP | S62180069 A | 8/1987 |
| JP | S62290866 A | 12/1987 |
| JP | 63124521 A2 | 5/1988 |
| JP | 1023105 A | 1/1989 |
| JP | H01225775 A | 9/1989 |
| JP | 1279745 | 11/1989 |
| JP | 2501490 | 5/1990 |
| JP | 3183759 A2 | 8/1991 |
| JP | H03260065 A | 11/1991 |
| JP | H03271374 A | 12/1991 |
| JP | 4000373 A | 1/1992 |
| JP | 4000374 A | 1/1992 |
| JP | 4000375 A | 1/1992 |
| JP | 4014440 A | 1/1992 |
| JP | H04124273 A | 4/1992 |
| JP | H0578844 A | 3/1993 |
| JP | H05263223 A | 10/1993 |
| JP | 6010132 A | 1/1994 |
| JP | 6289401 | 10/1994 |
| JP | 7041579 A | 2/1995 |
| JP | 7068614 A | 3/1995 |
| JP | 7126419 A | 5/1995 |
| JP | 7-304127 | 11/1995 |
| JP | 8025244 A | 1/1996 |
| JP | 8084773 A | 4/1996 |
| JP | H08296038 A | 11/1996 |
| JP | 9005038 A | 1/1997 |
| JP | 10008254 A | 1/1998 |
| JP | 10-130844 | 5/1998 |
| JP | 11-108833 A | 4/1999 |
| JP | 11106920 | 4/1999 |
| JP | H11256331 A | 9/1999 |
| JP | 11344316 A | 12/1999 |
| JP | 2000064040 A | 2/2000 |
| JP | 2000109076 A | 4/2000 |
| JP | 2001033398 A | 2/2001 |
| JP | 2001231841 A | 8/2001 |
| JP | 2002177364 A | 6/2002 |
| JP | 2002206167 A | 7/2002 |
| JP | 2002371364 A | 12/2002 |
| JP | 2003171771 A | 6/2003 |
| JP | 2003-268550 A | 9/2003 |
| JP | 2003294431 A | 10/2003 |
| JP | 2003305121 A | 10/2003 |
| JP | 2004002928 A | 1/2004 |
| JP | 2004008509 A | 1/2004 |
| JP | 2004043789 A | 2/2004 |
| JP | 2004100036 A | 4/2004 |
| JP | 2004156444 A | 6/2004 |
| JP | 2004168359 A | 6/2004 |
| JP | 2004169087 A | 6/2004 |
| JP | 2004203682 A | 7/2004 |
| JP | 2004-253683 A | 9/2004 |
| JP | 2004307935 A | 11/2004 |
| JP | 2005035597 A | 2/2005 |
| JP | 2005043285 A | 2/2005 |
| JP | 2005132416 A | 5/2005 |
| JP | 2005160888 A | 6/2005 |
| JP | 2005-200044 | 7/2005 |
| JP | 2005200044 A | 7/2005 |
| JP | 2005-241524 A | 9/2005 |
| JP | 2005271997 A | 10/2005 |
| JP | 2005290561 A | 10/2005 |
| JP | 2006-064416 A | 3/2006 |
| JP | 2006111967 A | 4/2006 |
| JP | 2006160268 A | 6/2006 |
| JP | 2006-224992 A | 8/2006 |
| JP | 2006249577 A | 9/2006 |
| JP | 2007050898 A | 3/2007 |
| JP | 2007231386 A | 9/2007 |
| JP | 2007246974 A | 9/2007 |
| JP | 2008174793 A | 7/2008 |
| JP | 2009-062620 A | 3/2009 |
| JP | 2009062620 A | 3/2009 |
| JP | 2009079298 A | 4/2009 |
| JP | 2009084203 A | 4/2009 |
| JP | 2009185330 A | 8/2009 |
| JP | 2010155134 A | 7/2010 |
| JP | 2010270117 A | 12/2010 |
| JP | 2012149278 A | 8/2012 |
| JP | 2012210315 A | 11/2012 |
| JP | 2012526921 A | 11/2012 |
| JP | 2013233716 A | 11/2013 |
| JP | 5362941 B2 | 12/2013 |
| KR | 10-2005-0100367 A | 10/2005 |
| KR | 10-2006-0029694 | 4/2006 |
| KR | 10-0685594 B1 | 2/2007 |
| SU | 1530913 | 12/1989 |
| TW | 200703536 A | 1/2007 |
| WO | WO9324243 A1 | 12/1993 |
| WO | WO9400247 A1 | 1/1994 |
| WO | WO9426497 A1 | 11/1994 |
| WO | WO95/24275 | 9/1995 |
| WO | WO97/11482 | 3/1997 |
| WO | WO97/13802 | 4/1997 |
| WO | WO98-27926 | 7/1998 |
| WO | WO98/45871 | 10/1998 |
| WO | WO9917334 A1 | 4/1999 |
| WO | WO99/41425 | 8/1999 |
| WO | WO9945984 A1 | 9/1999 |
| WO | WO9945985 A1 | 9/1999 |
| WO | WO9947192 A1 | 9/1999 |
| WO | WO99/50471 | 10/1999 |
| WO | WO0038566 A2 | 7/2000 |
| WO | WO0104668 A1 | 1/2001 |
| WO | WO0125788 | 4/2001 |
| WO | WO0154816 A1 | 8/2001 |
| WO | WO0156706 A1 | 8/2001 |
| WO | WO0170403 A1 | 9/2001 |
| WO | WO0222192 A1 | 3/2002 |
| WO | WO03033426 | 4/2002 |
| WO | WO02/43116 A2 | 5/2002 |
| WO | WO0249925 A1 | 6/2002 |
| WO | WO02/056333 A1 | 7/2002 |
| WO | WO02072914 | 9/2002 |
| WO | WO02076709 A1 | 10/2002 |
| WO | 02100928 A1 | 12/2002 |
| WO | WO03014415 A1 | 2/2003 |
| WO | WO03038143 | 5/2003 |
| WO | WO03040649 A1 | 5/2003 |
| WO | WO03044240 A1 | 5/2003 |
| WO | 2004044039 A2 | 5/2004 |
| WO | WO2005035147 A1 | 4/2005 |
| WO | WO2005/052555 A1 | 6/2005 |
| WO | WO2005051525 A1 | 6/2005 |
| WO | WO2005094214 A2 | 10/2005 |
| WO | WO2005103605 A1 | 11/2005 |
| WO | WO2006012281 A1 | 2/2006 |
| WO | WO2006017186 A1 | 2/2006 |
| WO | WO2006027568 A1 | 3/2006 |
| WO | WO2006029743 A1 | 3/2006 |
| WO | WO2006044254 A1 | 4/2006 |
| WO | WO2006/048650 | 5/2006 |
| WO | WO2006048276 | 5/2006 |
| WO | WO2006048277 A1 | 5/2006 |
| WO | WO2006069774 A1 | 7/2006 |
| WO | 2006121556 A3 | 11/2006 |
| WO | WO2006135755 A2 | 12/2006 |
| WO | WO2007028061 A2 | 3/2007 |
| WO | WO2007035741 A2 | 3/2007 |
| WO | WO2007036544 A1 | 4/2007 |
| WO | WO2007/081814 | 7/2007 |
| WO | WO2007089216 A1 | 8/2007 |
| WO | WO2007112328 A2 | 10/2007 |

(56) References Cited

FOREIGN PATENT DOCUMENTS

| WO | WO2007120507 A2 | 10/2007 |
|---|---|---|
| WO | WO2007133378 A1 | 11/2007 |
| WO | WO2007134347 A2 | 11/2007 |
| WO | WO2008014438 A2 | 1/2008 |
| WO | WO2008024566 A2 | 2/2008 |
| WO | WO2008040531 A1 | 4/2008 |
| WO | WO2008047541 A1 | 4/2008 |
| WO | WO2008067574 A1 | 6/2008 |
| WO | WO2008071458 A1 | 6/2008 |
| WO | WO2008093335 A2 | 8/2008 |
| WO | 2008/121478 A2 | 10/2008 |
| WO | WO2009/015862 A1 | 2/2009 |
| WO | WO2009020550 A2 | 2/2009 |
| WO | WO2009021257 A1 | 2/2009 |
| WO | WO2009030974 | 3/2009 |
| WO | WO2009030975 A1 | 3/2009 |
| WO | WO2009030976 A1 | 3/2009 |
| WO | WO2009031838 A1 | 3/2009 |
| WO | WO2009040109 | 4/2009 |
| WO | WO2009053947 A2 | 4/2009 |
| WO | WO2009112053 A1 | 9/2009 |
| WO | WO2009117032 | 9/2009 |
| WO | WO2009118361 A1 | 10/2009 |
| WO | WO2009158613 | 12/2009 |
| WO | WO2010047825 A1 | 4/2010 |
| WO | WO2010095011 A1 | 8/2010 |
| WO | WO2010/132579 | 11/2010 |
| WO | WO2010/132581 | 11/2010 |
| WO | WO2010/132584 | 11/2010 |
| WO | WO2010/132585 | 11/2010 |
| WO | WO2010/132589 | 11/2010 |
| WO | WO2010/132591 | 11/2010 |
| WO | WO2010034004 A1 | 11/2010 |
| WO | WO2010132579 | 11/2010 |
| WO | WO2010132579 A2 | 11/2010 |
| WO | WO2010132589 | 11/2010 |
| WO | WO2010132591 | 11/2010 |
| WO | WO2011029628 | 3/2011 |
| WO | WO20011059823 A1 | 5/2011 |
| WO | WO2011007055 A1 | 6/2011 |
| WO | WO2011080543 A1 | 7/2011 |
| WO | WO2011082296 A1 | 7/2011 |
| WO | WO2011090717 A1 | 7/2011 |
| WO | WO2011/143329 | 11/2011 |
| WO | WO2011/143509 | 11/2011 |
| WO | WO2011/143509 A1 | 11/2011 |
| WO | WO2011137437 | 11/2011 |
| WO | WO2011143329 | 11/2011 |
| WO | WO2011159975 A1 | 12/2011 |
| WO | WO2012003221 | 1/2012 |
| WO | WO2012009653 | 1/2012 |
| WO | WO2012166515 A1 | 12/2012 |
| WO | WO2013045671 A1 | 4/2013 |
| WO | WO2013/071138 | 5/2013 |
| WO | WO2013/071138 A1 | 5/2013 |
| WO | WO2013106588 A1 | 7/2013 |
| WO | WO2013/170044 | 11/2013 |
| WO | WO2013/170052 | 11/2013 |
| WO | WO2014/008138 | 1/2014 |
| WO | WO2014012039 A1 | 1/2014 |
| WO | WO2014012052 A1 | 1/2014 |
| WO | WO2014012072 A2 | 1/2014 |
| WO | WO2014012078 A2 | 1/2014 |
| WO | WO2014012079 A1 | 1/2014 |
| WO | WO2014014641 A1 | 1/2014 |
| WO | WO2014/059012 | 4/2014 |
| WO | WO2014/071061 | 5/2014 |
| WO | WO2014/078666 | 5/2014 |
| WO | WO2014/085346 | 6/2014 |
| WO | WO2014/085348 | 6/2014 |
| WO | WO2014/134577 | 9/2014 |
| WO | WO2014/144926 | 9/2014 |
| WO | WO2014/164928 | 10/2014 |
| WO | WO2015049972 A1 | 4/2015 |
| WO | WO2016057068 A1 | 4/2016 |
| WO | WO2016094387 A2 | 6/2016 |

OTHER PUBLICATIONS

Korean Patent Office, Office Action dated Jun. 21, 2016 in Patent Application No. 10-2011-7028713.
Mexican Patent Office, Office Action dated Jun. 7, 2016 in Patent Application No. MX/a/2011/012038 (3 pages).
Japanese Patent Office, Notice of Reasons for Refusal, Patent Application No. 2013-510276, dated Mar. 8, 2016 (15 pages).
European Patent Office, Communication pursuant to Article 94(3) EPC, in Application No. 13 726 337.2, dated Dec. 2, 2016 (6 pages).
Allison, H.L., The Real Markets for Transparent Barrier Films, 37th Annual Technical Conference Proceedings, 1994, ISBN 1-878068-13-X, pp. 458.
Bailey, R. et al., Thin-Film Multilayer Capacitors Using Pyrolytically Deposited Silicon Dioxide, IEEE Transactions on Parts, Hybrids, and Packaging, vol. PHP-12, No. 4, Dec. 1976, pp. 361-364.
Banks, B.A., et al., Fluoropolymer Filled $SiO_2$ Coatings; Properties and Potential Applications, Society of Vacuum Coaters, 35th Annual Technical Conference Proceedings, 1992, ISBN 1-878068-11-3, pp. 89-93.
Baouchi, W., X-Ray Photoelectron Spectroscopy Study of Sodium Ion Migration through Thin Films of $SiO_2$ Deposited on Sodalime Glass, 37th Annual Technical Conference Proceedings, 1994, ISBN 1-878068-13-X, pp. 419-422.
Boebel, F. et al., Simultaneous In Situ Measurement of Film Thickness and Temperature by Using Multiple Wavelengths Pyrometric Interferometry (MWPI), IEEE Transaction on Semiconductor Manufacturing, vol. 6, No. 2, May 1993, pp. 112-118.
Bush, V. et al., The Evolution of Evacuated Blood Collection Tubes, BD Diagnostics—Preanalytical Systems Newsletter, vol. 19, No. 1, 2009.
Chahroudi, D., Deposition Technology for Glass Barriers, 33rd Annual Technical Conference Proceedings, 1990, ISBN 1-878068-09-1, pp. 212-220.
Chahroudi, D., et al., Transparent Glass Barrier Coatings for Flexible Film Packaging, Society of Vacuum Coaters, 34th Annual Technical Conference Proceedings, 1991, ISBN 1-878068-10-5, pp. 130-133.
Chahroudi, D., Glassy Barriers from Electron Beam Web Coaters, 32nd Annual Technical Conference Proceedings, 1989, pp. 29-39.
Czeremuszkin, G. et al., Ultrathin Silicon-Compound Barrier Coatings for Polymeric Packaging Materials: An Industrial Perspective, Plasmas and Polymers, vol. 6, Nos. 1/2, Jun. 2001, pp. 107-120.
Ebihara, K. et al., Application of the Dielectric Barrier Discharge to Detect Defects in a Teflon Coated Metal Surface, 2003 J. Phys. D: Appl. Phys. 36 2883-2886, doi: 10.1088/0022-3727/36/23/003, IOP Electronic Journals, http://www.iop.org/EJ/abstract/0022-3727/36/23/003, printed Jul. 14, 2009.
Egitto, F.D., et al., Plasma Modification of Polymer Surfaces, Society of Vacuum Coaters, 36th Annual Technical Conference Proceedings, 1993, ISBN 1-878068-12-1, pp. 10-21.
Erlat, A.G. et al., SIOx Gas Barrier Coatings on Polymer Substrates: Morphology and Gas Transport Considerations, ACS Publications, Journal of Physical Chemistry, published Jul. 2, 1999, http://pubs.acs.org/doi/abs/10.1021/jp990737e, printed Jul. 14, 2009.
Fayet, P., et al., Commercialism of Plasma Deposited Barrier Coatings for Liquid Food Packaging, 37th Annual Technical Conference Proceedings, 1995, ISBN 1-878068-13-X, pp. 15-16.
Felts, J., Hollow Cathode Based Multi-Component Depositions, Vacuum Technology & Coating, Mar. 2004, pp. 48-55.
Felts, J.T., Thickness Effects on Thin Film Gas Barriers: Silicon-Based Coatings, Society of Vacuum Coaters, 34th Annual Technical Conference Proceedings, 1991, ISBN 1-878068-10-5, pp. 99-104.
Felts, J.T., Transparent Barrier Coatings Update: Flexible Substrates, Society of Vacuum Coaters, 36th Annual Technical Conference Proceedings, 1993, ISBN 1-878068-12-1, pp. 324-331.

(56) References Cited

OTHER PUBLICATIONS

Felts, J.T., Transparent Gas Barrier Technologies, 33rd Annual Technical Conference Proceedings, 1990, ISBN 1-878068-09-1, pp. 184-193.

Finson, E, et al., Transparent SiO2 Barrier Coatings: Conversion and Production Status, 37th Annual Technical Conference Proceedings, 1994, ISBN 1-878068-13-X, pp. 139-143.

Flaherty, T. et al., Application of Spectral Reflectivity to the Measurement of Thin-Film Thickness, Opto-Ireland 2002: Optics and Photonics Technologies and Applications, Proceedings of SPIE vol. 4876, 2003, pp. 976-983.

Hora, R., et al., Plasma Polymerization: A New Technology for Functional Coatings on Plastics, 36th Annual Technical Conference Proceedings, 1993, ISBN 1-878068-12-1, pp. 51-55.

Izu, M., et al., High Performance Clear CoatTM Barrier Film, 36th Annual Technical Conference Proceedings, 1993, ISBN 1-878068-12-1, pp. 333-340.

Jost, S., Plasma Polymerized Organosilicon Thin Films on Reflective Coatings, 33rd Annual Technical Conference Proceedings, 1990, ISBN 1-878068-09-1, pp. 344-346.

Kaganowicz, G., et al., Plasma-Deposited Coatings—Properties and Applications, 23rd Annual Technical Conference Proceedings, 1980, pp. 24-30.

Kamineni, V. et al., Thickness Measurement of Thin Metal Films by Optical Metrology, College of Nanoscale Science and Engineering, University of Albany, Albany, NY.

Klemberg-Sapieha, J.E., et al., Transparent Gas Barrier Coatings Produced by Dual Frequency PECVD, 36th Annual Technical Conference Proceedings, 1993, ISBN 1-878068-12-1, pp. 445-449.

Krug, T., et al., New Developments in Transparent Barrier Coatings, 36th Annual Technical Conference Proceedings, 1993, ISBN 1-878068-12-1, pp. 302-305.

Kuhr, M. et al., Multifunktionsbeschichtungen für innovative Applikationen von Kunststoff-Substraten, HiCotec Smart Coating Solutions.

Kulshreshtha, D.S., Specifications of a Spectroscopic Ellipsometer, Department of Physics & Astrophysics, University of Delhi, Delhi-110007, Jan. 16, 2009.

Krug, T.G., Transparent Barriers for Food Packaging, 33rd Annual Technical Conference Proceedings, 1990, ISBN 1-878068-09-1, pp. 163-169.

Lee, K. et al., The Ellipsometric Measurements of a Curved Surface, Japanese Journal of Applied Physics, vol. 44, No. 32, 2005, pp. L1015-L1018.

Lelait, L. et al., Microstructural Investigations of EBPVD Thermal Barrier Coatings, Journal De Physique IV, Colloque C9, supplément au Journal de Physique III, vol. 3, Dec. 1993, pp. 645-654.

Masso, J.D., Evaluation of Scratch Resistant and Antireflective Coatings for Plastic Lenses, 32nd Annual Technical Conference Proceedings, 1989, p. 237-240.

Misiano, C., et al., New Colourless Barrier Coatings (Oxygen & Water Vapor Transmission Rate) on Plastic Substrates, 35th Annual Technical Conference Proceedings, 1992, ISBN 1-878068-11-3, pp. 28-40.

Misiano, C., et al., Silicon Oxide Barrier Improvements on Plastic Substrate, Society of Vacuum Coaters, 34th Annual Technical Conference Proceedings, 1991, ISBN 1-878068-10-5, pp. 105-112.

Mount, E, Measuring Pinhole Resistance of Packaging, Corotec Corporation website, http://www.convertingmagazine.com, printed Jul. 13, 2009.

Murray, L et al., The Impact of Foil Pinholes and Flex Cracks on the Moisture and Oxygen Barrier of Flexible Packaging.

Nelson, R.J., et al., Double-Sided QLF® Coatings for Gas Barriers, Society of Vacuum Coaters, 34th Annual Technical Conference Proceedings, 1991, ISBN 1-878068-10-5, pp. 113-117.

Nelson, R.J., Scale-Up of Plasma Deposited SiOx Gas Diffusion Barrier Coatings, 35th Annual Technical Conference Proceedings, 1992, ISBN 1-878068-11-3, pp. 75-78.

Novotny, V. J., Ultrafast Ellipsometric Mapping of Thin Films, IBM Technical Disclosure Bulletin, vol. 37, No. 02A, Feb. 1994, pp. 187-188.

Rüger, M., Die Pulse Sind das Plus, PICVD-Beschichtungsverfahren.

Schultz, A. et al., Detection and Identification of Pinholes in Plasma-Polymerised Thin Film Barrier Coatings on Metal Foils, Surface & Coatings Technology 200, 2005, pp. 213-217.

Stchakovsky, M. et al., Characterization of Barrier Layers by Spectroscopic Ellipsometry for Packaging Applications, Horiba Jobin Yvon, Application Note, Spectroscopic Ellipsometry, SE 14, Nov. 2005.

Teboul, E., Thi-Film Metrology: Spectroscopic Ellipsometer Becomes Industrial Thin-Film Tool, LaserFocusWorld, http://www.laserfocusworld.com/display_article, printed Jul. 14, 2009.

Teyssedre, G. et al., Temperature Dependence of the Photoluminescence in Poly(Ethylene Terephthalate) Films, Polymer 42, 2001, pp. 8207-8216.

Tsung, L. et al., Development of Fast CCD Cameras for In-Situ Electron Microscopy, Microsc Microanal 14(Supp 2), 2008.

Wood, L. et al., A Comparison of SiO2 Barrier Coated Polypropylene to Other Coated Flexible Substrates, 35th Annual Technical Conference Proceedings, 1992, ISBN 1-878068-11-3, pp. 59-62.

Yang, et al., Microstructure and tribological properties of SiOx/DLC films grown by PECVD, Surface and Coatings Technology, vol. 194, Issue 1, Apr. 20, 2005, pp. 128-135.

An 451, Accurate Thin Film Measurements by High-Resoluiton Transmission Electron Microscopy (HRTEM), Evans Alalytical Group, Version 1.0, Jun. 12, 2008, pp. 1-2.

Benefits of TriboGlide, TriboGlide Silicone-Free Lubrication Systems, http://www.triboglide.com/benfits.htm, printed Aug. 31, 2009.

Australian Government, IP Australia, Patent Examination Report No. 1, in Application No. 2010249031, dated Mar. 13, 2014. (4 pages).

Australian Government, IP Australia, Patent Examination Report No. 1, in Application No. 2013202893, dated Mar. 13, 2014. (4 pages).

European Patent Office, Communication pursuant to Article 93(3) EPC, in Application No. 11 731 554.9 dated Apr. 15, 2014. (7 pages).

PCT, Notification Concerning Transmittal of International Preliminary Report on Patentability, in International application No. PCT/US2012/064489, dated May 22, 2014. (10 pages).

PCT, Notification of Transmittal of the International Search Report and the Written Opinion of the International Searching Authority, or the Declaration, in International application No. PCT/US2013/071750, dated Apr. 4, 2014. (13 pages).

PCT, Notification of Transmittal of the International Search Report and the Written Opinion of the International Searching Authority, or the Declaration, in International application No. PCT/US2014/019684, dated May 23, 2014. (16 pages).

PCT, Notification of Transmittal of the International Search Report and the Written Opinion of the International Searching Authority, or the Declaration, in International application No. PCT/US2014/023813, dated May 22, 2014. (11 pages).

European Patent Office, Communication pursuant to Article 94(3) EPC, in Application No. 11 736 511.4, dated Mar. 28, 2014.

PCT, Notification Concerning Transmittal of International Preliminary Report on Patentability, in International application No. PCT/US2011/042387, dated Jan. 17, 2013. (7 pages).

State Intellectual Property Office of the People's Republic of China, Notification of the First Office Action, in Application No. 201180032145.4, dated Jan. 30, 2014. (16 pages).

PCT, Notification Concerning Transmittal of International Preliminary Report on Patentability, in International application No. PCT/US2011/044215, dated Jan. 31, 2013. (14 pages).

Da Silva Sobrinho A S et al., "Transparent barrier coatings on polyethylene terephthalate by single-and dual-frequency plasma-enhanced chemical vapor deposition", Journal of Vacuum Science and Technology; Part A, AVS/AIP, Melville, NY, US, vol. 16, No. 6, Nov. 1, 1998 (Nov. 1, 1998), pp. 3190-3198, XP01200471, ISSN: 0734-2101, DOI: 10.1116/1.581519 (9 pages).

(56) References Cited

OTHER PUBLICATIONS

State Intellectual Property Office of the People's Republic of China, Notification of the Third Office Action, in Application No. 201080029201.4, dated Jul. 7, 2014 (15 pages).
PCT, Notification of Transmittal of the International Search Report and the Written Opinion of the International Searching Authority, or the Declaration, in International application No. PCT/US2014/029531, dated Jun. 20, 2014 (12 pages).
State Intellectual Property Office of the People's Republic of China, Notification of the Third Office Action, with translation, in Application No. 201080029199.0, dated Jun. 27, 2014 (19 pages).
Intellectual Property Office of Singapore, Invitation to Respond to Written Opinion, in Application No. 2012083077, dated Jun. 30, 2014 (12 pages).
PCT, Notification of Transmittal of International Preliminary Report on Patentability, in International application No. PCT/US13/40368, dated Jul. 16, 2014 (6 pages).
Australian Government, IP Australia, Patent Examination Report No. 1, in Application No. 2012318242, dated Apr. 30, 2014. (6 pages).
State Intellectual Property Office of the People's Republic of China, Notification of the First Office Action, in Application No. 201180023461.5, dated May 21, 2014. (25 pages).
European Patent Office, Communication pursuant to Article 94(3) EPC, in Application No. 10162758.6 dated May 27, 2014. (7 pages).
Australian Government, IP Australia, Patent Examination Report No. 1, in Application No. 2011252925, dated Sep. 6, 2013 (3 pages).
Coating Syringes, http://www.triboglide.com/syringes.htm, printed Aug. 31, 2009.
Coating/Production Process, http://www.triboglide.com/process.htm, printed Aug. 31, 2009.
Munich Exp, Materialica 2005: Fundierte Einblicke in den Werkstofsektor, Seite 1, von 4, ME095-6.
Schott Developing Syringe Production in United States, Apr. 14, 2009, http://www.schott.com/pharmaceutical_packaging, printed Aug. 31, 2009.
Sterile Prefillable Glass and Polymer Syringes, Schott forma vitrum, http://www.schott.com/pharmaceutical_packaging.
Transparent and recyclingfähig, neue verpackung, Dec. 2002, pp. 54-57.
European Patent Office, Communication with European Search Report, in Application No. 10162758.6, dated Aug. 19, 2010.
Griesser, Hans J., et al., Elimination of Stick-Slip of Elastomeric Sutures by Radiofrequency Glow Discharge Deposited Coatings, Biomed Mater. Res. Appl Biomater, 2000, vol. 53, 235-243, John Wiley & Sons, Inc.
European Patent Office, Communication with extended Search Report, in Application No. EP 10162761.0, dated Feb. 10, 2011.
European Patent Office, Communication with partial Search Report, in Application No. EP 10162758.6, dated Aug. 19, 2010.
European Patent Office, Communication with extended Search Report, in Application No. EP 10162758.6, dated Dec. 21, 2010.
Yang, et al., Microstructure and tribological properties of SiOx/DLC films grown by PECVD, Surface and Coatings Technology, vol. 194 (2005), Apr. 20, 2005, pp. 128-135.
European Patent Office, Communication with extended European search report, in Application No. EP10162756.0, dated Nov. 17, 2010.
Prasad, G.R. et al., "Biocompatible Coatings with Silicon and Titanium Oxides Deposited by PECVD", 3rd Mikkeli International Industrial Coating Seminar, Mikkeli, Finland, Mar. 16-18, 2006.
European Patent Office, Communication with extended European search report, in Application No. EP10162757.8, dated Nov. 10, 2010.
Patent Cooperation Treaty, Notification of Transmittal of the International Search Report and the Written Opinion of the International Searching Authority, in PCT/US2010/034568, dated Jan. 21, 2011.
Patent Cooperation Treaty, Notification of Transmittal of the International Search Report and the Written Opinion of the International Searching Authority, in PCT/US2010/034571, dated Jan. 26, 2011.
Patent Cooperation Treaty, Notification of Transmittal of the International Search Report and the Written Opinion of the International Searching Authority, in PCT/US2010/034576, dated Jan. 25, 2011.
Patent Cooperation Treaty, Notification of Transmittal of the International Search Report and the Written Opinion of the International Searching Authority, in PCT/US2010/034577, dated Jan. 21, 2011.
Patent Cooperation Treaty, Notification of Transmittal of the International Search Report and the Written Opinion of the International Searching Authority, in PCT/US2010/034582, dated Jan. 24, 2011.
European Patent Office, Communication with Extended Search Report, in Application No. EP 10162755.2, dated Nov. 9, 2010.
European Patent Office, Communication with Extended Search Report, in Application No. EP 10162760.2, dated Nov. 12, 2010.
PCT, Written Opinion of the International Searching Authority with International Search Report in Application No. PCT/US2010/034586, dated Mar. 15, 2011.
Shimojima, Atsushi et al., Structure and Properties of Multilayered Siloxane-Organic Hybrid Films Prepared Using Long-Chain Organotrialkoxysilanes Containing C=C Double Bonds, Journal of Materials Chemistry, 2007, vol. 17, pp. 658-663, © The Royal Society of Chemistry, 2007.
Sone, Hayato et al., Picogram Mass Sensor Using Resonance Frequency Shift of Cantilever, Japanese Journal of Applied Physics, vol. 43, No. 6A, 2004, pp. 3648-3651, © The Japan Society of Applied Physics.
Sone, Hayato et al., Femtogram Mass Sensor Using Self-Sensing Cantilever for Allergy Check, Japanese Journal of Applied Physics, vol. 45, No. 3B, 2006, pp. 2301-2304, © The Japan Society of Applied Physics.
Mallikarjunan, Anupama et al, The Effect of Interfacial Chemistry on Metal Ion Penetration into Polymeric Films, Mat. Res. Soc. Symp. Proc. vol. 734, 2003, © Materials Research Society.
Schonher, H., et al., Friction and Surface Dynamics of Polymers on the Nanoscale by AFM, STM and AFM Studies on (Bio)molecular Systems: Unravelling the Nanoworld. Topics in Current Chemistry, 2008, vol. 285, pp. 103-156, © Springer-Verlag Berlin Heidelberg.
Lang, H.P., Gerber, C., Microcantilever Sensors, STM and AFM Studies on (Bio)molecular Systems: Unravelling the Nanoworld. Topics in Current Chemistry, 2008, vol. 285, pp. 1-28, © Springer-Verlag Berlin Heidelberg.
Sahagian, Khoren; Larner, Mikki; Kaplan, Stephen L., "Altering Biological Interfaces with Gas Plasma: Example Applications", Plasma Technology Systems, Belmont, CA, In SurFACTS in Biomaterials, Surfaces in Biomaterials Foundation, Summer 2013, 18(3), p. 1-5.
Daikyo Cyrystal Zenith Insert Needle Syringe System, West Delivering Innovative Services, West Pharmaceutical Services, Inc., 2010.
Daikyo Crystal Zenigh Syringes, West Pharmaceutical Services, Inc., www. WestPFSsolutions.com, #5659, 2011.
Zhang, Yongchao and Heller, Adam, Reduction of the Nonspecific Binding of a Target Antibody and of Its Enzyme-Labeled Detection Probe Enabling Electrochemical Immunoassay of Antibody through the 7 pg/mL—100 ng/nL (40 fM-400 pM) Range, Department of Chemical Engineering and Texas Materials Institute, University of Texas at Austin, Anal. Chem. 2005, 7, 7758-7762. (6 pages).
Principles and Applications of Liquid Scintillation Counting, LSC Concepts—Fundamentals of Liquid Scintillation Counting, National Diagnostics, 2004, pp. 1-15.
Chikkaveeraiah, Bhaskara V. and Rusling, Dr. James, Non Specific Binding (NSB) in Antigen-Antibody Assays, University of Connecticut, Spring 2007. (13 pages).
Sahagian, Khoren; Larner, Mikki; Kaplan, Stephen L., "Cold Gas Plasma in Surface Modification of Medical Plastics", Plasma Technology Systems, Belmont, CA, Publication pending. Presented at SPE Antec Medical Plastics Division, Apr. 23, 2013, Ohio.
Lipman, Melissa, "Jury Orders Becton to Pay $114M in Syringe Antitrust Case", © 2003-2013, Portfolio Media, Inc., Law360, New York (Sep. 20, 2013, 2:53 PM ET), http://www.law360.com/articles/474334/print?section=ip, [retrieved Sep. 23, 2013].
Wikipedia, the free encyclopedia, http://en.wikipedia.org/wiki/Birefringence, page last modified Sep. 18, 2013 at 11:39. [retrieved on Oct. 8, 2013]. (5 pages).

(56) References Cited

OTHER PUBLICATIONS

Wikipedia, the free encyclopedia, http://en.wikipedia.org/wiki/Confocal_microscopy, page last modified Aug. 28, 2013 at 11:12. [retrieved on Oct. 8, 2013]. (4 pages).
Wang, Jun et al., "Fluorocarbon thin film with superhydrophobic property prepared by pyrolysis of hexafluoropropylene oxide", Applied Surface Science, vol. 258, 2012, pp. 9782-9784 (4 pages).
Wang, Hong et al., "Ozone-Initiated Secondary Emission Rates of Aldehydes from Indoor surfaces in Four Homes", American Chemical Society, Environmental Science & Technology, vol. 40, No. 17, 2006, pp. 5263-5268 (6 pages).
Lewis, Hilton G. Pryce, et al., "HWCVD of Polymers: Commercialization and Scale-Up", Thin Solid Films 517, 2009, pp. 3551-3554.
Wolgemuth, Lonny, "Challenges With Prefilled Syringes: The Parylene Solution", Frederick Furness Publishing, www.ongrugdelivery.com, 2012, pp. 44-45.
History of Parylene (12 pages).
SCS Parylene HTX brochure, Stratamet Thin Film Corporation, Fremont, CA, 2012, retrieved from the Internet Feb. 13, 2013, http://www.stratametthinfilm.com/parylenes/htx. (2 pages).
SCS Parylene Properties, Specialty Coating Systems, Inc., Indianapolis, IN, 2011. (12 pages).
Werthheimer, M.R., Studies of the earliest stages of plasma-enhanced chemical vapor deposition of SiO2 on polymeric substrates, Thin Solid Films 382 (2001) 1-3, and references therein, United States Pharmacopeia 34. In General Chapters <1>, 2001.
Gibbins, Bruce and Warner, Lenna, The Role of Antimicrobial Silver Nanotechnology, Medical Device & Diagnostic Industry, Aug. 205, pp. 2-6.
MTI CVD Tube Furnace w Gas Delivery & Vacuum Pump, http://mtixtl.com/ MiniCVDTubeFurnace2ChannelsGasVacuum-OTF-1200X-S50-2F.aspx (2 pages).
Lab-Built HFPO CVD Coater, HFPO Decomp to Give Thin Fluorocarbon Films, Applied Surface Science 2012 258 (24) 9782.
Technical Report No. 10, Journal of Parenteral Science and Technology, 42, Supplement 1988, Parenteral Formulation of Proteins and Peptides: Stability and Stabilizers, Parenteral Drug Association, 1988.
Technical Report No. 12, Journal of Parenteral Science and Technology, 42, Supplement 1988, Siliconization of Parenteral Drug Packaging Components, Parenteral Drug Association, 1988.
European Patent Office, Communication under Rule 71(3) EPC, in Application No. 10 162 760.2-1353, dated Oct. 25, 2013. (366 pages).
Wikipedia, the free encyclopedia, http://en.wikipedia.org/wiki/Difluorocarbene, page last modified Feb. 20, 2012 at 14:41. [retrieved on Sep. 7, 2012]. (4 pages).
D'Shaughnessy, W.S., et al., "Initiated Chemical Vapor Deposition of a Siloxane Coating for Insulation of Neutral Probes", Thin Solid Films 517 (2008) 3612-3614. (3 pages).
Denler, et al, Investigations of SiOx-polymer "interphases" by glancing angle RBS with Li+ and Be+ions, Nuclear Instruments and Methods in Physical Research B 208 (2003) 176-180, United States Pharmacopeia 34. In General Chapters <1>, 2003.
PCT, Invitation to Pay Additional Fees and Annex to Form PCT/ISA/206 Communication relating to the results of the partial international search in International application No. PCT/US2013/071750, dated Feb. 14, 2014. (6 pages).
PCT, Notification of Transmittal of the International Search Report and the Written Opinion of the International Searching Authority, or the Declaration, in International application No. PCT/US2013/62247, dated Dec. 30, 2013. (13 pages).
PCT, Notification of Transmittal of the International Search Report and the Written Opinion of the International Searching Authority, or the Declaration, in International application No. PCT/US2013/043642, dated Dec. 5, 2013. (21 pages).
Japanese Patent Office, Notice of Reason(s) for Rejection in Patent application No. 2012-510983, dated Jan. 7, 2014. (6 pages).
Chinese Patent Office, Notification of the Second Office Action in Application No. 201080029199.0, dated Jan. 6, 2014. (26 pages).
Chinese Patent Office, Notification of the First Office Action in Application No. 201180023474.2, dated Dec. 23, 2013. (18 pages).
PCT, Notification of Transmittal of the International Search Report and the Written Opinion of the International Searching Authority, or the Declaration, in International application No. PCT/US2013/067852, dated Jan. 22, 2014. (9 pages).
PCT, Notification of Transmittal of the International Search Report and the Written Opinion of the International Searching Authority, or the Declaration, in International application No. PCT/US2013/064121, dated Mar. 24, 2014. (8 pages).
PCT, Notification of Transmittal of the International Search Report and the Written Opinion of the International Searching Authority, or the Declaration, in International application No. PCT/US2013/070325, dated Mar. 24, 2014. (16 pages).
Patent Cooperation Treaty, Written Opinion of the International Searching Authority with International Search Report in Application No. PCT/US2012/064489, dated Jan. 25, 2013.
Danish Patent and Trademark Office, Singapore Written Opinion, in Application No. 201108308-6, dated Dec. 6, 2012.
Danish Patent and Trademark Office, Singapore Search Report, in Application No. 201108308-6, dated Dec. 12, 2012.
Tao, Ran et al., Condensationand Polymerization of Supersaturated Monomer Vapor, ACS Publications, 2012 American Chemical Society, ex.doi.org/10.1021/la303462q/Langmuir 2012, 28, 16580-16587.
State Intellectual Property Office of Teh People's Republic of China, Notification of First Office Action in Application No. 201080029201.4, dated Mar. 37, 2013. (15 pages).
PCT, Notification of Transmittal of the International Search Report and the Written Opinion of the International Searching Authority, or the Declaration, in International application No. PCT/US2013/040380, dated Sep. 3, 2013. (13 pages).
PCT, Notification of Transmittal of the International Search Report and the Written Opinion of the International Searching Authority, or the Declaration, in International application No. PCT/US2013/040368, dated Oct. 21, 2013. (21 pages).
PCT, Notification of Transmittal of the International Search Report and the Written Opinion of the International Searching Authority, or the Declaration, in International application No. PCT/US2013/048709, dated Oct. 2, 2013. (7 pages).
Coclite A.M. et al., "On the relationship between the structure and the barrier performance of plasma deposited silicon dioxide-like films", Surface and Coatings Technology, Elsevier, Amsterdam, NL, vol. 204, No. 24, Sep. 15, 2010 (Sep. 15, 2010), pp. 4012-4017, XPO27113381, ISSN: 0257-8972 [retrieved on Jun. 16, 2010] abstract, p. 4014, right-hand column—p. 4015, figures 2, 3.
Brunet-Bruneau A. et al, "Microstructural characterization of ion assisted Sio2 thin films by visible and infrared. ellipsometry", Journal of Vacuum Science and Technology: Part A, AVS/AIP, Melville, NY, US, vol. 16, No. 4, Jul. 1, 1998 (Jul. 1, 1998), pp. 2281-2286, XPO12004127, ISSN: 0734-2101, DOI: 10.1116/1.581341, p. 2283, right-hand column—p. 2284, left-hand column, figures 2, 4.
Patent Cooperation Treaty, Notification of Transmittal of International Preliminary Report on Patentability, in Application No. PCT/US2010/034576, dated Sep. 14, 2011.
Patent Cooperation Treaty, Notification of Transmittal of International Preliminary Report on Patentability, in Application No. PCT/US2010/034568, dated Sep. 14, 2011.
Patent Cooperation Treaty, International Search Report and Written Opinion, in Application No. PCT/US2011/036358, dated Sep. 9, 2011.
Patent Cooperation Treaty, International Search Report and Written Opinion, in Application No. PCT/US2011/036340, dated Aug. 1, 2011.
MacDonald, Gareth, "West and Daikyo Seiko Launch Ready Pack", http://www.in-pharmatechnologist.com/Packaging/West-and-Daikyo-Seiko-launch-Ready-Pack, 2 pages, retrieved from the Internet Sep. 22, 2011.
Kumer, Vijai, "Development of Terminal Sterilization Cycle for Pre-Filled Cyclic Olefin Polymer (COP) Syringes", http://abstracts.

(56) References Cited

OTHER PUBLICATIONS aapspharmaceutica.com/ExpoAAPS09/CC/forms/attendee/index. aspx?content=sessionInfo&sessionId=401, 1 page, retrieved from the internet Sep. 22, 2011.
Quinn, F.J., "Biotech Lights Up the Glass Packaging Picture", http://www.pharmaceuticalcommerce.com/frontEnd/main.php?idSeccion=840, 4 pages, retrieved from the Internet Sep. 21, 2011.
Wen, Zai-Qing et al., Distribution of Silicone Oil in Prefilled Glass Syringes Probed with Optical and Spectroscopic Methods, PDA Journal of Pharmaceutical Science and Technology 2009, 63, pp. 149-158.
ZebraSci—Intelligent Inspection Products, webpage, http://zebrasci.com/index.html, retrieved from the internet Sep. 30, 2011.
Google search re "cyclic olefin polymer resin" syringe or vial, http://www.google.com/search?sclient=psy-ab&hl=en&lr=&source=hp&q=%22cyclic+olefin+polymer+resin%22+syringe+OR+vial&btnG=Search&pbx=1&oq=%22cyclic+olefin+polymer+resin%22+syringe+OR+vial&aq, 1 page, retrieved from the internet Sep. 22, 2011.
Taylor, Nick, "West to Add CZ Vials as Glass QC Issues Drive Interest", ttp://twitter.com/WestPharma/status/98804071674281986, 2 pages, retrieved from the Internet Sep. 22, 2011.
Patent Cooperation Treaty, International Preliminary Examining Authority, Notification of Transmittal of International Preliminary Report on Patentability, in international application No. PCT/US2010/034571, dated Jun. 13, 2011.
Patent Cooperation Treaty, International Preliminary Examining Authority, Written Opinion of the International Preliminary Examining Authority, in international application No. PCT/US2010/034586, dated Aug. 23, 2011.
Patent Cooperation Treaty, International Preliminary Examining Authority, Written Opinion of the International Preliminary Examining Authority, in international application No. PCT/US2010/034568, dated May 30, 2011.
Silicone Oil Layer, Contract Testing, webpage, http://www.siliconization.com/downloads/siliconeoillayercontracttesting.pdf, retrieved from the internet Oct. 28, 2011.
Patent Cooperation Treaty, Notification of Transmittal of International Preliminary Report on Patentability, in PCT/US2010/034577, dated Nov. 24, 2011.
Patent Cooperation Treaty, Notification of Transmittal of International Preliminary Report on Patentability, in PCT/US2010/034582, dated Nov. 24, 2011.
Patent Cooperation Treaty, Notification of Transmittal of International Preliminary Report on Patentability, in PCT/US2010/034586, dated Dec. 20, 2011.
Patent Cooperation Treaty, Notification of Transmittal of the International Search Report and the Written Opinion of the International Searching Authority, in PCT/US2011/036097, dated Dec. 29, 2011.
"Oxford instruments plasmalab 80plus", XP55015205, retrieved from the Internet on Dec. 20, 2011, URL:http://www.oxfordplasma.de/pdf_inst/plas_80_pdf.
Patent Cooperation Treaty, Notification of Transmittal of the International Search Report and the Written Opinion of the International Searching Authority, in PCT/US2011/044215, dated Dec. 29, 2011.
European Patent Office, Communication pursuant to Article 94(3) EPC, in Application No. 10 162 758.6-1234, dated May 8, 2012 (6 pages).
Hanlon, Adriene Lepiane, Pak, Chung K., Pawlikowski, Beverly A., Decision on Appeal, Appeal No. 2005-1693, U.S. Appl. No. 10/192,333, dated Sep. 30, 2005.
Arganguren, Mirta I., Macosko, Christopher W., Thakkar, Bimal, and Tirrel, Matthew, "Interfacial Interactions in Silica Reinforced Silicones," Materials Research Society Symposium Proceedings, vol. 170, 1990, pp. 303-308.

Patent Cooperation Treaty, International Preliminary Examining Authority, Notification of Transmittal of International Preliminary Report on Patentability, in international application No. PCT/US2011/036097, dated Nov. 13, 2012.
PCT, Written Opinion of the International Preliminary Examining Authority, in International application No. PCT/USUS13/048709, dated Sep. 30, 2014 (4 pages).
PCT, Notification of Transmittal of the International Preliminary Report on Patentability, in International application No. PCT/USUS13/048709, dated Oct. 15, 2014 (7 pages).
PCT, Written Opinion of the International Preliminary Examining Authority, in International application No. PCT/USUS13/064121, dated Nov. 19, 2014 (8 pages).
PCT, Written Opinion of the International Preliminary Examining Authority, in International application No. PCT/USUS13/064121, dated Nov. 21, 2014 (7 pages).
Intellectual Property Corporation of Malaysia, Substantive Examintion Adverse Report (section 30(1)/30(2)), in Application No. PI 2011005486, dated Oct. 31, 2014 (3 pages).
Patent Office of the Russian Federation, Official Action, in Application No. 2011150499, dated Sep. 25, 2014 (4 pages).
Instituto Mexicano de la Propiedad Indutrial, Official Action, in Appilcation No. MX/a/2012/013129, dated Sep. 22, 2014 (5 pages).
Australian Government, Patent Examination Report No. 2 in Application No. 2010249031 dated Apr. 21, 2015.
Japanese Patent Office, Notice of Reasons for Refusal in application No. 2013-510276, dated Mar. 31, 2015.
Bose, Sagarika and Constable, Kevin, Advanced Delivery Devices, Design & Evaluation of a Polymer-Based Prefillable Syringe for Biopharmaceuticals With Improved Functionality & Performance, JR Automation Technologies, May 2015.
Hopwood J Ed—CRC Press: "Plasma-assisted deposition", Aug. 17, 1997 (Aug. 17, 1997), Handbook of Nanophase Materials, Chapter 6, pp. 141-197, XP008107730, ISBN: 978-0-8247-9469-9.
PCT, Written Opinion of the International Preliminary Examining Authority, International application No. PCT/SU2013/071752, dated May 6, 2015.
Hlobik, Plastic Pre-Fillable Syringe Systems (http://www.healthcarepackaging.com/package-type/Containers/plastic-prefillablesyringe-systems, Jun. 8, 2010).
PCT, Written Opinion of the International Preliminary Examining Authority, in International application No. PCT/US2013/071750, dated Jan. 20, 2015 (9 pages).
PCT, Written Opinion of the International Preliminary Examining Authority, in International application No. PCT/US2013/064121, dated Nov. 21, 2014 (7 pages).
Japanese Patent Office, Decision of Rejection in Application No. 2012-510983, dated Jan. 20, 2015 (4 pages).
Australian Government, IP Australia, Patent Examination Report No. 1, in Application No. 2010249033, dated Dec. 19, 2014 (7 pages).
Australian Government, IP Australia, Patent Examination Report No. 1, in Application No. 2011252925, dated Dec. 2, 2014 (3 pages).
State Intellectual Property Office of the People's Republic of China, Notification of the Fourth Office Action in Application No. 201080029199.0, dated Mar. 18, 2015 (15 pages).
Reh, et al., Evaluation of stationary phases for 2-dimensional HPLC of Proteins—Validation of commercial RP-columns, Published by Elsevier B.V., 2000.
L. Martinu, O. Zabeida, and J.E. Klemberg-Sapieha, "Plasma-Enhanced Chemical Vapor Deposition of Functional Coatings", Handbook of Deposition Technologies for Films and Coating, Chapter 9, pp. 392-464, 2010.

* cited by examiner

PHARMACEUTICAL AND OTHER PACKAGING WITH LOW OXYGEN TRANSMISSION RATE

CROSS-REFERENCE TO RELATED APPLICATIONS

This application is a U.S. National Phase of International Application No. PCT/US2016/047622 filed Aug. 18, 2016, which claims priority to U.S. Provisional Patent Application No. 62/206,637 filed Aug. 18, 20115, which are incorporated herein by reference in their entirety.

RELATED APPLICATIONS

This application claims the priority of provisional U.S. patent application Ser. No. 62/206,637, filed Aug. 18, 2015. The specification and drawings of Ser. No. 62/206,637, as well as the specification and drawings of U.S. Pat. No. 7,985,188 and U.S. Ser. No. 14/751,435, filed Jun. 26, 2015, are incorporated here by reference in their entirety. The incorporated patent and application describe apparatus, vessels, precursors, coatings or layers and methods (in particular coating methods and test methods for examining the coatings or layers) which can generally be used in performing the present invention, in some cases as modified herein. They also describe SiOxCy tie coatings or layers and pH protective coatings or layers and SiOx barrier coatings or layers to which reference is made herein.

FIELD OF THE INVENTION

The present invention relates to the technical field of barrier coated surfaces, for example interior surfaces of pharmaceutical packages or other vessels for storing or other contact with fluids. Examples of suitable fluids include foods, nutritional supplements, drugs, inhalation anaesthetics, diagnostic test materials, or biologically active compounds or body fluids, for example blood. The present invention also relates to a blood collection tube or other vessel having a gas barrier coating and optionally a pH protective coating to protect the gas barrier coating.

The present disclosure also relates to improved methods for processing pharmaceutical packages or other vessels, for example multiple identical pharmaceutical packages or other vessels used for pharmaceutical preparation storage and delivery, venipuncture and other medical sample collection (for example evacuated blood sample collection tubes), and other purposes.

The present disclosure also relates to the resulting packages pharmaceutical packages or other vessels. Such pharmaceutical packages or other vessels are used in large numbers, and must be relatively economical to manufacture and yet highly reliable in storage and use.

BACKGROUND OF THE INVENTION

One important consideration in manufacturing pharmaceutical packages or other vessels for storing or other contact with fluids, for example vials, pre-filled syringes, or sample collection tubes, is that the contents of the pharmaceutical package or other vessel desirably will have a substantial shelf life. During this shelf life, it is important to isolate any material contained in the pharmaceutical package or other vessel from the vessel wall containing it, or from barrier layers or other functional layers applied to the pharmaceutical package or other vessel wall to avoid extracting material from the pharmaceutical package or other vessel wall, barrier layer, or other functional layers into the prefilled contents or vice versa.

Some companies have turned to plastic pharmaceutical packages or other vessels, which provide greater dimensional tolerance and less breakage than glass, but the use of plastic for primary pharmaceutical packaging remains limited due to its relatively high gas (oxygen) permeation rate: Plastic allows small molecule gases to permeate into (or out of) the article. The permeation rate constants of plastics to gases are significantly greater than that of glass and, in many cases (as with oxygen-sensitive drugs such as epinephrine), plastics have been unacceptable for that reason.

The problem of the relatively high permeation rate constant of thermoplastic vessels has been addressed by adding a barrier coating or layer to the vessel wall. One such barrier layer is a very thin coating of SiOx, as defined below, applied by plasma enhanced chemical vapor deposition to the internal surface of the wall defining the lumen. But, current SiOx barrier layers deposited on a package by PECVD are etched off by aqueous contents of the vessels having pH-values greater than 4, particularly at higher pH values. This reduces the useful shelf life of the vessel as its barrier efficacy is reduced.

Consider more particularly evacuated blood sample collection tubes, which are sold with the lumen evacuated. The vacuum is used to draw blood from a patient into the tube, and the level of vacuum determines its draw volume capacity—how much blood the tube can draw before the pressure is equalized and flow stops. Evacuated blood sample collection tubes made of polymeric thermoplastic material are permeable to atmospheric gases such as air or its component gases such as oxygen and nitrogen, which reduce the vacuum level within the tube as time passes. If the vacuum is reduced too much, insufficient blood will be drawn to meet the specifications of the sample tube. A common specification is that, throughout its shelf life, the evacuated blood sample collection tube must maintain a draw volume capacity of at least 90% of the draw volume capacity of a newly evacuated vessel of the same kind. A barrier coating or layer is useful to prevent atmospheric gases from entering the thermoplastic polymeric vessel during its shelf life and thus provide a tube that meets this specification over a desirably long shelf life.

Many such sample tubes also contain a reagent which is introduced at the time of manufacture and remains in the lumen until blood or another sample is introduced and contacted with the reagent. The reagent may be in contact with the vessel wall and any coatings on the wall for as long as the shelf life of the sample collection tube. Many such aqueous reagents, for example the buffered sodium citrate reagent commonly used to prevent coagulation of blood introduced into the blood sample collection tube, may damage the SiOx barrier coating or layer if directly in contact with the barrier coating or layer. Consequently, it has been found useful to apply over the barrier protective coating or layer a pH protective coating or layer to prevent direct contact between the barrier coating or layer and the reagent or other contents in the lumen.

BRIEF SUMMARY OF THE INVENTION

An aspect of the invention is a method of processing a vessel to apply a tie coating or layer (289), a barrier coating or layer, and optionally one or more additional coatings or layers.

To carry out the process, a vessel is provided including a wall consisting essentially of thermoplastic polymeric material defining a lumen. The wall has an inside surface (303) facing the lumen and an outside surface.

During the process, a partial vacuum is drawn in the lumen. While maintaining the partial vacuum unbroken in the lumen, a tie coating or layer of SiOxCy is applied by a tie PECVD coating process. The tie PECVD coating process is carried out by applying sufficient power to generate plasma within the lumen while feeding a gas suitable for forming the coating. The gas feed includes a linear siloxane precursor, optionally oxygen, and optionally an inert gas diluent. The values of x and y are as determined by X-ray photoelectron spectroscopy (XPS). Then, while maintaining the partial vacuum unbroken in the lumen, the plasma is extinguished. A tie coating or layer of SiOxCy, for which x is from about 0.5 to about 2.4 and y is from about 0.6 to about 3, is produced on the inside surface as a result.

Later during the process, while maintaining the partial vacuum unbroken in the lumen, a barrier coating or layer is applied by a barrier PECVD coating process. The barrier PECVD coating process is carried out by applying sufficient power to generate plasma within the lumen while feeding a gas. The gas feed includes a linear siloxane precursor and oxygen. A barrier coating or layer of SiOx, wherein x is from 1.5 to 2.9 as determined by XPS is produced between the tie coating or layer and the lumen as a result.

Then optionally, while maintaining the partial vacuum unbroken in the lumen, the plasma is extinguished.

Later, as a further option, a pH protective coating or layer of SiOxCy can be applied. In this formula as well, x is from about 0.5 to about 2.4 and y is from about 0.6 to about 3, each as determined by XPS. The pH protective coating or layer is optionally applied between the barrier coating or layer and the lumen, by a pH protective PECVD coating process. This process includes applying sufficient power to generate plasma within the lumen while feeding a gas including a linear siloxane precursor, optionally oxygen, and optionally an inert gas diluent.

As a result of this processing, a coated vessel is produced having a lower gas permeation rate constant into the lumen than a corresponding vessel made by the same process except breaking the partial vacuum in the lumen between applying the tie coating or layer and applying the barrier coating or layer.

Another aspect of the invention is an evacuated blood collection tube made according to any of the methods described above.

Another aspect of the invention is a coated vessel comprising a wall, a tie coating or layer, a barrier coating or layer, and optionally a pH protective coating or layer, made by the process defined below.

The wall consists essentially of thermoplastic polymeric material defining a lumen. The wall has an interior surface facing the lumen and an exterior surface.

The tie coating or layer consists essentially of SiOxCy, wherein x is from about 0.5 to about 2.4 and y is from about 0.6 to about 3, each as determined by X-ray photoelectron spectroscopy (XPS), on the interior surface.

The barrier coating or layer consists essentially of SiOx, wherein x is from 1.5 to 2.9 as determined by XPS, between the tie coating or layer and the lumen.

The optional pH protective coating or layer consists essentially of SiOxCy, wherein x is from about 0.5 to about 2.4 and y is from about 0.6 to about 3, each as determined by XPS, between the barrier coating or layer and the lumen.

The coated vessel is formed by a process comprising several steps. A vessel is provided comprising the wall. A partial vacuum is drawn in the lumen. While maintaining the partial vacuum unbroken in the lumen, the tie coating or layer of SiOxCy is applied by a tie PECVD process comprising applying sufficient power (alternatively the same concept is referred to in this specification as "energy") to generate plasma within the lumen while feeding a gas comprising a linear siloxane precursor, optionally oxygen, and optionally an inert gas diluent.

Then, while maintaining the partial vacuum unbroken in the lumen, the plasma is extinguished. After that, while still maintaining the partial vacuum unbroken in the lumen, the barrier coating or layer is applied by a barrier PECVD process comprising applying sufficient power to generate plasma within the lumen while feeding a gas comprising a linear siloxane precursor and oxygen.

If the optional pH protective coating or layer is applied, this may optionally be done according to the following process.

Optionally after applying the barrier coating or layer, while maintaining the partial vacuum unbroken in the lumen, the plasma is extinguished.

Then optionally, while maintaining the partial vacuum unbroken in the lumen, the pH protective coating or layer of SiOxCy is applied by a pH protective PECVD process. The pH protective PECVD process comprises applying sufficient power to generate plasma within the lumen while feeding a gas comprising a linear siloxane precursor, optionally oxygen, and optionally an inert gas diluent.

The result of the process is a coated vessel.

Surprisingly, the coated vessel made by this process has a lower gas permeation rate constant into the lumen than a corresponding vessel made by the same process except breaking the partial vacuum in the lumen between applying the tie coating or layer and applying the barrier coating or layer. Alternatively, the coated vessel made by this process including the optional steps has a lower gas permeation rate constant into the lumen than a corresponding vessel made by the same process except breaking the partial vacuum in the lumen between applying the tie coating or layer and the barrier coating or layer, and also breaking the partial vacuum in the lumen between applying the barrier coating or layer and the pH protective coating or layer.

Another aspect of the invention is an evacuated blood collection tube comprising a coated vessel as defined above and a closure sealing the lumen. The lumen has a vacuum level sufficient to draw blood from a patient's vein into the lumen.

Still another aspect of the invention is an evacuated blood collection tube which can be a thermoplastic vessel wall having a top defining an opening, an inside surface defining a lumen, an outside surface, and a stopper contact area on the inside surface adjacent to the top. The stopper contact area is tapered inward from 0 to 1.3 degrees.

A still further aspect of the invention is an evacuated blood collection tube including: a thermoplastic vessel wall having a top, an inside surface defining a lumen, and an outside surface. A retention lip projects radially inward from the inside surface. The inside surface includes a stopper contact area adjacent to and below the retention lip.

Further aspects, features, and embodiments of the invention are provided in the following description and claims.

Figure 1:
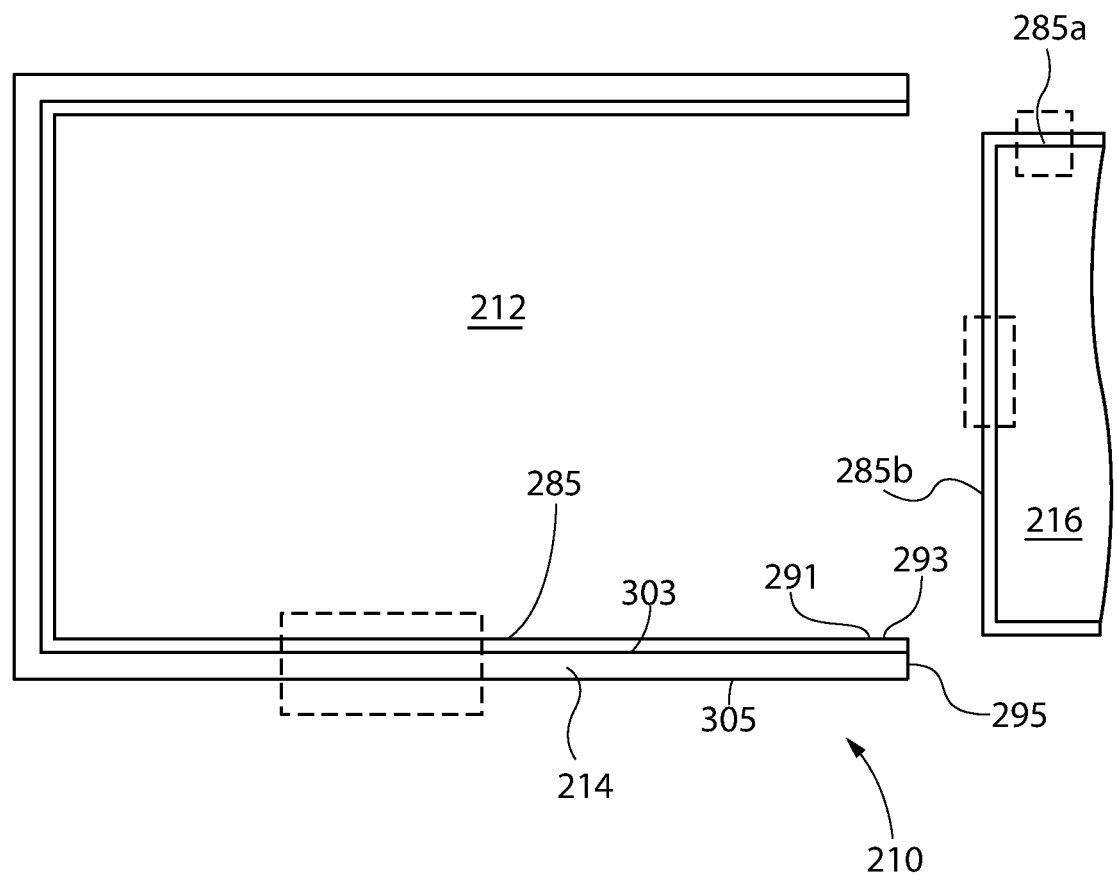
FIG. 1 is a schematic sectional view of a vessel according to any embodiment of the invention.

The following reference characters are used in the drawing figures:

| | |
|---|---|
| 210 | Pharmaceutical package or vessel |
| 212 | Lumen |
| 214 | Wall |
| 216 | Closure |
| 285 | Vessel coating or layer set |
| 286 | pH protective coating or layer |
| 288 | Barrier coating or layer |
| 289 | Tie coating or layer |
| 291 | Stopper contact area (of 210) |
| 293 | Retention lip |
| 295 | Top (of 210) |
| 297 | Lower end (of 293) |
| 299 | Lower ramp |
| 301 | Upper ramp |
| 303 | Inside surface (of 214) |
| 305 | Outside surface (of 214) |
| 307 | Lower end (of 301) |

Definitions

In the context of the present invention, the following definitions and abbreviations are used:

RF is radio frequency.

The term "at least" in the context of the present invention means "equal or more" than the integer following the term. The word "comprising" does not exclude other elements or steps, and the indefinite article "a" or "an" does not exclude a plurality unless indicated otherwise. Whenever a parameter range is indicated, it is intended to disclose the parameter values given as limits of the range and all values of the parameter falling within said range.

"First" and "second" or similar references to anything refer to the minimum number of such things that are present, but do not necessarily represent the order or total number of such things or require additional such things beyond the stated number. For example, a "first" deposit in the context of this specification can be either the only deposit or any one of plural deposits, without limitation. In other words, recitation of a "first" deposit allows but does not require an embodiment that also has a second or further deposit.

For purposes of the present invention, an "organosilicon precursor" is a compound having at least one of the linkages:

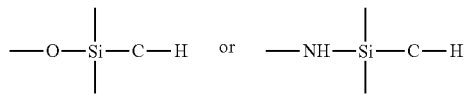

which is a tetravalent silicon atom connected to an oxygen or nitrogen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane; a linear silazane, a monocyclic silazane, a polycyclic silazane, a polysilsesquiazane, and a combination of any two or more of these precursors.

The feed amounts of PECVD precursors, gaseous reactant or process gases, and carrier gas are sometimes expressed in "standard volumes" in the specification and claims. The standard volume of a charge or other fixed amount of gas is the volume the fixed amount of the gas would occupy at a standard temperature and pressure (without regard to the actual temperature and pressure of delivery). Standard volumes can be measured using different units of volume, and still be within the scope of the present disclosure and claims. For example, the same fixed amount of gas could be expressed as the number of standard cubic centimeters, the number of standard cubic meters, or the number of standard cubic feet. Standard volumes can also be defined using different standard temperatures and pressures, and still be within the scope of the present disclosure and claims. For example, the standard temperature might be 0° C. and the standard pressure might be 760 Torr (as is conventional), or the standard temperature might be 20° C. and the standard pressure might be 1 Torr. But whatever standard is used in a given case, when comparing relative amounts of two or more different gases without specifying particular parameters, the same units of volume, standard temperature, and standard pressure are to be used relative to each gas, unless otherwise indicated.

The corresponding feed rates of PECVD precursors, gaseous reactant or process gases, and carrier gas are expressed in standard volumes per unit of time in the specification. For example, in the working examples the flow rates are expressed as standard cubic centimeters per minute, abbreviated as sccm. As with the other parameters, other units of time can be used, such as seconds or hours, but consistent parameters are to be used when comparing the flow rates of two or more gases, unless otherwise indicated.

A "vessel" in the context of the present invention can be any type of vessel with a wall defining an inner or interior surface. Though the invention is not necessarily limited to sample collection tubes, pharmaceutical packages, or other vessels of a particular volume, pharmaceutical packages or other vessels are contemplated in which the lumen has a void volume of from 0.5 to 250 mL, optionally from 1 to 20 mL, optionally from 0.5 to 12 mL, optionally from 1 to 3 mL. The substrate surface can be part or all of the inner or interior surface of a vessel having at least one opening and an inner or interior surface. Some examples of pharmaceutical and other packages and vessels include, but are not limited to, a sample collection tube, an evacuated blood sample collection tube (which commonly is provided in a small size containing about 6 mL or a large size containing about 12 mL), a sample storage tube, a vial, a plastic-coated vial, a syringe, a plastic coated syringe, a blister pack, an ampoule, a plastic coated ampoule, a cartridge, a bottle, a plastic coated bottle, a centrifuge tube, a chromatography vial, tubing, a pouch, a pump, a sprayer, a stopper, a needle, a plunger, a cap, a stent, a catheter or an implant.

Additionally, a vessel according to the present invention can be a sample tube, for example for collecting or storing biological fluids like blood or urine, a syringe part, for example a syringe barrel, for storing or delivering a biologically active compound or composition, for example a medicament or pharmaceutical composition, a vial for storing biological materials or biologically active compounds or compositions, a pipe or tubing, for example a catheter for transporting biological materials or biologically active compounds or compositions, or a cuvette for holding fluids, for example for holding biological materials or biologically active compounds or compositions.

A vessel can be of any shape. A vessel having a substantially cylindrical wall adjacent to at least one of its open ends is preferred. Generally, the interior wall of the vessel is cylindrically shaped, like, for example in a sample tube or a syringe barrel. Sample tubes and syringes or their parts (for example syringe barrels) are contemplated.

The values of w, x, y, and z are applicable to the empirical composition $Si_wO_xC_yH_z$ throughout this specification, and the same values of x and y are applicable to the empirical composition $SiO_xC_y$ throughout this specification. The values of w, x, y, and z should be understood as ratios or an empirical formula (for example for a coating or layer), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$.

The atomic ratio of $Si_wO_xC_yH_z$ can only be partially determined by XPS, since H atoms are not detectable by XPS. Hydrogen atoms are, however, detectable using a different analysis, for example Rutherford Backscattering or Rutherford Forward Scattering. A particular coating or layer may thus in one aspect be expressed by the formula $Si_wO_xC_yH_z$, for example where w is 1, x is from about 0.5 to about 2.4, y is from about 0.6 to about 3, and z is from about 2 to about 9. The same particular coating or layer can alternatively be characterized by XPS only, without accounting for hydrogen, and thus expressed by the formula $SiO_xC_y$, in which x is from about 0.5 to about 2.4 and y is from about 0.6 to about 3. $SiO_xC_y$, has no subscript following Si, which has the same meaning as a subscript w of 1 in the formula $Si_wO_xC_yH_z$. In this specification, XPS is generally used without accounting for hydrogen, and the atomic ratio is expressed as $SiO_xC_y$. Typically, such coating or layer would hence contain 36% to 41% carbon normalized to 100% carbon plus oxygen plus silicon.

The term "syringe" is broadly defined to include cartridges, injection "pens," and other types of barrels or reservoirs adapted to be assembled with one or more other components to provide a functional syringe. "Syringe" is also broadly defined to include related articles such as auto-injectors, which provide a mechanism for dispensing the contents.

Processing a vessel "while maintaining the partial vacuum unbroken in the lumen" of a vessel means continuing processing of the vessel without introducing sufficient gas into the lumen to bring its pressure to substantially, exactly, or more than ambient atmospheric pressure.

The gas permeation rate constant into the lumen (abbreviated as GPRC) is a characteristic of the vessel wall, and means the instantaneous rate of permeation of the atmosphere or some other specified gas (in μmol or micromoles per day) from outside a closed container into the lumen of the container through its wall, for a wall surface area of 1 cm2 and a gas partial pressure difference of 1 atmosphere (standard atmosphere pressure) across the wall. The gas permeation rate constant can be measured in units of μmol/(day×cm2×atm.) This term does not include gas bypassing the wall, as by leaking between the wall and a closure or permeating through the closure.

"The coated vessel having lower gas permeation rate constant into the lumen than a corresponding vessel made by the same process except breaking the partial vacuum in the lumen between applying the adhesion coating or layer and applying the barrier coating or layer" is largely self-explanatory. In the context of this language, "breaking the partial vacuum in the lumen" means introducing sufficient gas into the lumen to bring its pressure to substantially, exactly, or more than ambient atmospheric pressure.

The shelf life of a vessel is defined as the period of time after the date of manufacture when the vessel can be used and function properly. For example, the shelf life of an evacuated blood collection tube is the period of time after the date of evacuation when the evacuated blood collection tube maintains a draw volume capacity of at least 90% of the draw volume capacity of a newly evacuated vessel of the same kind.

The change in draw volume capacity can be measured directly by a physical measurement of draw volume versus time, or it can be estimated by applying a multiplier to the oxygen permeation rate constant (OPRC) to account for the nitrogen permeation rate constant of the vessel in question, then determining the combined oxygen plus nitrogen permeation rate constant. The remaining gases in ambient air are usually too dilute to be determined for this calculation.

As a rule of thumb, the ratio of nitrogen and oxygen permeation rate constants is fairly constant for a wide range of polymers (D. W. van Krevelen, Properties of Polymers, 1990, Table 18.6). The permeation rate constant of oxygen is about 3.8 times the permeation rate constant of nitrogen in the same polymer.

TABLE 18.6

Relative values of permeability parameters (Rules of thumb)

| Gas | P | D | S | $E_P$ | $E_D$ |
|---|---|---|---|---|---|
| $N_2$ = 1) | 1 | 1 | 1 | 1 | 1 |
| CO | 1.2 | 1.1 | 1.1 | 1 | 1 |
| $CH_4$ | 3.4 | 0.7 | 4.9 | (1) | (1) |
| $O_2$ | 3.8 | 1.7 | 2.2 | 0.86 | 0.90 |
| He | 15 | 60 | 0.25 | 0.62 | 0.45 |
| $H_2$ | 22.5 | 30 | 0.75 | 0.70 | 0.65 |
| $CO_2$ | 24 | 1 | 24 | 0.75 | 1.03 |
| $H_2O$ | (550) | 5 | — | 0.75 | 0.75 |

DETAILED DESCRIPTION OF THE INVENTION

The present invention will now be described more fully, with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout. The following disclosure relates to all embodiments unless specifically limited to a certain embodiment.

Vessels and Coating Sets

The contemplated coated vessel, including the vessel illustrated in FIGS. 1, 2, and 4-6, comprises a wall 214 and a vessel coating or layer set 285, comprising a tie coating or layer 289, a barrier coating or layer 288, and optionally a pH protective coating or layer 286 on at least a portion of the wall 214 facing the lumen 212, made by the process defined below.

Figure 2:
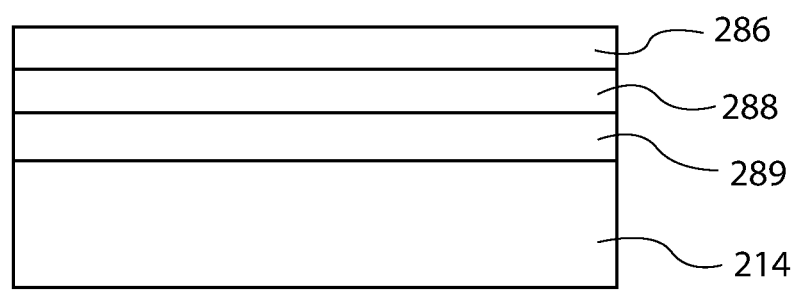
FIG. 2 is an enlarged detail view of a portion of the vessel wall and coatings of FIG. 1.

The vessel may be more specifically a sample collection tube such as an evacuated blood collection tube, a vial, a syringe, a blister pack, an ampoule, a cartridge, a bottle, a pouch, a pump, a sprayer, a stopper, a needle, a plunger, a cap, a stent, a catheter or an implant, or any other type of container or conduit for a fluid. FIGS. 1 and 2 show a vessel having at least a single opening, and should be understood to include a vessel having two or more openings, such as a syringe, or a vessel having no openings, such as a pouch, blister pack, or ampoule. The wall can be made of any thermoplastic polymeric material, which optionally comprises a polyester, polyethylene terephthalate (PET), polyethylene naphthalate (PEN); a polyolefin, cyclic olefin polymer (COP), cyclic olefin copolymer (COC), polypropylene (PP), or a polycarbonate, preferably COP. If water permeability is less important than oxygen permeability, a PET wall is expressly contemplated, as PET has more water permeability but roughly an order of magnitude less oxygen permeability than COP.

An embodiment of the vessel coating or layer set 285 is at least one tie coating or layer 289, at least one barrier coating or layer 288, and at least one pH protective coating or layer 286 (which is optional), illustrated in FIGS. 1, 2. This embodiment of the vessel coating or layer set with all three coatings is sometimes known as a "trilayer coating" in which the barrier coating or layer 288 of SiOx is protected against contents having a pH otherwise high enough to remove it by being sandwiched between the pH protective coating or layer 286 and the tie coating or layer 289, each an organic layer of SiOxCy as defined in this specification. Specific examples of this trilayer coating is provided in this specification.

Figure 7:
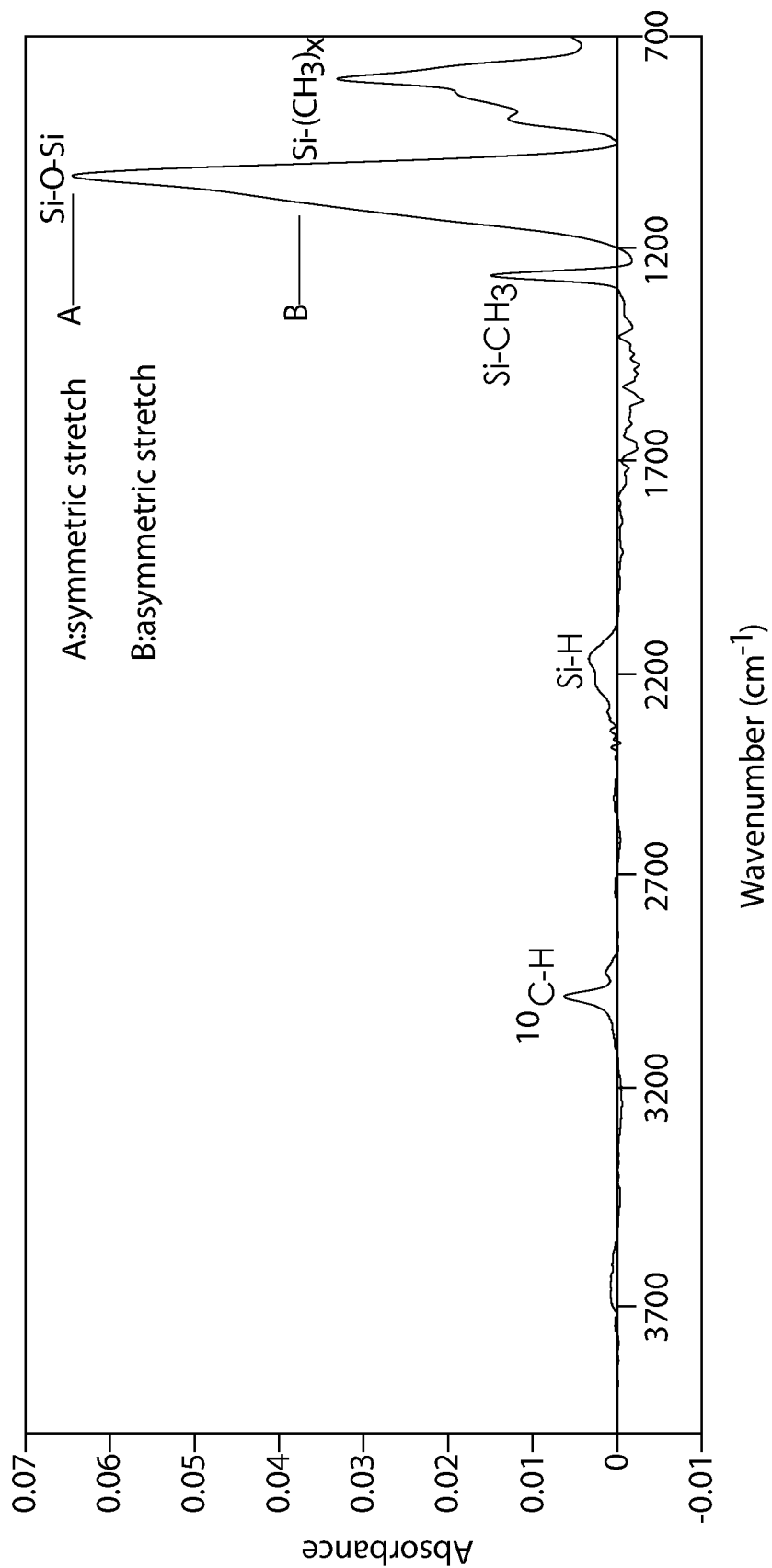
FIG. 7 is a Fourier Transform Infrared Spectrophotometer (FTIR) plot for a pH protective layer made according to the present description.

In addition to its average atomic proportions expressed by the formula SiOxCy, the pH protective coating or layer 286 can be characterized by its FTIR spectrum, a representative example of which is shown in FIG. 7. The peak assignments for the pH protective coating or layer 286 are:

| Chemical Bonds | Wavenumber (cm−1) |
|---|---|
| Si—O—Si (asymmetric stretch) | 1080-1200 |
| Si—O—Si (symmetric stretch) | 1020-1080 |
| C—H | 2960 |
| Si—H | 2100 |
| Si—CH3 | 1273 |
| Si—(CH3)$_x$ | 800-830 |

Commonly in the FTIR spectrum for the pH protective coating or layer 286, the Si—O—Si symmetric stretch and asymmetric stretch peaks appear to merge, forming a simple peak, while in the spectra for lubricity coatings (referred to for example in U.S. Pat. No. 7,985,188) the Si—O—Si symmetric stretch and asymmetric stretch peaks form a compound peak having a shoulder on the lower wave number side (the right side in FIG. 7), the shoulder being indicative of asymmetric stretch.

The contemplated thicknesses of the respective layers in nm (preferred ranges in parentheses) are given in the Trilayer Thickness Table 1.

| Trilayer Thickness Table 1 | | |
|---|---|---|
| Adhesion | Barrier | Protection |
| 5-100 | 20-200 | 50-500 |
| (5-20) | (20-30) | (100-200) |

The trilayer coating set 285 optionally includes as a first layer an adhesion or tie coating or layer 289 that improves adhesion of the barrier coating or layer to the COP substrate. The adhesion or tie coating or layer 289 is also believed to relieve stress on the barrier coating or layer 288, making the barrier layer less subject to damage from thermal expansion or contraction or mechanical shock. The adhesion or tie coating or layer 289 is also believed to decouple defects between the barrier coating or layer 288 and the COP substrate. This is believed to occur because any pinholes or other defects that may be formed when the adhesion or tie coating or layer 289 is applied tend not to be continued when the barrier coating or layer 288 is applied, so the pinholes or other defects in one coating do not line up with defects in the other. The adhesion or tie coating or layer 289 has some efficacy as a barrier layer, so even a defect providing a leakage path extending through the barrier coating or layer 289 is blocked by the adhesion or tie coating or layer 289.

The trilayer coating set 285 includes as a second layer a barrier coating or layer 288 that provides a barrier to oxygen that has permeated the COP barrel wall. The barrier coating or layer 288 also is a barrier to extraction of the composition of the barrel wall 214 by the contents of the lumen 214.

The trilayer coating set 285 optionally includes as a third layer a pH protective coating or layer 286 that provides protection of the underlying barrier coating or layer 288 against contents of the vessel having a pH from 4 to 8 or more, including where a surfactant is present. For a prefilled vessel that is in contact with the contents of the vessel from the time it is manufactured to the time it is used, the pH protective coating or layer 286 prevents or inhibits attack of the barrier coating or layer 288 sufficiently to maintain an effective oxygen barrier over the intended shelf life of the prefilled vessel.

The rate of erosion, dissolution, extraction, or leaching (different names for related concepts) of the pH protective coating or layer 286, if directly contacted by a fluid having a pH of from 5 to 9, is less than the rate of erosion of the barrier coating or layer 288, if directly contacted by the fluid having a pH of from 5 to 9. The pH protective coating or layer 286 is effective to isolate a fluid 218 having a pH between 5 and 9 from the barrier coating or layer 288, at least for sufficient time to allow the barrier coating to act as a barrier during the shelf life of the pharmaceutical package or other vessel 210.

Oxygen permeation rate constant (OPRC) is deemed appropriate to verify integrity of barrier coatings.

Tie Coating or Layer

The tie coating or layer consists essentially of SiOxCy, wherein x is from about 0.5 to about 2.4 and y is from about 0.6 to about 3, each as determined by X-ray photoelectron spectroscopy (XPS), on the interior surface.

The tie coating or layer 289 has at least two functions. One function of the tie coating or layer 289 is to improve adhesion of a barrier coating or layer 288 to a substrate, in particular a thermoplastic substrate, although a tie layer can be used to improve adhesion to a glass substrate or to another coating or layer. For example, a tie coating or layer, also referred to as an adhesion layer or coating, can be applied to the substrate and the barrier layer can be applied to the adhesion layer to improve adhesion of the barrier layer or coating to the substrate.

Another function of the tie coating or layer 289 has been discovered: a tie coating or layer 289 applied under a barrier coating or layer 288 can improve the function of a pH protective coating or layer 286 applied over the barrier coating or layer 288.

The tie coating or layer 289 can be composed of, comprise, or consist essentially of SiOxCy, in which x is between 0.5 and 2.4 and y is between 0.6 and 3. The atomic ratios of Si, 0, and C in the tie coating or layer 289 are, as several options:

Si 100: O 50-150: C 90-200 (i.e. w=1, x=0.5 to 1.5, y=0.9 to 2);
Si 100: O 70-130: C 90-200 (i.e. w=1, x=0.7 to 1.3, y=0.9 to 2)
Si 100: O 80-120: C 90-150 (i.e. w=1, x=0.8 to 1.2, y=0.9 to 1.5)
Si 100: O 90-120: C 90-140 (i.e. w=1, x=0.9 to 1.2, y=0.9 to 1.4), or
Si 100: O 92-107: C 116-133 (i.e. w=1, x=0.92 to 1.07, y=1.16 to 1.33) The atomic ratio can be determined by XPS.

Optionally, the tie coating or layer can be similar or identical in composition with the pH protective coating or layer 286 described elsewhere in this specification, although this is not a requirement.

The tie coating or layer 289 is contemplated in any embodiment generally to be from 5 nm to 100 nm thick, preferably from 5 to 20 nm thick, particularly if applied by chemical vapor deposition. These thicknesses are not critical.

Commonly but not necessarily, the tie coating or layer 289 will be relatively thin, since its function is to change the surface properties of the substrate.

Barrier Layer

The barrier coating or layer consists essentially of SiOx, wherein x is from 1.5 to 2.9 as determined by XPS, between the tie coating or layer and the lumen.

A barrier coating or layer 288 optionally can be deposited by plasma enhanced chemical vapor deposition (PECVD) or other chemical vapor deposition processes on the vessel of a pharmaceutical package, in particular a thermoplastic package, to prevent oxygen, carbon dioxide, or other gases from entering the vessel and/or to prevent leaching of the pharmaceutical material into or through the package wall.

The barrier coating or layer for any embodiment defined in this specification (unless otherwise specified in a particular instance) is a coating or layer, optionally applied by PECVD as indicated in U.S. Pat. No. 7,985,188. The barrier layer optionally is characterized as an "SiOx" coating, and contains silicon, oxygen, and optionally other elements, in which x, the ratio of oxygen to silicon atoms, is from about 1.5 to about 2.9, or 1.5 to about 2.6, or about 2. These alternative definitions of x apply to any use of the term SiOx in this specification. The barrier coating or layer is applied, for example to the interior of a pharmaceutical package or other vessel, for example a sample collection tube, a syringe barrel, a vial, or another type of vessel.

The barrier coating 288 comprises or consists essentially of SiOx, wherein x is from 1.5 to 2.9, from 2 to 1000 nm thick, the barrier coating 288 of SiOx having an interior surface 220 facing the lumen 212 and an outer surface 222 facing the wall 214 article surface 254, the barrier coating 288 being effective to reduce the ingress of atmospheric gas into the lumen 212 compared to an uncoated vessel 250. One suitable barrier composition is one where x is 2.3, for example. For example, the barrier coating or layer such as 288 of any embodiment can be applied at a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The barrier coating or layer can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Ranges of 20-200 nm, optionally 20-30 nm, are contemplated. Specific thickness ranges composed of any one of the minimum thicknesses expressed above, plus any equal or greater one of the maximum thicknesses expressed above, are expressly contemplated.

The thickness of the SiOx or other barrier coating or layer can be measured, for example, by transmission electron microscopy (TEM), and its composition can be measured by X-ray photoelectron spectroscopy (XPS). The primer coating or layer described herein can be applied to a variety of pharmaceutical packages or other vessels made from plastic or glass, for example to plastic tubes, vials, and syringes.

A barrier coating or layer 286 of SiOx, in which x is between 1.5 and 2.9, is applied by plasma enhanced chemical vapor deposition (PECVD) directly or indirectly to the thermoplastic wall 214 (for example a tie coating or layer 289 can be interposed between them) so that in the filled pharmaceutical package or other vessel 210 the barrier coating or layer 286 is located between the inner or interior surface 220 of the thermoplastic wall 214 and the fluid 218.

The barrier coating or layer 286 of SiOx is supported by the thermoplastic wall 214. The barrier coating or layer 286 as described elsewhere in this specification, or in U.S. Pat. No. 7,985,188, can be used in any embodiment.

Certain barrier coatings or layers 286 such as SiOx as defined here have been found to have the characteristic of being subject to being measurably diminished in barrier improvement factor in less than six months as a result of attack by certain relatively high pH contents of the coated vessel as described elsewhere in this specification, particularly where the barrier coating or layer directly contacts the contents. This issue can be addressed using a pH protective coating or layer as discussed in this specification.

pH Protective Coating or Layer

The optional pH protective coating or layer consists essentially of SiOxCy, wherein x is from about 0.5 to about 2.4 and y is from about 0.6 to about 3, each as determined by XPS, between the barrier coating or layer and the lumen.

The inventors have found that barrier layers or coatings of SiOx are eroded or dissolved by some fluids, for example aqueous compositions having a pH above about 4, alternatively above about 5. Since coatings applied by chemical vapor deposition can be very thin—tens to hundreds of nanometers thick—even a relatively slow rate of erosion can remove or reduce the effectiveness of the barrier layer in less time than the desired shelf life of a product package. This is particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the SiOx coating. Optionally, this problem can be addressed by protecting the barrier coating or layer 288, or other pH sensitive material, with a pH protective coating or layer 286.

Optionally, the pH protective coating or layer 286 can be composed of, comprise, or consist essentially of SiwOxCyHz (or its equivalent SiOxCy) or SiwNxCyHz or its equivalent Si(NH)xCy). The atomic ratio of Si:O: C or Si:N:C can be determined by XPS (X-ray photoelectron spectroscopy). The pH protective coating or layer may thus in one aspect have the formula SiOxCy, where x is from about 0.5 to about 2.4 and y is from about 0.6 to about 3. The same pH protective coating or layer may thus in another aspect have the formula SiOxCyHz, where x is from about 0.5 to about 2.4 and y is from about 0.6 to about 3, and z is from about 2 to about 9.

Typically, expressed as the formula SiwOxCy, where w=1, the atomic ratios of Si, 0, and C are, as several options:
  Si 100: O 50-150: C 90-200 (i.e. w=1, x=0.5 to 1.5, y=0.9 to 2);
  Si 100: O 70-130: C 90-200 (i.e. w=1, x=0.7 to 1.3, y=0.9 to 2)
  Si 100: O 80-120: C 90-150 (i.e. w=1, x=0.8 to 1.2, y=0.9 to 1.5)
  Si 100: O 90-120: C 90-140 (i.e. w=1, x=0.9 to 1.2, y=0.9 to 1.4)
  Si 100: O 92-107: C 116-133 (i.e. w=1, x=0.92 to 1.07, y=1.16 to 1.33), or
  Si 100: O 80-130: C 90-150.

Alternatively, the pH protective coating or layer can have atomic concentrations normalized to 100% carbon, oxygen, and silicon, as determined by X-ray photoelectron spectroscopy (XPS) of less than 50% carbon and more than 25% silicon. Alternatively, the atomic concentrations are from 25 to 45% carbon, 25 to 65% silicon, and 10 to 35% oxygen. Alternatively, the atomic concentrations are from 30 to 40% carbon, 32 to 52% silicon, and 20 to 27% oxygen. Alternatively, the atomic concentrations are from 33 to 37% carbon, 37 to 47% silicon, and 22 to 26% oxygen.

The thickness of the pH protective coating or layer can be, for example, from 10 nm to 1000 nm; alternatively from 10 nm to 1000 nm; alternatively from 10 nm to 900 nm; alternatively from 10 nm to 800 nm; alternatively from 10 nm to 700 nm; alternatively from 10 nm to 600 nm; alternatively from 10 nm to 500 nm; alternatively from 10 nm to 400 nm; alternatively from 10 nm to 300 nm; alternatively from 10 nm to 200 nm; alternatively from 10 nm to 100 nm; alternatively from 10 nm to 50 nm; alternatively from 20 nm to 1000 nm; alternatively from 50 nm to 1000 nm; alternatively from 10 nm to 1000 nm; alternatively from 50 nm to 800 nm; alternatively from 100 nm to 700 nm; alternatively from 300 to 600 nm.

Optionally, the atomic concentration of carbon in the protective layer, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the pH protective coating or layer can be increased in comparison to the organosilicon precursor, and/or the atomic ratio of oxygen to silicon can be decreased in comparison to the organosilicon precursor.

Optionally, the pH protective coating or layer can have an atomic concentration of silicon, normalized to 100% of carbon, oxygen, and silicon, as determined by X-ray photoelectron spectroscopy (XPS), less than the atomic concentration of silicon in the atomic formula for the feed gas. For example, embodiments are contemplated in which the atomic concentration of silicon decreases by from 1 to 80 atomic percent, alternatively by from 10 to 70 atomic percent, alternatively by from 20 to 60 atomic percent, alternatively by from 30 to 55 atomic percent, alternatively by from 40 to 50 atomic percent, alternatively by from 42 to 46 atomic percent.

As another option, a pH protective coating or layer is contemplated in any embodiment that can be characterized by a sum formula wherein the atomic ratio C:O can be increased and/or the atomic ratio Si:O can be decreased in comparison to the sum formula of the organosilicon precursor.

The pH protective coating or layer 286 commonly is located between the barrier coating or layer 288 and the fluid 218 in the finished article. The pH protective coating or layer 286 is supported by the thermoplastic wall 214.

The pH protective coating or layer 286 optionally is effective to keep the barrier coating or layer 288 at least substantially undissolved as a result of attack by the fluid 218 for a period of at least six months.

The pH protective coating or layer can have a density between 1.25 and 1.65 g/cm3, alternatively between 1.35 and 1.55 g/cm3, alternatively between 1.4 and 1.5 g/cm3, alternatively between 1.4 and 1.5 g/cm3, alternatively between 1.44 and 1.48 g/cm3, as determined by X-ray reflectivity (XRR). Optionally, the organosilicon compound can be octamethylcyclotetrasiloxane and the pH protective coating or layer can have a density which can be higher than the density of a pH protective coating or layer made from HMDSO as the organosilicon compound under the same PECVD reaction conditions.

The pH protective coating or layer optionally can prevent or reduce the precipitation of a compound or component of a composition, in particular can prevent or reduce insulin precipitation or blood clotting, in comparison to the uncoated surface and/or to a barrier coated surface using HMDSO as precursor.

The pH protective coating or layer optionally can have an RMS surface roughness value (measured by AFM) of from about 5 to about 9, optionally from about 6 to about 8, optionally from about 6.4 to about 7.8. The Ra surface roughness value of the pH protective coating or layer, measured by AFM, can be from about 4 to about 6, optionally from about 4.6 to about 5.8. The Rmax surface roughness value of the pH protective coating or layer, measured by AFM, can be from about 70 to about 160, optionally from about 84 to about 142, optionally from about 90 to about 130.

The interior surface of the pH protective optionally can have a contact angle (with distilled water) of from 90° to 110°, optionally from 80° to 120°, optionally from 70° to 130°, as measured by Goniometer Angle measurement of a water droplet on the pH protective surface, per ASTM D7334-08 "Standard Practice for Surface Wettability of Coatings, Substrates and Pigments by Advancing Contact Angle Measurement."

The passivation layer or pH protective coating or layer 286 ("passivation layer" and "pH protective coating or layer" are two different names for the same thing) optionally shows an O-Parameter measured with attenuated total reflection (ATR) Fourier-transform infrared spectrometry (FTIR) of less than 0.4, measured as:

$$\text{O-Parameter} = \frac{\text{Intensity at } 1253 \text{ cm}^{-1}}{\text{Maximum intensity in the range } 1000 \text{ to } 1100 \text{ cm}^{-1}}$$

The O-Parameter is defined in U.S. Pat. No. 8,067,070, which claims an O-parameter value of most broadly from 0.4 to 0.9. It can be measured from physical analysis of an FTIR amplitude versus wave number plot to find the numerator and denominator of the above expression. The O-Parameter can also be measured from digital wave number versus absorbance data.

U.S. Pat. No. 8,067,070 asserts that the claimed O-parameter range provides a superior pH protective coating or layer. Surprisingly, it has been found by the present inventors that 0-parameters outside the ranges claimed in U.S. Pat. No. 8,067,070 provide better results than are obtained in U.S. Pat. No. 8,067,070.

Alternatively in the embodiment of FIGS. 1-2, the O-parameter has a value of from 0.1 to 0.39, or from 0.15 to 0.37, or from 0.17 to 0.35.

Even another aspect of the invention is a composite material as just described, exemplified in FIGS. 1-5, wherein the passivation layer shows an N-Parameter measured with attenuated total reflection (ATR) Fourier-transform infrared spectrometry (FTIR) of less than 0.7, measured as:

$$\text{N-Parameter} = \frac{\text{Intensity at } 840 \text{ cm}^{-1}}{\text{Intensity at } 799 \text{ cm}^{-1}}.$$

The N-Parameter is also described in U.S. Pat. No. 8,067,070, and is measured analogously to the O-Parameter except that intensities at two specific wave numbers are used—neither of these wave numbers is a range. U.S. Pat. No. 8,067,070 claims a passivation layer with an N-Parameter of 0.7 to 1.6. Again, the present inventors have made better coatings employing a pH protective coating or layer 286 having an N-Parameter lower than 0.7, as described above. Alternatively, the N-parameter has a value of at least 0.3, or from 0.4 to 0.6, or at least 0.53.

The rate of erosion, dissolution, extraction, or leaching (different names for related concepts) of the pH protective coating or layer 286, if directly contacted by the fluid 218, is less than the rate of erosion, dissolution, extraction, or leaching of the barrier coating or layer 288, if directly contacted by the fluid 218.

The thickness of the pH protective coating or layer is contemplated in any embodiment to be from 50-500 nm, with a preferred range of 100-200 nm.

The pH protective coating or layer 286 is effective to isolate the fluid 218 from the barrier coating or layer 288, at least for sufficient time to allow the barrier coating to act as a barrier during the shelf life of the pharmaceutical package or other vessel 210.

The inventors have further found that certain pH protective coatings or layers of SiOxCy or Si(NH)xCy formed from siloxane precursors, which pH protective coatings or layers have a substantial organic component, do not erode quickly when exposed to fluids, and in fact erode or dissolve more slowly when the fluids have higher pHs within the range of 5 to 9. For example, at pH 8, the dissolution rate of a pH protective coating or layer is quite slow. These pH protective coatings or layers of SiOxCy or Si(NH)xCy can therefore be used to cover a barrier layer of SiOx, retaining the benefits of the barrier layer by protecting it from the fluid in the pharmaceutical package. The protective layer is applied over at least a portion of the SiOx layer to protect the SiOx layer from contents stored in a vessel, where the contents otherwise would be in contact with the SiOx layer.

Effective SiOxCy or Si(NH)xCy pH protective coatings or layers can be deposited, for example, from linear siloxane or linear silazane precursors, for example hexamethyldisiloxane (HMDSO) or tetramethyldisiloxane (TMDSO), or from cyclic siloxane precursors, for example octamethylenecyclotetrasiloxane (OMCTS).

Optionally an FTIR absorbance spectrum of the pH protective coating or layer 286 of any embodiment has a ratio greater than 0.75 between the maximum amplitude of the Si—O—Si symmetrical stretch peak normally located between about 1000 and 1040 cm-1, and the maximum amplitude of the Si—O—Si asymmetric stretch peak normally located between about 1060 and about 1100 cm-1. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment of the invention of FIGS. 1-5.

Optionally, for the pH protective coating or layer 286 in any embodiment, the silicon dissolution rate by a 50 mM potassium phosphate buffer diluted in water for injection, adjusted to pH 8 with concentrated nitric acid, and containing 0.2 wt. % polysorbate-80 surfactant, (measured in the absence of the medicament, to avoid changing the dissolution reagent), at 40° C., is less than 170 ppb/day. (Polysorbate-80 is a common ingredient of pharmaceutical preparations, available for example as Tween®-80 from Uniqema Americas LLC, Wilmington Del.) Alternatively contemplated dissolution reagents in the testing of this paragraph are:

a potassium phosphate buffer for pH 3;
a sodium citrate buffer for pH 6;
a potassium phosphate buffer for pH 7;
a potassium phosphate buffer for pH 8;
a tris buffer for pH 9;
a potassium phosphate buffer for pH 12.

Optionally, for the pH protective coating or layer 286 in any embodiment, the silicon dissolution rate is less than 160 ppb/day, or less than 140 ppb/day, or less than 120 ppb/day, or less than 100 ppb/day, or less than 90 ppb/day, or less than 80 ppb/day. Optionally, in any embodiment of FIGS. 13-26 the silicon dissolution rate is more than 10 ppb/day, or more than 20 ppb/day, or more than 30 ppb/day, or more than 40 ppb/day, or more than 50 ppb/day, or more than 60 ppb/day. Any minimum rate stated here can be combined with any maximum rate stated here for the pH protective coating or layer 286 in any embodiment.

Optionally, for the pH protective coating or layer 286 in any embodiment the total silicon content of the pH protective coating or layer and barrier coating, upon dissolution into a test composition with a pH of 8 from the vessel, is less than 66 ppm, or less than 60 ppm, or less than 50 ppm, or less than 40 ppm, or less than 30 ppm, or less than 20 ppm.

pH Protective Coating or Layer Properties of any Embodiment

Theory of Operation

The inventors offer the following theory of operation of the pH protective coating or layer described here. The invention is not limited by the accuracy of this theory or to the embodiments predictable by use of this theory.

The dissolution rate of the SiOx barrier layer is believed to be dependent on SiO bonding within the layer. Oxygen bonding sites (silanols) are believed to increase the dissolution rate.

It is believed that the pH protective coating or layer bonds with the SiOx barrier layer to "heal" or passivate the SiOx surface and thus dramatically reduces the dissolution rate. In this hypothesis, the thickness of the pH protective coating or layer is not the primary means of protection—the primary means is passivation of the SiOx surface. It is contemplated in any embodiment that a pH protective coating or layer as described in this specification can be improved by increasing the crosslink density of the pH protective coating or layer.

Optionally in any embodiment, each linear siloxane precursor used to deposit the tie coating or layer and the barrier coating or layer, and optionally also the pH protective coating or layer, can be hexamethylenedisiloxane (HMDSO) or tetramethylenedisiloxane (TMDSO), preferably HMDSO. Optionally in any embodiment, the same linear siloxane precursor is used in each coating process, which can be, for example the tie PECVD coating process, the barrier PECVD coating process, and optionally the pH protective PECVD coating process. Using the same siloxane allows for the use of the same coating equipment without the need for valving arrangements to feed a different siloxane, and also avoids manufacturing errors in which the wrong precursor is used in one or more coating steps, which might be difficult to detect after the coating has been applied.

Optionally in any embodiment, the technology can be further generalized to the use of any plasma enhanced chemical vapor deposition process using any precursors to generate multiple coatings, employing a process as described in this specification or claims.

Another aspect of the technology is an evacuated blood collection tube comprising a coated vessel as defined above and a closure sealing the lumen. The lumen has a vacuum level sufficient to draw blood from a patient's vein into the lumen.

Optionally in any embodiment, the evacuated blood collection tube has a shelf life of at least 6 months, the shelf life defined by maintaining at least 90% of its as-manufactured draw volume capacity.

Optionally in any embodiment, the evacuated blood collection tube has a shelf life under the same definition of at least 12 months, alternatively at least 18 months, alternatively at least 24 months, alternatively from 6 to 12 months, alternatively from 12 to 18 months, alternatively from 18 to 24 months, alternatively from 24 to 30 months, alternatively from 30 to 36 months, alternatively from 36 to 42 months. Longer shelf lives are also contemplated.

As defined here, the shelf life can be measured by the classic destructive method in which a collection of (typically) identically made evacuated blood collection tubes is exposed to external gas such as air at one atmosphere pressure or oxygen at its usual partial pressure in the atmosphere, and tested at various times for a reduction of the vacuum compared to the as-manufactured level. The shelf life can also be measured by other, typically accelerated measurement methods, for example in which the external pressure is increased, a smaller reduction in vacuum is measured after a shorter period of time and extrapolated to longer times, a test reagent or the intended contents of the tube are sealed in the tube, optionally maintained at harsher conditions known to accelerate a diminution in vacuum, and other measurement methods known in the art. One particular accelerated test method contemplated here is an oxygen permeation rate constant test.

Optionally in any embodiment, the evacuated blood collection tube has a minimum oxygen permeation rate constant (OPRC) of 0.0001, alternatively 0.00016, alternatively 0.0002, alternatively 0.0005, alternatively 0.001, alternatively 0.0016, alternatively 0.002 micromol O2/(day×cm2×atm.). Optionally in any embodiment, the evacuated blood collection tube has a maximum OPRC of 0.01, alternatively 0.005, alternatively 0.002 micromol O2/(day×cm2×atm.). Any minimum OPRC can be combined with any equal or greater maximum OPRC to construct a range.

Optionally in any embodiment, the evacuated blood collection tube has an oxygen permeation rate constant of from 0.0001 to 0.01, alternatively from 0.0002 to 0.005, alternatively from 0.0005 to 0.003, alternatively from 0.0016 to 0.003 micromol O2/(day×cm2×atm.).

Optionally in any embodiment, the evacuated blood collection tube has a fluid composition in the lumen, for example comprising a blood anticoagulation reagent. Optionally in any embodiment, the blood anticoagulation reagent comprises, for example, a citrate, for example buffered sodium citrate solution. Other reagents known for use in blood collection tubes are also contemplated for this purpose.

PECVD Process for Trilayer Coating

The PECVD trilayer coating described in this specification can be applied, for example, as follows for a 1 to 5 mL vessel such as a blood sample collection tube useful as an evacuated blood sample collection tube. Larger or smaller vessels will call for adjustments in parameters that a person of ordinary skill can carry out in view of the teaching of this specification.

The apparatus and process used is the PECVD apparatus as described generally in FIG. 2 and the accompanying text and PECVD protocols of U.S. Pat. No. 7,985,188, except that at least the tie or adhesion coating or layer and the barrier coating or layer, and optionally the pH protective layer, are applied in the same apparatus, without breaking vacuum between the application of the adhesion coating or layer and the barrier coating or layer or, optionally, between the barrier coating or layer and the pH protective coating or layer. The entire text and drawings of U.S. Pat. No. 7,985,188 is incorporated here by reference.

Examples of specific coating parameters that have been used for a 1 mL vessel and 5 mL vial are shown in the PECVD Trilayer Process Specific Parameters Tables 2 (1 mL vial) and 3 (5 mL vial):

| PECVD Trilayer Process Specific Parameters Table 2 (1 mL vessel) | | | | |
|---|---|---|---|---|
| Parameter | Units | Tie | Barrier | Protection |
| Power | W | 70 | 140 | 70 |
| TMDSO Flow | sccm | 4 | None | 4 |
| HMDSO Flow | sccm | None | 1.56 | None |
| O2 Flow | sccm | 2 | 20 | 2 |
| Argon Flow | sccm | 80 | 0 | 80 |
| Ramp Time | seconds | None | None | None |
| Deposition Time | seconds | 2.5 | 20 | 10 |
| Tube Pressure | Torr | 1 | 0.59 | 1 |

PECVD Trilayer Process
Specific Parameters Table 3 (5 mL vial)

| Parameter | Units | Adhesion | Barrier | Protection |
|---|---|---|---|---|
| Power | W | 20 | 40 | 20 |
| TMDSO Flow | sccm | 2 | 0 | 2 |
| HMDSO Flow | sccm | 0 | 3 | 0 |
| O$_2$ Flow | sccm | 1 | 50 | 1 |
| Argon Flow | sccm | 20 | 0 | 20 |
| Ramp Time | seconds | 0 | 2 | 2 |
| Deposition Time | seconds | 2.5 | 10 | 10 |
| Tube Pressure | Torr | 0.85 | 1.29 | 0.85 |

The O-parameter and N-parameter values for the pH protective coating or layer applied to the 1 mL vessel as described above are 0.34 and 0.55, respectively.

The O-parameter and N-parameter values for the pH protective coating or layer applied to the 5 mL vessel are 0.24 and 0.63, respectively.

Referring to FIGS. 1, 2, and 4-6, another aspect of the invention is a method of processing a vessel 210 to apply a tie coating or layer 289, a barrier coating or layer 288, and optionally one or more additional coatings or layers. Optionally in any embodiment, the vessel 210 can be configured as a sample collection tube, for example an evacuated blood collection tube; a sample storage tube, a centrifuge tube, a chromatography vial, or tubing. The coated vessel can be formed by a process comprising several steps.

To carry out the process, a vessel 210 is provided including a wall 214 consisting essentially of thermoplastic polymeric material defining a lumen 212. Optionally in any embodiment, the wall includes a polyester, polyethylene terephthalate (PET), polyethylene naphthalate (PEN); a polyolefin, cyclic olefin polymer (COP), cyclic olefin copolymer (COC), polypropylene (PP), or a polycarbonate, preferably COP. Optionally in any embodiment, the vessel lumen has a capacity of from 2 to 12 mL, optionally from 3 to 5 mL, optionally from 8 to 10 mL The wall 214 has an inside surface 303 facing the lumen and an outside surface 305.

A partial vacuum is drawn in the lumen. While maintaining the partial vacuum unbroken in the lumen, the tie coating or layer 289 of SiOxCy is applied by a tie PECVD process comprising applying sufficient power (alternatively the same concept is referred to in this specification as "energy") to generate plasma within the lumen while feeding a gas comprising a linear siloxane precursor, optionally oxygen, and optionally an inert gas diluent. The values of x and y are as determined by X-ray photoelectron spectroscopy (XPS).

Then, while maintaining the partial vacuum unbroken in the lumen, the plasma is extinguished, which has the effect of stopping application of the tie coating or layer of SiOxCy. Optionally in any embodiment, after the plasma used in the tie PECVD coating process is extinguished and before the barrier PECVD coating process is commenced, the feed of the gas employed in the tie PECVD coating process can be stopped. A tie coating or layer of SiOxCy, for which x is from about 0.5 to about 2.4 and y is from about 0.6 to about 3, is produced on the inside surface 303 as a result.

Later during the process, while still maintaining the partial vacuum unbroken in the lumen, the barrier coating or layer 288 is applied by a barrier PECVD process comprising applying sufficient power (alternatively the same concept is referred to in this specification as "energy") to generate plasma within the lumen while feeding a gas comprising a linear siloxane precursor and oxygen Optionally in any embodiment, the power provided to generate plasma within the lumen for applying the barrier coating or layer in a 1-Up coater is from 30 to 80 watts, optionally from 40 to 80 watts, optionally from 50 to 80 watts, optionally from 55 to 65 watts, or optionally in a 4-Up coater is from 175 to 200 watts, optionally from 180 to 190 watts.

Optionally in any embodiment, the plasma generated for applying the barrier coating or layer is applied for 12 to 20 seconds, optionally for 15 to 20 seconds.

Optionally in any embodiment, the barrier coating or layer is applied using a siloxane precursor feed rate, optionally of HMDSO, of from 0.5 to 2 sccm, optionally 0.7 to 1.3 sccm.

Optionally in any embodiment, the barrier coating or layer is applied using a pressure of from 0.5 to 3.5 Torr, optionally from 1 to 2.5 Torr.

Optionally after applying the barrier coating or layer, while maintaining the partial vacuum unbroken in the lumen, the plasma is extinguished, which has the effect of stopping application of the barrier coating or layer. Optionally in any embodiment, after the plasma used in the barrier PECVD coating process is extinguished and before the optional pH protective PECVD coating process, if used, is commenced, the feed of the gas employed in the barrier PECVD coating process can be stopped. A barrier coating or layer of SiOx, wherein x is from 1.5 to 2.9 as determined by XPS is produced between the tie coating or layer and the lumen as a result of barrier coating.

Then optionally, while maintaining the partial vacuum unbroken in the lumen, the pH protective coating or layer 286 of SiOxCy is later applied by a pH protective PECVD process. In this formula, x is from about 0.5 to about 2.4 and y is from about 0.6 to about 3, each as determined by XPS. The pH protective coating or layer is optionally applied between the barrier coating or layer and the lumen, by a pH protective PECVD coating process. The pH protective PECVD process comprises applying sufficient power (alternatively the same concept is referred to in this specification as "energy") to generate plasma within the lumen while feeding a gas comprising a linear siloxane precursor, optionally oxygen, and optionally an inert gas diluent.

Surprisingly, as a result of this processing, the coated vessel 210 made by this process has a lower gas permeation rate constant into the lumen than a corresponding vessel 210 made by the same process except breaking the partial vacuum in the lumen between applying the tie coating or layer and applying the barrier coating or layer.

Alternatively, the coated vessel made by this process including the optional steps has a lower gas permeation rate constant into the lumen than a corresponding vessel made by the same process except breaking the partial vacuum in the lumen between applying the tie coating or layer and applying the barrier coating or layer, and also breaking the partial vacuum in the lumen between applying the barrier coating or layer and the pH protective coating or layer. Optionally in any embodiment, the coated vessel 210 has an oxygen permeation rate constant (OPRC) of from 0.002 to 0.1, optionally from 0.01 to 0.1, optionally from 0.14 to 0.05, optionally from 0.002 to 0.02, optionally from 0.003 to 0.12 μmol/day/cm$^2$/atm.

Optionally in any embodiment, the coated vessel 210 has an oxygen transfer rate of from 0.5 to 12, optionally from 3 to 22, optionally from 3.4 to 12, optionally from 0.5 to 3, optionally from 0.7 to 2 cc/m2/day.

Optionally in any embodiment, the wall has a water vapor transmission rate of less than 2.5 g/m2/day at 50° C. and 90% relative humidity.

Optionally in any embodiment, the PECVD process for applying the tie coating or layer, the barrier coating or layer, and/or the pH protective coating or layer, or any combination of two or more of these, is carried out by applying pulsed power (alternatively the same concept is referred to in this specification as "energy") to generate plasma within the lumen.

Alternatively, the tie PECVD coating process, or the barrier PECVD coating process, or the pH protective PECVD coating process, or any combination of two or more of these, can be carried out by applying continuous power to generate plasma within the lumen.

As a still further alternative, pulsed power can be used for some steps, and continuous power can be used for others. For example, when preparing a trilayer coating or layer composed of a tie coating or layer, a barrier coating or layer, and a pH protective coating or layer, an option specifically contemplated for the tie PECVD coating process and for the pH protective PECVD coating process is pulsed power, and an option contemplated for the corresponding barrier layer is using continuous power to generate plasma within the lumen.

Optionally in any embodiment, the present process further includes the subsequent step of providing a fluid composition in the lumen.

Optionally in any embodiment, the fluid composition includes a blood anticoagulation reagent, for example, buffered sodium citrate solution.

Another aspect of the current invention relates to a sample collection tube incorporating stopper retention features. The following description will focus on blood sample collection tubes, but is equally applicable to tubes for collecting other types of medical samples.

It is sometimes desirable or necessary to collect a sample of blood or another body fluid in one location, then pack the sample to prepare it for transportation to another location, for example to collect a large number of samples from geographically diverse locations at a central laboratory for analysis, or at a central repository for storage after analysis. Since blood or other body fluids collected for medical diagnostic use frequently are infectious substances, it is important to pack the sample carefully so it will not leak during transportation.

One particular aspect of medical sample collection bearing on this problem is that a medical sample in a stoppered vessel is commonly contained at substantially ambient atmospheric pressure at the time and place of collection. Even a blood sample collected in an evacuated blood collection tube commonly is at or near atmospheric pressure just after collection, as the initial vacuum in the sample tube is consumed by drawing the sample into the vessel.

According to 49 CFR 173.196 relating to transportation of Category A and B Infectious Substances, the packing for infectious substances "must be capable of withstanding, without leakage, an internal pressure producing a pressure differential of not less than 95 kPa (0.95 bar, 14 psi)." This translates to an altitude of 70,000 feet.

Accordingly, standard sample collection tubes desirably are designed to satisfy this transportation standard, so they will be useful for transporting medical samples that potentially are infectious agents.

Several aspects of this invention are various adaptations of the vessel 210 shown in FIGS. 1-2 and 4-6 specially adapting it to carry samples without leakage in accord with the requirements of 49 CFR 173.196.

Figure 4:
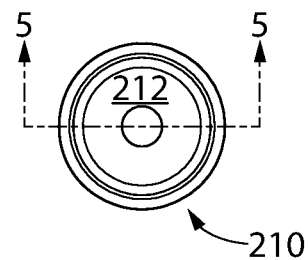
FIG. 4 is a top plan view of a more detailed embodiment of a pharmaceutical package or vessel of FIGS. 1 and 2, suitable for use as an evacuated blood collection tube.
Figure 5:
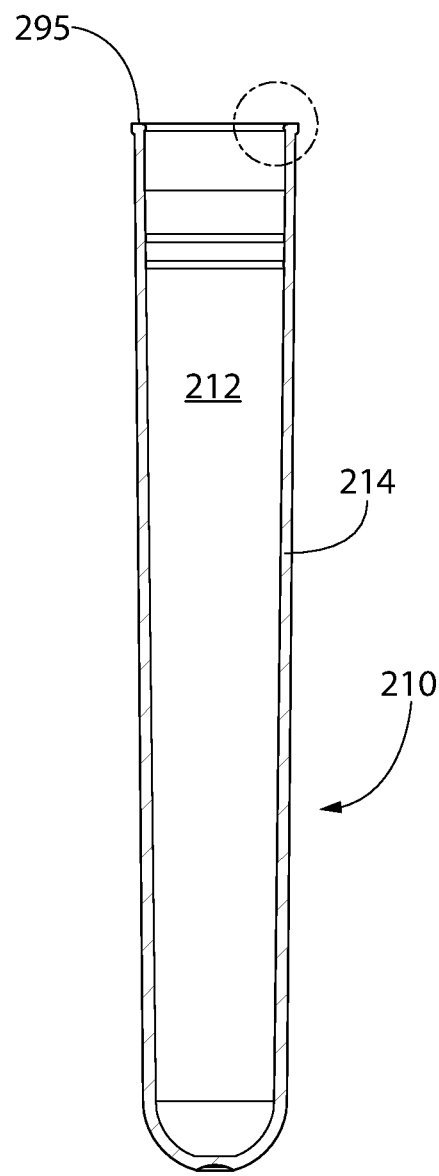
FIG. 5 is a longitudinal section of the embodiment of FIG. 4, taken along the section line 5-5 of FIG. 4.
Figure 6:
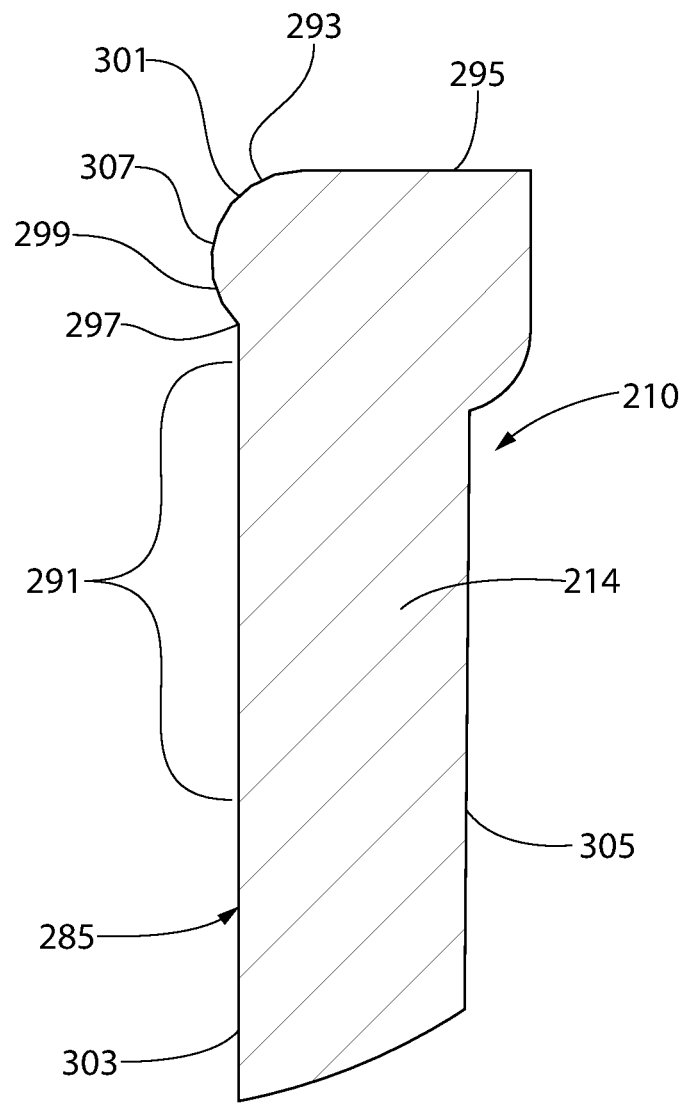
FIG. 6 is an enlarged fragmentary detail view of FIG. 5.

Refer now to FIGS. 4-6. In the illustrated embodiment, the vessel 210 can have a thermoplastic wall 214, although the vessel 210 instead could be made of glass, thermoset plastic, or other materials without limitation, although transparent materials are commonly preferred. The vessel 210 has a top 295 defining an opening, an inside surface 303 defining a lumen 212, an outside surface 305, and a stopper contact area 291 on the inside surface 303 adjacent to the top 295.

One retention feature of the vessel, which may be used alone or in combination with other features, is that the stopper contact area 291 is tapered inward between 0 and 1.3 degrees, for example, which is less than the typical molding taper for a blood sample collection tube. "Tapered inward" means that the diameter of the lumen 212 is reduced regularly going axially from the top (nearest the top 295 of the vessel) to the bottom of the stopper contact area 291, so the inside surface 303 in the stopper contact area 291 defines the sidewall of a truncated cone. For the present purpose, a "taper" of exactly zero degrees is defined as "between" 0 and 1.3 degrees, even though a "taper" of zero is in fact a cylinder that does not taper at all. Additionally, any taper greater than zero degrees to any extent and not greater than 1.3 degrees is within this range of the invention, including a taper of exactly 1.3 degrees. In other words, "between" two numerical limits according to the present definition is inclusive of both limits.

It is also contemplated that a taper of zero is not the absolute lower limit, and a negative taper (tapered outward) can function according to the present invention, although it is less preferred because in some instances fabrication of a negatively tapered part will require more specialized, although well known, techniques, such as a two- or multi-part core, machining, or lost-wax casting.

Alternatively, the stopper contact area 291 can be tapered inward between 0 and 1 degree, optionally between 0 to 0.9 degree, optionally between 0 to 0.8 degree, optionally between 0 to 0.7 degree, optionally between 0 to 0.6 degree, optionally between 0 to 0.5 degree, optionally between 0.3 to 1.3 degrees, optionally between 0.3 to 1 degree, optionally between 0.3 to 0.9 degree, optionally between 0.3 to 0.8 degree, optionally between 0.3 to 0.7 degree, optionally between 0.3 to 0.6 degree, optionally between 0.3 to 0.5 degree, optionally between 0.5 to 1.3 degrees, optionally between 0.5 to 1 degree, optionally between 0.5 to 0.9 degree, optionally between 0.5 to 0.8 degree, optionally between 0.5 to 0.7 degree, optionally between 0.5 to 0.6 degree, optionally 0.5 degree.

Preferably the tapering change is only in the stopper contact area 291. The tapering reduction preferably is not substantially below the stopper contact area 291, as that would change the internal volume. If a change in the internal volume is not important in a given instance, however, the tapering change can extend further than the stopper contact area 291. Additionally, the tapering reduction does not need to extend throughout the entire stopper contact area 291, as tapering reduction over at least a portion of the stopper contact area 291 may be sufficient to provide the desired retention.

Additionally, in any embodiment, to implement limitation of the tapering reduction to the stopper contact area 291, at least a portion of the inside surface 303 of the evacuated blood collection tube located below the stopper contact area 291, is tapered at least 0.7 degree, optionally at least 1 degree, optionally at least 1.5 degree, and as a separately selected option can be tapered at least 0.1 degree more than the stopper contact area 291. A greater taper below the stopper contact area 291 has the benefit of easing simple removal of a one-part core from a mold when the vessel 210 is injection molded.

The effect achieved by reducing the inward taper in the stopper contact area 291 is to reduce or eliminate the tendency of the stopper 216 to loosen if it moves upward with respect to the stopper contact area 291. A resilient stopper compressed by the stopper contact area 291 is biased to expand laterally outward, and thus to move upward toward a region of slightly larger diameter within the stopper contact area 291. This biasing force is reduced by reducing the taper in the stopper contact area 291.

Another retention feature of the vessel 210, which may be used alone or in combination with other retention features, is that a retention lip 293 projects radially inward from the inside surface 305. The inside surface 305 includes a stopper contact area 291 adjacent to and below the retention lip 293. The retention lip 293 functions by bearing down on a stopper 216 lodged in the stopper contact area, requiring the stopper 216 to be further compressed if it is to pass axially across the retention lip 293.

Optionally in any embodiment, the retention lip 293 includes an upper ramp 301 defining an inward taper, optionally a curved inward taper, optionally a convexly curved inward taper, relative to the opening at the top 295, the upper ramp having a lower end 307. Optionally in any embodiment, the retention lip further includes a lower ramp 299 defining an outward taper, optionally a curved outward taper, optionally a convexly curved outward taper, relative to the lower end 307.

Optionally in any embodiment the stoppers 216 are siliconized in a tumbler before use to prevent the stoppers 216 from sticking to each other.

Several other features that apply to each disclosed embodiment are the following. Optionally in any embodiment, the evacuated blood collection tube includes a closure sealing the lumen. Optionally, the closure maintains a vacuum level in the lumen, relative to ambient pressure at sea level, sufficient to draw blood from a patient's vein into the lumen.

Optionally in any embodiment, the closure remains seated in the stopper contact area 291 at a vacuum level of 97.5 kPa below ambient pressure.

Optionally in any embodiment, the evacuated blood collection tube has a shelf life of at least 6 months. As used in this context, the "shelf life" is defined by the amount of time after evacuation the tube maintains a draw volume capacity of at least 90% of the draw volume capacity of a newly evacuated vessel 210 of the same kind.

Optionally in any embodiment, the evacuated blood collection tube has a shelf life of from 6 to 12 months, alternatively from 12 to 18 months, alternatively from 18 to 24 months, alternatively from 24 to 30 months, alternatively from 30 to 36 months, alternatively from 36 to 42 months.

Optionally in any embodiment, the evacuated blood collection tube further includes a fluid composition in the lumen, alternatively an aqueous fluid composition, alternatively including a blood anticoagulation reagent, for example, buffered sodium citrate solution.

Optionally in any embodiment, the evacuated blood collection tube has an oxygen permeation rate constant of from 0.0001 to 0.01, alternatively from 0.0002 to 0.005, alternatively from 0.0005 to 0.003, alternatively from 0.0016 to 0.003 micromol O2/(day×cm2×atm.).

Optionally in any embodiment, the evacuated blood collection tube has a minimum oxygen permeation rate constant of 0.0001, alternatively 0.00016, alternatively 0.0002, alternatively 0.0005, alternatively 0.001, alternatively 0.0016, alternatively 0.002 micromol O2/(day×cm2×atm).

Optionally in any embodiment, the evacuated blood collection tube has a maximum oxygen permeation rate constant of 0.01, alternatively 0.005, alternatively 0.002 micromol O2/(day×cm2×atm Optionally in any embodiment, the evacuated blood collection tube has a water vapor transmission rate of less than 2.5 g/m2/day at 50° C. and 90% relative humidity.

Example 1

A trilayer coating as described in this specification is applied by adjusting the flows of a single organosilicon monomer (HMDSO) and oxygen and also varying the PECVD generating power between each layer (without breaking vacuum between any two layers).

The vessel (here a 6 mL COP vial) is placed on a vessel holder, sealed, and a vacuum is pulled within the vessel. Vials are used to facilitate storage while containing fluid as indicated below. Proportional results are contemplated if blood sample collection tubes are used. After pulling vacuum, the gas feed of precursor, oxygen, and argon is introduced, then at the end of the "plasma delay" continuous (i.e. not pulsed) RF power at 13.56 MHz is turned on to form the tie coating or layer. Then power is turned off, gas flows are adjusted, and after the plasma delay power is turned on for the second layer—an SiOx barrier coating or layer. This is then repeated for a third layer before the gases are cut off, the vacuum seal is broken, and the vessel is removed from the vessel holder. The layers are put down in the order of Tie then Barrier then pH Protective. The process settings are as shown in Table 4:

TABLE 4

|  | O$_2$ (sccm) | Ar (sccm) | HMDSO (sccm) | Power (W) | Deposition Time (sec) |
| --- | --- | --- | --- | --- | --- |
| Tie | 1 | 40 | 2 | 20 | 2.5 |
| Barrier | 100 | 0 | 1 | 60 | 15 |
| pH Protective | 1 | 40 | 2 | 20 | 10 |

As a control, a similar coating process is carried out again, except that when each layer has been deposited the vacuum is broken (causing a "vacuum break") by introducing ambient air into the vessel. After each vacuum break, the vessel is evacuated before applying the next layer.

Figure 3:
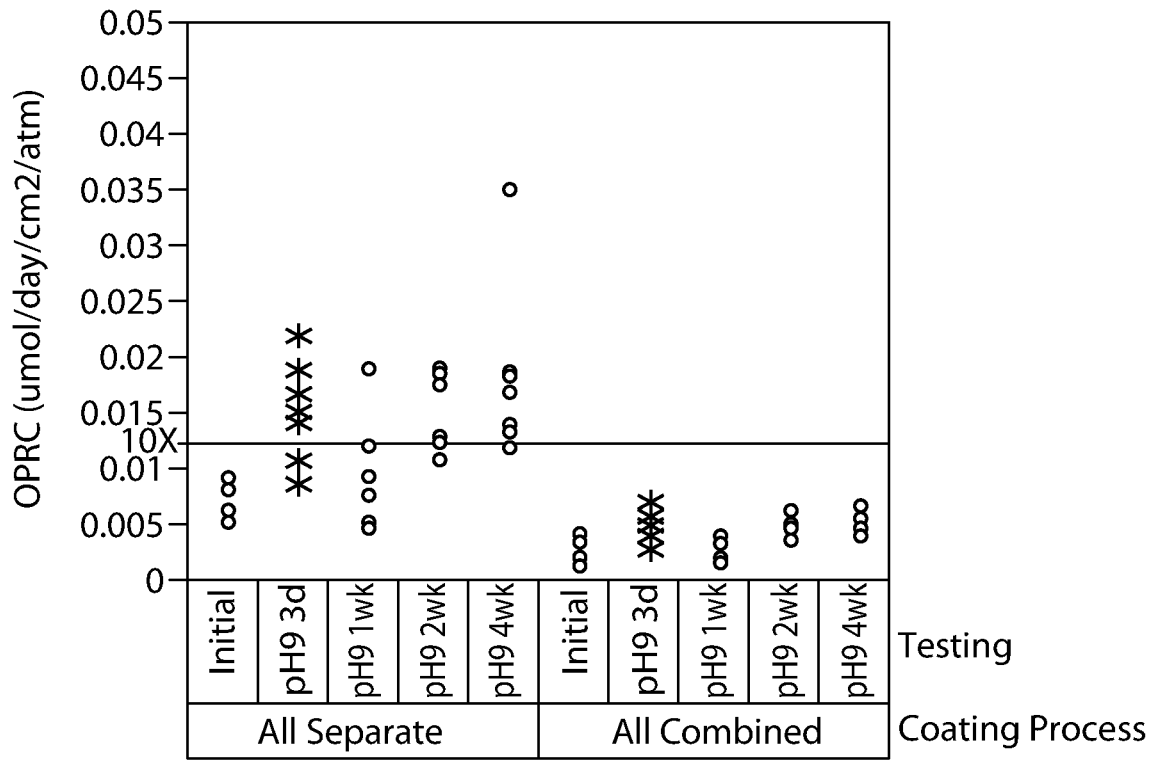
FIG. 3 is a plot of oxygen permeability rate constant (OPRC) vs. storage time with pH 9 buffered phosphate solution for 6 mL vials made according to the present invention ("all combined") with a trilayer coating, compared to similar vials made with a vacuum break between layers.

Each vial except those measured for oxygen permeation rate constant initially is charged with a standard amount of an aqueous phosphate-buffered solution (PBS) of pH 9 at 40° C. and held for the amount of time, in days, indicated in FIG. 3. Then, after each time interval indicated in FIG. 3, groups of vials are cooled, drained, and measured for oxygen permeation rate constant (OPRC) at ambient temperature, reported as μmol (micromole) O2/(day×cm2×atm.), with the results shown in FIG. 3 and tabulated (summary) in Table 5.

Vessels prepared without vacuum breaks ("all combined" runs on the right side of FIG. 3) are compared to the vessels prepared with vacuum breaks ("all separate" runs on the left side of FIG. 3), respecting their oxygen permeation rate constants.

TABLE 5

| | STORAGE TIME, Days | | | | |
|---|---|---|---|---|---|
| | 0 | 3 | 7 | 14 | 28 |
| Mean OPRC, All Combined | 0.00287 | 0.00518 | 0.00274 | 0.00518 | 0.00540 |
| Std. Dev. | 0.00123 | 0.00128 | 0.00094 | 0.00087 | 0.00087 |
| Mean OPRC, All Separate | 0.00774 | 0.01563 | 0.00959 | 0.01543 | 0.01827 |
| Std. Dev. | 0.00138 | 0.00425 | 0.00449 | 0.00334 | 0.00720 |

Surprisingly, as shown in FIG. 3 and the tabulated summary of Table 5, at each storage time the vials processed without intermediate vacuum breaks have much lower (better) OPRC than those processed with intermediate vacuum breaks. It should be noted that the usual oxygen permeation rate constant of corresponding uncoated vials is about 0.122 µmol O2/(day×cm2×atm.), so the vials processed without intermediate vacuum breaks have about 5% of the OPRC of uncoated vials after four weeks of storage.

Example 2

Similar testing on a 6 mL blood sample collection tube is carried out, and in one test the OPRC of a tube coated according to the present "combined" process is 0.00344 µmol O2/(day×cm2×atm.), with a standard deviation of 0.0011.

A parallel test is carried out in which all conditions are the same except that, instead of the plasma-creating power (alternatively the same concept is referred to in this specification as "energy") being applied continuously, it is applied in pulses having a frequency of 5 Hz and a duty cycle of 50%. This means that the full power indicated (W) is applied for 0.1 second, then power is off for 0.1 second, then back on for 0.1 second, then back off for 0.1 second. The result is an OPRC of 0.00380 µmol O2/(day×cm2×atm.), with a standard deviation of 0.0015 under pulsed power. In either case, the OPRC is about 8% of the OPRC of a similar uncoated vessel.

Example 3

A test similar to Example 1 is carried out, except that, instead of the plasma-creating power (alternatively the same concept is referred to in this specification as "energy") being applied continuously, it is applied in pulses having a frequency of 5 Hz and a duty cycle of 50%, repeating for the total time indicated in Table 6.

TABLE 6

| | $O_2$ (sccm) | Ar (sccm) | HMDSO (sccm) | Power (W) | Deposition Time (sec) | Frequency (Hz) | Duty Cycle (%) |
|---|---|---|---|---|---|---|---|
| Tie | 1 | 40 | 2 | 20 | 2.5 | 5 | 50 |
| Barrier | 100 | 0 | 1 | 60 | 15 | 5 | 50 |
| Protective | 1 | 40 | 2 | 20 | 10 | 5 | 50 |

OPRC results approximately proportional to those obtained with continuous power are observed.

Example 4

This study was carried out to determine the effect of applied electrical power during the coating process on the resulting Oxygen Transmission Rates (OTR) or Oxygen Permeation Rate Constant (OPRC) of the coating or layer.

A trilayer coating or layer as described in this specification was applied to a vessel (here a 4 mL COP blood sample collection tube, and the same in other tests except as otherwise indicated) by applying a tie layer using the process settings shown in Table 7 for a 1-Up unit, then a barrier layer using the process settings shown in Table 8, and finally a pH protective layer using the process settings shown in Table 7 for a 1-Up unit. The 1-Up coating unit was a PECVD station where vacuum supply, process gases, and RF power were supplied to one individual article to deposit the barrier coating or layer system on the inside of said article.

The PECVD generating power and other process settings were changed between each layer of the trilayer coating or layer (without breaking vacuum between any two layers). During the trilayer coating process, the power for the tie layer and the pH protective layer (i.e. the first and the third layer) was kept unchanged. The power for the barrier coating or layer was varied as shown in Table 8 to see how it affected the barrier performance (expressed as oxygen transmission rate (OTR) or oxygen permeation rate constant (OPRC)).

TABLE 7

Coating Parameters for Tie layer and pH Protective Layer

| Layer | Argon sccm | Oxygen sccm | HMDSO sccm | Power (W) | Time (s) | Pressure | Pulsing | Hz | Duty Cycle |
|---|---|---|---|---|---|---|---|---|---|
| 1-Up Adhesive/Protective Process | | | | | | | | | |
| Adhesive | 40 | 1 | 2 | 35 | 5 | 1.9 Torr | Yes | 5 | 50% |
| Protective | 40 | 1 | 2 | 35 | 10 | 1.9 Torr | Yes | 5 | 50% |
| 4-Up Adhesive/Protective Process | | | | | | | | | |
| Adhesive | 40 | 2 | 4 | 150 | 5 | 1.9 Torr | Yes | 5 | 50% |
| Protective | 40 | 2 | 4 | 150 | 10 | 1.9 Torr | Yes | 5 | 50% |

The coating process was carried out as follows. The vessel was placed on a vessel holder, sealed, and a vacuum was pulled within the vessel. After pulling vacuum, the gas feed of precursor, oxygen, and argon was introduced, then after a plasma delay, RF power was turned on in pulses to generate plasma and form the tie coating or layer. The power was applied in pulses having a frequency of 5 Hz and a duty cycle of 50%. This means that the full power indicated (W) was applied for 0.1 second, then power was off for 0.1 second, then back on for 0.1 second, then back off for 0.1 second. Then power was turned off, gas flows were adjusted, and after the plasma delay, the RF power was turned on in the same unit for the second layer—a SiOx barrier coating or layer. The RF power for the barrier coating or layer was applied continuously. The same pulsed RF power as for the tie coating or layer was then repeated for a third layer before the gases were cut off, the vacuum seal was broken, and the vessel was removed from the vessel holder. The layers were put down in the order of tie then barrier then pH protective.

Each blood sample collection tube was measured for oxygen permeation rate constant (OPRC) at ambient temperature, reported as μmol (micromole) O2/(day×cm2×atm) with the results of OPRC and OTR shown in FIGS. 3A and 3B and tabulated in Table 8. "Part pressure" in Table 8 is the total pressure of all constituents within one part or vessel.

Table 8 shows that higher electrical power results in a barrier coating or layer with lower OPRC (i.e. better barrier performance). After 60 W, continued increasing of electrical power does not improve the barrier performance any more, as dependent on the volume of the article in this case blood sample collection tube.

TABLE 8

Effect Of Electrical Power
HMDSO (sccm) = 1.0, O2 (sccm) = 100.0, Time(s) = 10.0

| Permeance (OPRC, μmol/day/cm²/atm) | | Oxygen Transmission Rate (OTR, cc/m²/day) | | Process Information | |
|---|---|---|---|---|---|
| | | | | Power | Part Pressure |
| Avg. | 2*St. Dev. | Avg. | 2*St. Dev. | (W) | (Torr) | Unit |
| 0.105 | 0.0053 | 25.74 | 1.31 | 20.0 | 3.92 | 1-Up |
| 0.090 | 0.0152 | 21.90 | 3.71 | 30.0 | 3.92 | 1-Up |
| 0.049 | 0.0392 | 12.06 | 9.58 | 40.0 | 3.92 | 1-Up |
| 0.018 | 0.0054 | 4.47 | 1.33 | 50.0 | 3.92 | 1-Up |
| 0.014 | 0.0031 | 3.45 | 0.76 | 60.0 | 3.92 | 1-Up |
| 0.017 | 0.0031 | 4.05 | 0.77 | 70.0 | 3.92 | 1-Up |
| 0.017 | 0.0096 | 4.22 | 2.34 | 80.0 | 3.92 | 1-Up |
| 0.16 | 0.0052 | 38.69 | 1.27 | | | Uncoated |

Example 5

This study was to determine the effect of coating time on the resulting Oxygen Transmission Rates (OTR) or Oxygen Permeation Rate Constant (OPRC) of the coating or layer.

A trilayer coating or layer as described in this specification was applied, adjusting the coating time (without breaking vacuum between any two layers), and the resulting OPRC and OTR were compared. During the trilayer process, the coating parameters for tie layer and pH protective layer (i.e. the first and the third layer) were those of Table 7 for a 1-Up unit. The coating parameters for the barrier coating or layer (i.e. the second layer) were those of Table 9. The coating time for the barrier coating or layer was varied as shown in Table 9 to see how it affected the barrier performance (expressed as oxygen transmission rate (OTR) or oxygen permeation rate constant (OPRC)). The results are shown in Table 9 and FIGS. 5A and 5B.

TABLE 9

Effect Of Coating Time
HMDS(sccm) = 1.0, O2(sccm) = 100, Power(w) = 60

| Permeance μmol/day/cm²/atm | | Oxygen Transmission Rate cc/m²/day | | Process Information | | |
|---|---|---|---|---|---|---|
| | | | | | Part | |
| Avg. | 2*St. Dev. | Avg. | 2*St. Dev. | Time (s) | Pressure (Torr) | Unit |
| 0.0150 | 0.0063 | 3.68 | 1.53 | 10.0 | 3.92 | 1-Up |
| 0.0031 | 0.0025 | 0.76 | 0.62 | 15.0 | 3.92 | 1-Up |
| 0.0029 | 0.0017 | 0.71 | 0.42 | 20.0 | 3.92 | 1-Up |

The results show that the barrier coating or layer performance was improved with the increase of coating time until the time reached 15 seconds. After 15 seconds, continued increasing the coating time did not improve the barrier performance any more, as dependent on the volume of the article in this case blood tube.

Example 6

This study was to determine the effect of feeding rate of the coating or layer precursor HMDSO during the barrier coating process on the resulting Oxygen Transmission Rates (OTR) or Oxygen Permeation Rate Constant (OPRC) of the trilayer coating or layer.

A trilayer coating or layer as described in this specification was applied essentially as before, using the conditions of Table 7 for the tie coating or layer and pH protective coating or layer, and the conditions of Table 10 for the barrier coating or layer, without breaking vacuum between any two layers. The effects of different HMDSO feeding rates for the barrier layer were compared.

These tests were carried out both using the 1-Up unit previously described and a 4-Up unit. The 4-Up unit was similar to the 1-Up unit, but the vacuum supply, process gases, and RF power were uniformly split and supplied uniformly to four individual vessels. By maintaining uniformity with vacuum supply and process gases, the pressure within each vessel of a 4-Up remains the same as the single vessel of a 1-Up.

During the trilayer coating process, HMDSO feeding rate for tie layer and pH protective layer (i.e. the first and the third layer) were kept unchanged. HMDSO feeding rate for the barrier coating or layer was varied to see how it affects the barrier performance (expressed as oxygen transmission rate (OTR) or oxygen permeation rate constant (OPRC)).

The results are shown in Table 10. The barrier coating or layer performance was improved with decrease of HMDSO feeding rate until the feeding rate reached 1 sccm. After 1 sccm, continued lowering HMDSO feeding rate did not improve the barrier performance any more, as dependent on the volume of the article in this case blood sample collection tube.

TABLE 10

Effect Of HMDSO feeding rate

Time(s) = 10.0, O2(sccm) = 100, Power(w) = 60

| Permeance μmol/day/cm²/atm | | Oxygen Transmission Rate cc/m²/day | | Process Information | | |
|---|---|---|---|---|---|---|
| | | | | | Part | |
| | | | | HMDSO | Pressure | |
| Avg. | 2*St. Dev. | Avg. | 2*St. Dev. | (sccm) | (Torr) | Unit |
| 0.117 | 0.0130 | 28.63 | 3.18 | 3.0 | 3.92 | 1-Up |
| 0.0267 | 0.0163 | 6.52 | 3.98 | 2.0 | 3.92 | 1-Up |
| 0.0041 | 0.0019 | 0.99 | 0.46 | 1.0 | 3.92 | 1-Up |
| 0.0090 | 0.0026 | 2.20 | 0.63 | 0.5 | 3.92 | 1-Up |

Time(s) = 15.0, O2(sccm) = 100, Power(w) = 60

| Permeance μmol/day/cm²/atm | | cc/m²/day | | Process Information | | | |
|---|---|---|---|---|---|---|---|
| | | | | | | Part | |
| | | | | HMDSO | Power | Pressure | |
| Avg. | 2*St. Dev. | Avg. | 2*St. Dev. | (sccm) | (W) | (Torr) | Unit |
| 0.127 | 0.0050 | 31.01 | 1.22 | 6.0 | 145.0 | 3.92 | 4-Up |
| 0.0746 | 0.0050 | 18.24 | 1.22 | 3.0 | 145.0 | 3.92 | 4-Up |
| 0.0341 | 0.0132 | 8.35 | 3.24 | 1.0 | 175.0 | 3.92 | 4-Up |

Example 7

In this example, the power, HMDSO feeding rate, and coating time were varied to optimize the coating conditions to obtain the best barrier coating or layer performance (i.e. the lowest OPRC and OTR). The process information is shown in Table 7 (4-Up) for the tie coating or layer and pH protective coating or layer and Table 11 for the barrier layer. The results are shown in Table 11. The best results were achieved in the second test with a feed of 1.0 sccm HMDSO, power of 185.0 watts, and time of 15.0 sec.

TABLE 11

Effect of Power, HMDSO Feeding Rate and Time
O2(sccm) = 100

| Permeance μmol/day/cm²/atm | | Oxygen Transmission Rate cc/m²/day | | Process Information | | | | |
|---|---|---|---|---|---|---|---|---|
| | | | | | | | Part | |
| | | | | HMDSO | Power | Time | Pressure | |
| Avg. | 2*St. Dev | Avg. | 2*St. Dev. | (sccm) | (W) | (s) | (Torr) | Unit |
| 0.053 | 0.0264 | 12.85 | 6.45 | 1.0 | 175.0 | 10.0 | 3.92 | 4-Up |
| 0.0162 | 0.0023 | 3.97 | 0.57 | 1.0 | 185.0 | 15.0 | 3.92 | 4-Up |
| 0.0234 | 0.0050 | 5.73 | 1.22 | 1.0 | 185.0 | 10.0 | 3.92 | 4-Up |
| 0.0215 | 0.0044 | 5.26 | 1.08 | 2.0 | 200.0 | 15.0 | 3.92 | 4-Up |

Example 8

This study was to determine the effect of applied pressure during the coating process on the resulting Oxygen Transmission Rates (OTR) or Oxygen Permeation Rate Constant (OPRC) of the trilayer coating or layer. Compared to Examples 4-7 wherein the applied pressure was 3.92 torr, in Example 8, the applied pressure was 1.6 torr. The results were shown in Table 12.

TABLE 12

| Effect Of Pressure $O_2$ (sccm) = 75.0, Power(w) = 200 | | | | | | | |
|---|---|---|---|---|---|---|---|
| Oxygen Transmission | | | | Process Information | | | |
| Permeance $\mu mol/day/cm^2/atm$ | | Rate $cc/m^2/day$ | | HMDSO | Time | Part Pressure | |
| Avg. | 2*St. Dev. | Avg. | 2*St. Dev. | (sccm) | (s) | (Torr) | Unit |
| 0.0043 | 0.0028 | 1.04 | 0.69 | 1.0 | 10.0 | 1.60 | 4-Up |
| 0.0044 | 0.0084 | 1.08 | 2.06 | 1.5 | 10.0 | 1.60 | 4-Up |
| 0.0049 | 0.0034 | 1.20 | 0.83 | 1.0 | 15.0 | 1.60 | 4-Up |
| 0.0039 | 0.0040 | 0.96 | 0.99 | 1.5 | 15.0 | 1.60 | 4-Up |

The results show that lower pressure improved the barrier coating or layer performance.

Example 9

This was a Pressure Differential Test and the testing conditions were set to mimic ambient atmospheric pressure at an altitude of 70,000 feet. This testing was done to determine if the trilayer coated bloodtubes with the retention features described in the specification can stay intact and endure the pressure change. This testing was important to predict if the bloodtubes of this invention were fit for transporting infectious blood samples. It was a pass/fail testing.

10 mL trilayer coated COP blood sample collection tubes including both retention features described above (a retention lip 293 and a taper of about 0.5° in the stopper contact area 291) were sealed with stoppers which had been siliconized (coated with silicone oil) in a tumbler to prevent them from sticking to each other. The sealed blood sample collection tubes were evacuated and filled with 9.33 mL±0.03 mL of red colored water before they were placed upright and inverted into a 700 mL beaker, which was then placed within a metal canister for pressurization/vacuum. A maximum quantity of 10 filled blood sample collection tubes were tested at once. Once the metal canister was sealed, the vacuum valve was opened slowly to reduce the pressure to −28.8 in. Hg gauge (−14.1 psig, or a pressure differential of 97.5 kPa). This method approximates the effect of filling and stoppering the vessels at sea level ambient pressure, then elevating them to 70,000 feet above sea level, since a standardized pressure difference is applied regardless of the elevation or barometric pressure where the tubes are filled.

Filled blood sample collection tube samples were held at this vacuum level for 30 minutes. After the 30 minutes passed, the vacuum level was slowly raised to ambient pressure. Samples were then removed and inspected for stopper movement and leaks.

The blood sample collection tubes with the retention features described in the specification passed Pressure Differential Testing with no leaks. The same blood sample collection tubes without the retention features failed the Pressure Differential Testing.

What is claimed is:

1. An evacuated blood collection tube comprising:
   a thermoplastic vessel wall; and
   a stopper;
   the thermoplastic vessel wall having
      a top defining an opening,
      an inside surface defining a lumen, the inside surface having one or more coatings applied by PECVD,
      an outside surface, and
      a stopper contact area adjacent to the top, the stopper contact area being a portion of the inside surface that contacts the stopper;
   the stopper being seated in the stopper contact area and sealing the lumen;
   wherein the stopper contact area is tapered inward between 0 and 1.3 degrees and the entirety of the inside surface below the stopper contact area is tapered inward at least 0.1 degree more than the stopper contact area; and
   wherein the stopper contact area is continuous with the inside surface below the stopper contact area.

2. The evacuated blood collection tube of claim 1, in which the entirety of the inside surface below the stopper contact area is tapered at least 1.5 degrees.

3. The evacuated blood collection tube of claim 1, the stopper maintaining a vacuum level in the lumen, relative to ambient pressure at sea level, sufficient to draw blood from a patient's vein into the lumen.

4. The evacuated blood collection tube of claim 3, in which the stopper remains seated in the stopper contact area at a vacuum level of 97.5 kPa below ambient pressure.

5. The evacuated blood collection tube of claim 3, having a shelf life of at least 6 months, the shelf life defined by the amount of time after evacuation the tube maintains a draw volume capacity of at least 90% of the draw volume capacity of a newly evacuated vessel of the same kind.

6. The evacuated blood collection tube of claim 3, further comprising a fluid composition in the lumen.

7. The evacuated blood collection tube of claim 6, wherein the fluid composition comprises a blood anticoagulation agent.

8. The evacuated blood collection tube of claim 7, wherein the blood anticoagulation agent is a buffered sodium citrate solution.

9. The evacuated blood collection tube of claim 3, having an oxygen permeation rate constant of from 0.0001 to 0.01 micromol $O_2/(day \times cm^2 \times atm)$.

10. The evacuated blood collection tube of claim 3, in which the wall has a water vapor transmission rate of less than 2.5 g/m²/day at 50° C. and 90% relative humidity.

11. The evacuated blood collection tube of claim 1, wherein the inside surface comprises:
- a barrier layer of SiOx applied by a PECVD coating process, wherein x is from 1.5 to 2.9 as determined by XPS, and
- at least one of:
  - a tie layer of SiOxCy applied by a PECVD coating process, and
  - a pH protective layer of SiOxCy applied by a PECVD coating process.

12. The evacuated blood collection tube of claim 1, wherein the inside surface comprises:
- a tie layer of SiOxCy applied by a PECVD coating process,
- a barrier layer of SiOx applied by a PECVD coating process, wherein x is from 1.5 to 2.9 as determined by XPS, between the tie coating or layer and the lumen, and
- a pH protective layer of SiOxCy applied by a PECVD coating process, wherein x is from about 0.5 to about 2.4 and y is from about 0.6 to about 3, each as determined by XPS, between the barrier layer and the lumen.

13. The evacuated blood collection tube of claim 1, in which the stopper contact area is tapered inward between 0.3 and 1 degree.

* * * * *